US011447913B2

(12) United States Patent
Stewart et al.

(10) Patent No.: US 11,447,913 B2
(45) Date of Patent: Sep. 20, 2022

(54) FUNGAL TEXTILE MATERIALS AND LEATHER ANALOGS

(71) Applicant: The Fynder Group, Inc., Chicago, IL (US)

(72) Inventors: Brendan Allen Stewart, Bozeman, MT (US); Larry Andrew Alegria, Bozeman, MT (US); Ryan Jacob Totman, Bozeman, MT (US); Yuval Charles Avniel, Missoula, MT (US)

(73) Assignee: The Fynder Group, Inc., Chicago, IL (US)

( * ) Notice: Subject to any disclaimer, the term of this patent is extended or adjusted under 35 U.S.C. 154(b) by 0 days.

(21) Appl. No.: 17/410,859

(22) Filed: Aug. 24, 2021

(65) Prior Publication Data

US 2021/0388558 A1 Dec. 16, 2021

Related U.S. Application Data

(60) Division of application No. 17/030,322, filed on Sep. 23, 2020, now Pat. No. 11,118,305, which is a continuation of application No. 16/904,520, filed on Jun. 17, 2020.

(60) Provisional application No. 62/966,525, filed on Jan. 27, 2020, provisional application No. 62/951,332, filed on Dec. 20, 2019, provisional application No. 62/862,680, filed on Jun. 18, 2019.

(51) Int. Cl.
| | |
|---|---|
| *C08L 99/00* | (2006.01) |
| *D06N 3/00* | (2006.01) |
| *B29C 70/06* | (2006.01) |
| *B29C 70/42* | (2006.01) |
| *C08J 5/24* | (2006.01) |
| *B29K 105/08* | (2006.01) |
| *B29K 105/00* | (2006.01) |
| *B29K 311/00* | (2006.01) |

(52) U.S. Cl.
CPC ........... *D06N 3/0015* (2013.01); *B29C 70/06* (2013.01); *B29C 70/42* (2013.01); *C08J 5/24* (2013.01); *C08J 5/245* (2021.05); *C08J 5/249* (2021.05); *C08L 99/00* (2013.01); *D06N 3/0013* (2013.01); *B29K 2105/0038* (2013.01); *B29K 2105/0872* (2013.01); *B29K 2311/00* (2013.01); *C08J 2399/00* (2013.01); *C08J 2405/08* (2013.01); *C08J 2429/04* (2013.01); *C08J 2431/04* (2013.01); *C08L 2205/06* (2013.01); *C08L 2312/00* (2013.01)

(58) Field of Classification Search
CPC ...... C12N 1/14; C12N 1/145; C12R 2001/64; C08L 99/00; B29C 70/06; C08J 5/24
See application file for complete search history.

(56) References Cited

U.S. PATENT DOCUMENTS

| | | |
|---|---|---|
| 2,450,055 A | 9/1948 | Nord |
| 2,811,442 A | 10/1957 | Van Horn et al. |
| 2,822,319 A | 2/1958 | Jacques |
| 3,149,051 A | 9/1964 | Yoshida et al. |
| 3,151,038 A | 9/1964 | Gray |
| 3,937,654 A | 2/1976 | Solomons et al. |
| 3,937,693 A | 2/1976 | Towersey et al. |
| 4,041,189 A | 8/1977 | Towersey et al. |
| 4,063,383 A | 12/1977 | Green |
| 4,466,988 A | 8/1984 | Towersey et al. |
| 4,530,834 A | 7/1985 | McCabe et al. |
| 4,539,036 A | 9/1985 | Nashberger |
| 4,555,485 A | 11/1985 | Marsh |
| 4,800,093 A | 1/1989 | Hogan et al. |
| 4,960,413 A | 10/1990 | Sagar et al. |
| 5,074,959 A | 12/1991 | Yamanaka et al. |
| 5,258,293 A | 11/1993 | Lynd et al. |
| 5,854,056 A | 12/1998 | Dschida |
| 5,904,943 A | 5/1999 | Finnigan et al. |
| 6,264,879 B1 | 7/2001 | Addie et al. |
| 6,423,337 B1 | 7/2002 | Edebo |
| 6,824,682 B2 | 11/2004 | Branson |
| 6,979,426 B2 | 12/2005 | Teall et al. |
| 6,991,919 B1 | 1/2006 | Porter et al. |
| 7,045,160 B1 | 5/2006 | Haan et al. |
| 7,059,993 B2 | 6/2006 | Ding et al. |
| 7,169,821 B2 | 1/2007 | Branson |
| 7,420,072 B2 | 9/2008 | Fleisher |
| 7,449,313 B2 | 11/2008 | Rush |
| 7,452,515 B1 | 11/2008 | Lafleur et al. |

(Continued)

FOREIGN PATENT DOCUMENTS

| | | |
|---|---|---|
| CA | 751389 | 1/1967 |
| CN | 1059662 | 3/1992 |

(Continued)

OTHER PUBLICATIONS

Appels et al. Fabrication factors influencing mechanical, moisture- and water-related properties of mycelium-based composites, Materials and Design, 161(2019)64-71, published on Nov. 11, 2018.*
Shi et al Evaluation of Biodegradable Films Made of Waste Mycelium and Poly (Vinyl Alcohol) on the Yield of Pak-Choi, J Polym Environ (2012) 20:492-500, Published online: Dec. 20, 2011.*
Shahid et al., "Screening and optimization of some inorganic salts for the production of ergot alkaloids from Penicillium species using surface culture fermentation process," Pak. J. Pharm. Sci., vol. 29, No. 2, Mar. 2016, pp. 407-414.
Speelman, "Fungal Mats in Solid-State Fermentation," Apr. 18, 2005, Ph.D. Thesis Submitted to Wageningen University, Wageningen, The Netherlands, 164 pages.

(Continued)

*Primary Examiner* — Gregory Listvoyb
(74) *Attorney, Agent, or Firm* — Sheridan Ross P.C.

(57) ABSTRACT

Textile compositions comprising at least one filamentous fungus are disclosed, as are methods for making and using such textile compositions. Embodiments of the textile compositions generally include at least one of a plasticizer, a polymer, and a crosslinker, in addition to the filamentous fungus. The disclosed textile compositions are particularly useful as analogs or substitutes for conventional textile compositions, including but not limited to leather.

30 Claims, 15 Drawing Sheets

(56) References Cited

U.S. PATENT DOCUMENTS

| | | |
|---|---|---|
| 7,514,247 B2 | 4/2009 | Rush |
| 7,524,982 B2 | 4/2009 | Dall'Agnol et al. |
| 7,605,281 B2 | 10/2009 | Oku et al. |
| 7,635,492 B2 | 12/2009 | Finnigan et al. |
| 7,700,076 B2 | 4/2010 | Tamarkin et al. |
| 8,001,719 B2 | 8/2011 | Bayer et al. |
| 8,124,094 B2 | 2/2012 | Kim et al. |
| 8,227,225 B2 | 7/2012 | Rocco et al. |
| 8,227,233 B2 | 7/2012 | Kalisz et al. |
| 8,298,809 B2 | 10/2012 | Kalisz et al. |
| 8,541,214 B2 | 9/2013 | Hickey et al. |
| 8,672,245 B2 | 3/2014 | Finnigan et al. |
| 8,943,763 B2 | 2/2015 | Lim |
| 8,969,030 B2 | 3/2015 | Neto |
| 8,999,687 B2 | 4/2015 | Bayer et al. |
| 9,085,763 B2 | 7/2015 | Winiski et al. |
| 9,253,889 B2 | 2/2016 | Bayer et al. |
| 9,370,200 B2 | 6/2016 | Gibbons et al. |
| 9,394,512 B2 | 7/2016 | Bayer et al. |
| 9,410,116 B2 | 8/2016 | Ross |
| 9,469,838 B2 | 10/2016 | Schaak et al. |
| 9,485,917 B2 | 11/2016 | Bayer et al. |
| 9,555,395 B2 | 1/2017 | Araldi et al. |
| 9,714,180 B2 | 7/2017 | McIntyre et al. |
| 9,795,088 B2 | 10/2017 | Bayer et al. |
| 9,796,989 B2 | 10/2017 | Kozubal et al. |
| 9,801,345 B2 | 10/2017 | Bayer et al. |
| 9,803,171 B2 | 10/2017 | Bayer et al. |
| 9,879,219 B2 | 1/2018 | McIntyre et al. |
| 9,914,906 B2 | 3/2018 | Winiski et al. |
| 9,951,307 B2 | 4/2018 | Ross |
| 9,994,804 B2 | 6/2018 | Menon et al. |
| 10,125,347 B2 | 11/2018 | Winiski |
| 10,144,149 B2 | 12/2018 | McIntyre et al. |
| 10,154,627 B2 | 12/2018 | McIntyre et al. |
| 10,266,695 B2 | 4/2019 | Lucht et al. |
| 10,344,306 B2 | 7/2019 | Kozubal et al. |
| 10,407,675 B2 | 9/2019 | Bayer et al. |
| 10,525,662 B2 | 1/2020 | Bayer et al. |
| 10,533,155 B2 * | 1/2020 | Kozubal ............... C12N 1/145 |
| 10,537,070 B2 | 1/2020 | Betts et al. |
| 10,577,579 B2 | 3/2020 | Kozubal et al. |
| 10,583,626 B2 | 3/2020 | Bayer et al. |
| 10,589,489 B2 | 3/2020 | Bayer et al. |
| 10,590,379 B2 | 3/2020 | Kozubal et al. |
| 10,604,734 B2 | 3/2020 | Amstislavski et al. |
| 10,687,738 B2 * | 6/2020 | MacDougall ....... G01B 9/02091 |
| 10,787,638 B2 | 9/2020 | Kozubal et al. |
| 10,851,396 B2 | 12/2020 | Kozubal et al. |
| 11,001,801 B2 | 5/2021 | Kozubal et al. |
| 11,015,168 B2 | 5/2021 | Kozubal et al. |
| 11,039,635 B2 | 6/2021 | Macur et al. |
| 11,118,305 B2 | 9/2021 | Stewart et al. |
| 2003/0096342 A1 | 5/2003 | Adney et al. |
| 2003/0104522 A1 | 6/2003 | Ding et al. |
| 2003/0108988 A1 | 6/2003 | Ding et al. |
| 2003/0111410 A1 | 6/2003 | Branson |
| 2003/0157219 A1 | 8/2003 | Bljl et al. |
| 2003/0175182 A1 | 9/2003 | Teall et al. |
| 2004/0038334 A1 | 2/2004 | Ding et al. |
| 2004/0185162 A1 | 9/2004 | Finnigan et al. |
| 2004/0197461 A1 | 10/2004 | Finnigan et al. |
| 2004/0211721 A1 | 10/2004 | Stamets |
| 2005/0026262 A1 | 2/2005 | Yoshitani et al. |
| 2005/0097815 A1 | 5/2005 | Wasser et al. |
| 2005/0113467 A1 | 5/2005 | Branson |
| 2005/0255013 A1 | 11/2005 | Teall et al. |
| 2006/0172405 A1 | 8/2006 | Yoshitani et al. |
| 2006/0177551 A1 | 8/2006 | Thorre |
| 2006/0182857 A1 | 8/2006 | Thorre |
| 2007/0010681 A1 | 1/2007 | Dall'Agnol et al. |
| 2007/0099278 A1 | 5/2007 | Aare |
| 2007/0110862 A9 | 5/2007 | Thorre |
| 2007/0122667 A1 | 5/2007 | Kelley |
| 2007/0161095 A1 | 7/2007 | Gurin |
| 2007/0167642 A1 | 7/2007 | Oku et al. |
| 2007/0260079 A1 | 11/2007 | Fleisher |
| 2008/0044850 A1 | 2/2008 | Taylor et al. |
| 2008/0102503 A1 | 5/2008 | Rush |
| 2008/0145577 A1 | 6/2008 | Bayer et al. |
| 2008/0202021 A1 | 8/2008 | Powell |
| 2008/0282606 A1 | 11/2008 | Plaza et al. |
| 2008/0282687 A1 | 11/2008 | Park et al. |
| 2008/0299633 A1 | 12/2008 | Rush |
| 2008/0313955 A1 | 12/2008 | Silva et al. |
| 2009/0054701 A1 | 2/2009 | Abhari |
| 2009/0142467 A1 | 6/2009 | Aldred et al. |
| 2009/0148558 A1 | 6/2009 | Kim et al. |
| 2009/0178330 A1 | 7/2009 | Parejo et al. |
| 2009/0235579 A1 | 9/2009 | Kim et al. |
| 2010/0227357 A1 | 9/2010 | Redman et al. |
| 2010/0310746 A1 | 12/2010 | Leser et al. |
| 2011/0045558 A1 | 2/2011 | Bauwellers et al. |
| 2012/0052536 A1 | 3/2012 | Medoff et al. |
| 2012/0124839 A1 | 5/2012 | Kalisz et al. |
| 2012/0225471 A1 | 9/2012 | McIntyre et al. |
| 2012/0270302 A1 | 10/2012 | Bayer et al. |
| 2012/0315687 A1 | 12/2012 | Bayer et al. |
| 2013/0095560 A1 | 4/2013 | McIntyre et al. |
| 2013/0156922 A1 | 6/2013 | Vessio et al. |
| 2013/0202855 A1 | 8/2013 | Kalisz et al. |
| 2013/0234058 A1 | 9/2013 | Albarran |
| 2013/0309755 A1 | 11/2013 | McIntyre et al. |
| 2014/0056653 A1 | 2/2014 | Scully et al. |
| 2014/0178529 A1 | 6/2014 | Anton et al. |
| 2014/0186927 A1 | 7/2014 | Winiski et al. |
| 2014/0275507 A1 | 9/2014 | Van Leeuwen et al. |
| 2015/0033620 A1 | 2/2015 | Greetham et al. |
| 2015/0044356 A1 | 2/2015 | Bootsma et al. |
| 2015/0101509 A1 | 4/2015 | McIntyre et al. |
| 2015/0119783 A1 | 4/2015 | Burgert et al. |
| 2016/0053418 A1 | 2/2016 | Eckert et al. |
| 2016/0058049 A1 | 3/2016 | Langan et al. |
| 2016/0249638 A1 | 9/2016 | Gibbons et al. |
| 2017/0142967 A1 | 5/2017 | Reed et al. |
| 2017/0367964 A1 | 12/2017 | Yamamoto et al. |
| 2018/0014468 A1 | 1/2018 | Ross et al. |
| 2018/0014567 A1 | 1/2018 | Finnigan et al. |
| 2018/0146627 A1 | 5/2018 | Ross et al. |
| 2018/0148682 A1 | 5/2018 | Ross |
| 2018/0282529 A1 | 10/2018 | Kaplan-Bie |
| 2018/0368337 A1 | 12/2018 | McIntyre et al. |
| 2019/0024303 A1 | 1/2019 | Lee et al. |
| 2019/0059431 A1 | 2/2019 | Kozubal et al. |
| 2019/0090436 A1 | 3/2019 | Betts et al. |
| 2019/0223485 A1 | 7/2019 | Finnigan et al. |
| 2019/0284307 A1 | 9/2019 | Chase et al. |
| 2019/0307157 A1 | 10/2019 | Kozubal et al. |
| 2019/0322997 A1 | 10/2019 | Schaak |
| 2019/0330667 A1 | 10/2019 | Kozubal et al. |
| 2019/0338240 A1 | 11/2019 | Carlton et al. |
| 2019/0357454 A1 | 11/2019 | Mueller et al. |
| 2019/0359931 A1 | 11/2019 | Mueller et al. |
| 2019/0373934 A1 | 12/2019 | Huggins et al. |
| 2019/0373935 A1 | 12/2019 | Huggins et al. |
| 2019/0390156 A1 | 12/2019 | Bayer et al. |
| 2019/0390399 A1 | 12/2019 | Chase et al. |
| 2020/0024577 A1 | 1/2020 | Carlton et al. |
| 2020/0025672 A1 | 1/2020 | Scullin et al. |
| 2020/0055274 A1 | 2/2020 | Bayer et al. |
| 2020/0102530 A1 | 4/2020 | Winiski et al. |
| 2020/0120880 A1 | 4/2020 | Ross et al. |
| 2020/0128763 A1 | 4/2020 | Ross |
| 2020/0128816 A1 | 4/2020 | Thorvaldsdottir et al. |
| 2020/0131694 A1 | 4/2020 | Scullin et al. |
| 2020/0146224 A1 | 5/2020 | Kaplan-Bie et al. |
| 2020/0154752 A1 | 5/2020 | Akintoye et al. |
| 2020/0157506 A1 | 5/2020 | Bayer et al. |
| 2020/0196541 A1 | 6/2020 | Ross et al. |
| 2020/0208097 A1 | 7/2020 | Winiski |
| 2020/0221811 A1 | 7/2020 | Isse |
| 2020/0221812 A1 | 7/2020 | Isse |
| 2020/0239830 A1 | 7/2020 | O'Brien et al. |
| 2020/0270559 A1 | 8/2020 | Macur et al. |

(56) References Cited

U.S. PATENT DOCUMENTS

| | | | |
|---|---|---|---|
| 2020/0305486 A1 | 10/2020 | Akintoye et al. | |
| 2020/0362295 A1* | 11/2020 | Kozubal | C12N 1/145 |
| 2020/0392341 A1 | 12/2020 | Smith et al. | |
| 2020/0399824 A1 | 12/2020 | Stewart et al. | |
| 2021/0017486 A1 | 1/2021 | Kozubal et al. | |
| 2021/0059287 A1 | 3/2021 | Kozubal et al. | |
| 2021/0155893 A1 | 5/2021 | Kozubal et al. | |

FOREIGN PATENT DOCUMENTS

| | | |
|---|---|---|
| CN | 1416320 | 5/2003 |
| CN | 102782117 | 11/2012 |
| CN | 103080327 | 5/2013 |
| CN | 103393094 | 11/2013 |
| CN | 106613349 | 5/2017 |
| CN | 104480026 | 11/2017 |
| EP | 0006671 | 9/1982 |
| EP | 1133926 | 9/2001 |
| EP | 1094719 | 5/2003 |
| EP | 1612267 | 1/2006 |
| EP | 1623631 | 2/2006 |
| EP | 2719272 | 4/2014 |
| GB | 1356449 | 6/1974 |
| GB | 2148959 | 4/1987 |
| GB | 2165865 | 6/1987 |
| GB | 2188135 | 11/1989 |
| GB | 2199315 | 7/1991 |
| GB | 2375944 | 12/2002 |
| JP | H01-206970 | 8/1989 |
| JP | H08-504589 | 5/1996 |
| JP | H09-313168 | 12/1997 |
| JP | 2003-158920 | 6/2003 |
| JP | 2004-65165 | 3/2004 |
| JP | 2010-529832 | 9/2010 |
| JP | 2011-130766 | 7/2011 |
| KR | 101569282 | 11/2015 |
| SU | 1613492 | 12/1990 |
| SU | 1575552 | 1/1997 |
| WO | WO 89/12385 | 12/1989 |
| WO | WO 95/23843 | 9/1995 |
| WO | WO 98/51786 | 11/1998 |
| WO | WO 99/24555 | 5/1999 |
| WO | WO 02/089589 | 11/2002 |
| WO | WO 02/089604 | 11/2002 |
| WO | WO 03/012090 | 2/2003 |
| WO | WO 03/012095 | 2/2003 |
| WO | WO 03/012109 | 2/2003 |
| WO | WO 2004/052103 | 6/2004 |
| WO | WO 2005/053812 | 6/2005 |
| WO | WO 2006/003175 | 1/2006 |
| WO | WO 2006/086757 | 8/2006 |
| WO | WO 2006/096834 | 9/2006 |
| WO | WO 2006/119318 | 11/2006 |
| WO | WO 2007/055735 | 5/2007 |
| WO | WO 2007/140862 | 12/2007 |
| WO | WO 2008/021999 | 2/2008 |
| WO | WO 2008/083453 | 7/2008 |
| WO | WO 2010/032260 | 3/2010 |
| WO | WO 2010/042842 | 4/2010 |
| WO | WO 2010/053950 | 5/2010 |
| WO | WO 2016/049198 | 3/2016 |
| WO | WO 2016/063053 | 4/2016 |
| WO | WO 2017/151684 | 9/2017 |
| WO | WO 2018/002587 | 1/2018 |
| WO | WO 2019/008606 | 1/2019 |
| WO | WO 2019/067745 | 4/2019 |
| WO | WO 2019/099474 | 5/2019 |
| WO | WO 2020/102552 | 5/2020 |
| WO | WO 2021/124164 | 6/2021 |

OTHER PUBLICATIONS

U.S. Appl. No. 17/220,737, filed Apr. 1, 2021, Kozubal et al.
U.S. Appl. No. 17/323,918, filed May 18, 2021, Macur et al.
U.S. Appl. No. 17/323,931, filed May 18, 2021, Macur et al.
U.S. Appl. No. 17/410,853, filed Aug. 24, 2021, Stewart et al.
U.S. Appl. No. 17/410,856, filed Aug. 24, 2021, Stewart et al.
U.S. Appl. No. 17/410,864, filed Aug. 24, 2021, Stewart et al.
"Proteinogenic amino acid," Wikipedia, Jan. 4, 2019, 9 pages [retrieved online from: en.wikipedia.org/w/index.php?title=Proteinogenic_amino_acid&oldid=876841140].
"The Rennet Story: Animal, Vegetable and Microbial," Formaggio Kitchen, Feb. 4, 2013, 5 pages [retrieved online from: www.formaggiokitchen.com/blog/the-rennet-story-animal-vegetable-and-microbial].
Abe et al. "Anaerobic Elemental Sulfur Reduction by Fungus Fusarium oxysporum," Biosci. Biotechnol. Biochem., 2007, vol. 71, No. 10, pp. 2402-2407.
Aboul-Soud et al. "Transformation of Fusarium oxysporum by particle bombardment and characterisation of the resulting transformants expressing a GFP transgene," Mycopahologla, Dec. 2004, vol. 158, No. 4, pp. 475-482.
Agrahar-Murugkar et al. "Nutritional value of edible wild mushrooms collected from the Khasi hills of Meghalaya," Food Chemistry, 2005, vol. 89, pp. 599-603.
Akpinar-Bayizit, A. et al., "Single cell oil (SCO) production by Fusarium species using cheese whey as a substrate" Mljekarstvo, 2014, vol. 64, No. 2, pp. 111-118.
Alriksson et al. "Fish Feed From Wood," Cellulose Chemistry and Technology, 2014, vol. 48, pp. 843-848.
Awaad et al. "New Antifungal Compounds from Aspergillus terreus Isolated from Desert Soil," Phytotherapy Research, 2012, vol. 26, pp. 1872-1877.
Baker et al. "Antimicrobial activity of naphthoquinones from Fusaria," Mycopathogia, 1990, vol. 111, pp. 9-15.
Baker et al. "Novel Anthraquinones from Stationary Cultures of Fursarium oxysporum," Journal of Fermentation and Bioengineering, 1998, vol. 65, No. 4, pp. 359-361.
Beauvais et al. "An extracellular matrix glues together the aerial-grown hyphae of Aspergillus fumigatus," Cellular Microbiology, 2007, vol. 9, No. 6, pp. 1588-1600.
Bhatia et al. "Effect of Different Cultural Conditions on the Chemical Composition of Lipids of Fusarium oxysporum," Journal of the Science of Food and Agriculture, 1978, vol. 29, pp. 611-618.
Bligh et al. "A Rapid Method of Total Lipid Extraction and Purifiation," Canadian Journal of Biochemistry and Physiology, Aug. 1959, vol. 37, No. 8, pp. 911-917.
Bogale et al. "Characterization of Fusarium oxysporum isolates from Ethiopia using AFLP, SSR and DNA sequence analyses," Fungal Diversity, 2006, vol. 23, pp. 51-66.
Boominathan et al. "cAMP-mediated differential regulation of linin peroxidase and manganese-dependent peroxidase production in the white-rot basidiomycete Phanerochaete chrysosporium," Proc. Natl. Acad. Sci. USA, Jun. 1992, vol. 89, pp. 5586-5590.
Briggs "Widescale Biodiesel Production from Algae," University of New Hampshire (US) Biodiesel Group, Oct. 3, 2004, 7 pages [www.resillience.org/resillience-author/michael-briggs/].
Brimble et al., "Pyranonaphthoquinone antibiotics-isolation, structure and biological activity," Nat. Prod. Rep., 1999, vol. 16, pp. 267-281.
Cabrini et al. "Extraction of Lipids and Lipophilic Antioxidants from Fish Tissues: A Comparison Among Different Methods," Comp. Biochem. Physiol., 1992, vol. 101B, No. 3, pp. 383-386.
Cai et al. "Origin of Race 3 of *Fursarium oxysporum* f. sp. lycopersici at a Single Site in California," Phytopathology, 2003, vol. 93, No. 8, pp. 1014-1022.
Cenis "Rapid extraction of fungal DNA for PCR amplification," Nucleic Acids Research, 1992, vol. 20, No. 9, p. 2380.
Challis "A Widely Distributed Bacterial Pathway for Siderophore Biosynthesis Independent of Nonribosomai Peptide Synthetases," ChemBioChem, 2005, vol. 6, pp. 601-611.
Chisti "Biodiesel from microalgae," Biotechnology Advances, 2007, vol. 25, pp. 294-306.
Christakopoulos et al. "Direcet Conversion of Sorghum Carbohydrates to Ethanol by a Mixed Microbial Culture," Bioresource Technology, 1993, vol. 45, pp. 89-92.

(56) References Cited

OTHER PUBLICATIONS

Christakopoulos et al. "Direct Ethanol Conversion of Pretreated Straw by Fusarium oxysporum," Bioresource Technology, 1991, vol. 35, pp. 297-300.
Christakopoulos et al. "Direct fermentation of cellulose to ethanol by Fusarium oxysporum," Enzyme Microb. Technol., Apr. 1989, vol. 11, pp. 236-239.
Cooksey et al. "Fluorometric determination of the neutral lipid content of microalgal cells usilng Nile Red," Journal of Microbiological Methods, 1987, vol. 6, pp. 333-345.
Corcoran "Examining the efficacy of disinfectant products against an established S. enterica biofilm," Thesis Presented to the National University of Ireland, Galway for the Degree of Doctor of Philosophy, 2013, Ph.D. Thesis, vol. 1, Chapter 4, pp. 113-151.
Darouneh et al. "Citric acid production: Surface culture versus submerged culture," African Journal of Microbiology Research, Sep. 2009, vol. 3, No. 9, pp. 541-545.
Database WPI, Week 201149, Thomson Scientific, London, GB; AN 2011-H81056 XP002769954, -& JP 2011 130766 A (ROHM KK), Jul. 7, 2011, Abstract.
Daviere et al. "Potential Role of Transposable Elements in the Rapid Reorganization of the Fusarium oxysporum Genome," Fungal Genetics and Biology, 2001, vol. 34, pp. 177-192.
De La Broise et al. "Osmotic, Biomass, and Oxygen Effects on the Growth Rate of Fusarium oxysporum Using a Dissolved-Oxygen-Controlled Turbidostat," Biotechnology and Bioengineering, 1989, vol. 33, pp. 699-705.
Dey et al. "Comparative lipid profiling of two endophytic fungal isolates—*Colletotrichum* sp. and *Alternaria* sp. having potential utilities as biodiesel feedstock," Bioresource Technology, 2011, vol. 102, pp. 5815-5823.
Dinarvand et al. Effect of C/N Ratio and Media Optimization through Response Surface Methodology on Simultaneous Productions of Intra-and Extracellular Inulinase and Invertase from Aspergillus niger ATCC 20611, BioMed Research International (2013, vol. 2013, Article ID 508968, 13 pages.
Dowd et al. "Gene Expression Profile Changes in Cotton Root and Hypocotyl Tissues in Response to Infection with *Fusarium oxysporum* f. sp. *vasinfectum*," MPMI, 2004, vol. 17, No. 6, pp. 654-667.
El-Enshasy "Filamentous Fungal Cultures—Process Characteristics, Products, and Applications," Bioprocessing for Value-Added Products from Revewabie Resources, 2007, Chapter 9, Editor: Shang-Tian Yang, Elsevier, pp. 225-261.
Favela-Torres et al. "Kinetics of growth of Aspergillus niger during submerged, agar surface and solid state fermentations," Process Biochemistry, 1998, vol. 33, No. 2, pp. 103-107.
Ferreras et al. "Small-molecule inhibition of siderophore biosynthesis in *Mycobacterium tuberculosis* and Yersinia pestis," Nature Chemical Biology, Jun. 2005, vol. 1, No. 1, pp. 29-32.
Figueira et al. "Biosorption of Metals in Brown Seaweed Biomass," Wat. Res., 2000, vol. 34, No. 1, pp. 196-204.
Fisher et al. "Carnation Leaves as a Substrate and for Preserving Cultures of *Fusarium* species," Phytopathology, 1982, vol. 72, No. 1, pp. 151-153.
Fisher et al. "Taxonomic Importance of Microconidial Chains in Fusarium Section Liseola and Effects of Water Potential on Their Formation," Mycologia, 1983, vol. 75, No. 4, pp. 693-698.
Folch et al. "A Simple Method for the Isolation and Purification of Total Lipides from Animal Tissues," J. Biol. Chem., 1957, vol. 226, pp. 497-509.
Gibbs et al. "Growth of Filamentous Fungi in Submerged Culture: Problems and Possible Solutions," Critical Reviews in Biotechnology, 2000, vol. 20, No. 1, pp. 17-48.
Gilson et al. "Calcium Alginate Bead Manufacture: With and Without Immobilised Yeast. Drop Formation at a Two-Fluid Nozzle," J. Chem. Tech. Biotechnol., 1995, vol. 62, pp. 227-232.
Gogoi et al. "Optimization of process parameters for improved production of bioactive metabolite by a novel endophytic fungus *Fusarium* sp. DF2 isolated from Taxus wallichiana of North East India," World Journal of Microbiology and Biotechnology, 2008, vol. 94, pp. 79-87.
Gong et al. "Efficient conversion of biomass into lipids by using the simultaneous saccharification and enhanced lipid production process," Biotechnology for Biofuels, 2013, vol. 6, 12 pages.
Gong et al. "Lipid production from corn stover by the oleaginous yeast *Cryptococcus curvatus*," Biotechnology for Biofuels, 2014, vol. 7, 9 pages.
Graham et al. "Factors Affecting Production of Mold Mycelium and Protein in Synthetic Media," Applied and Environmental Microbiology, Sep. 1976, vol. 32, No. 3, pp. 381-387.
Grewal et al. "Fungal Production of Citric Acid," Biotechnology Advances, 1995, vol. 13, No. 2, pp. 209-234.
Griffin et al. "Volatile organic compound production by organisms in the genus *Ascocoryne* and a re-evaluation of myco-diesel production by NRRL 50072," Microbiology, 2010, vol. 156, pp. 3814-3829.
Gross et al., "Acidophilic and acid-tolerant fungi and yeasts," Hydrobiologia, 2000, vol. 433, pp. 91-109.
Gunner et al. "Anaerobic Growth of Fusarium Oxysporum," Journal of Bacteriology, Jun. 1964, vol. 87, No. 6, pp. 1309-1316.
Gutierrez-Correa et al. "Surface adhesion fermentation: a new fermentation category Fermentacion por adhesion a superficies: una nuewva categoria fermentativa," Rev. Peru. Biol. 2003, vol. 10, No. 2, pp. 113-124.
Hailei et al. "Overproduction of a potential red pigment by a specific self-immobilization biomembrane-surface liquid culture of penicillium novae-zeelandiae," Bioprocess Biosyst. Eng., 2012, vol. 35, pp. 1407-1416.
Hallenbeck et al. "Advances in fermentative biohydrogen production: the way forward?" Trends in Biotechnology, 2009, vol. 27, No. 5, pp. 287-297.
Hara et al. "Lipid Extraction of Tissues with a Low-Toxicity Solvent," Analytical Biochemistry, 1978, vol. 90, pp. 420-426.
Hasegan et al. "Growth and Survival of Colored Fungi in Space (CFS-A)," Expeditions 25-28, Dec. 7, 2016, 4 pages [www.nasa.gov/mission_pages/station/research/experiments/636.html].
Hendriks et al. "Pretreatments to enhance the digestibility of lignocellulosic biomass," Bioresource Technology, 2009, vol. 100, pp. 10-18.
Horowitz et al. "Isolation and Identification of the Conidial Germination Factor of Neurospora crassa," Journal of Bacteriology, Jul. 1976, vol. 127, No. 1, pp. 135-140.
Hua-Van et al. "Genome organization in Fusarium oxysporum: clusters of class II transoposons," Curr. Genet., 2000, vol. 37, pp. 339-347.
Hui et al. "Direct microbial conversion of wheat straw into lipid by a cellulolytic fungus of Aspergillus oryzae A-4 in solid-state fermentation," Bioresource Technology, 2010, vol. 101, pp. 7556-7562.
Imanaka et al. "Cultivation characteristics and gene expression profiles of Aspergillus oryzae by membrane-surface liquid culture, shaking-flask culture, and agar-plate culture," Journal of Bioscience and Bioengineering, 2010, vol. 109, No. 3, pp. 267-273.
Inskeep et al. "On the energetics of chemolithotrophy in nonequilibrium systems: case studies of geothermal springs in Yellowstone National Park," Geobiology, 2005, vol. 3, pp. 297-317.
Jannotia "MSU graduate launches biofuels start-up, partners with university," MSU News Service, Feb. 15, 2013, 2 pages [retrieved online on Oct. 5, 2015 from: www.montana.edu/news/11756/msu-graduate-launches-biofuels-start-up-partners-with-university].
Jiang et al., "A New Approach to Manufacturing Biocomposite Sandwich Structures: Mycelium-Based Cores," Proceedings of the ASME 2016 International Manufacturing Science and Engineering Conference (MSEC2016), Jun. 27-Jul. 1, 2016, Blacksburg, Virginia, USA, 12 pages.
Joshi et al. "The Influence of Various Carbon and Nitrogen Sources on Oil Production by Fusarium oxysporum," Folia Microbiol., 1987, vol. 32, pp. 124-129.
Kazuhiro et al. "Membrane-Surface Liquid Culture, Fungi," Encyclopedia of Industrial Biotechnology: Bioprocess, Bioseparation, and Cell Technology, 2009, John Wiley & Sons, Inc., pp. 1-7.

(56) References Cited

OTHER PUBLICATIONS

Kendall "Company receives grant to turn waste into products," Bozeman Daily Chronicle, Mar. 27, 2016, 2 pages [retrieved online from: www.bosemandailychronicle.com/news/economy/company-receives-grant-to-turn-waste-into-products/article_2daf4dd4-52c7-5e4d-8402-a0b0887ed77e.html].

Kerem et al. "Effect of Manganese on Preferential Degradation of Lignin by Pleurotus ostreatus during Solid-State Fermentation," Applied and Environmental Microbiology, Aug. 1995, vol. 61, No. 8, pp. 3057-3062.

Khang et al. "A dual selection based, targeted gene replacement tool for Magnaporthe grisea and Fusarium oxysporum," Fungal Genetics and Biology, 2005, vol. 42, pp. 483-492.

Kimura "Natural Products and Biological Activity of the Pharmacologically Active Cauliflower Mushroom Sparassis crispa," BioMed Research International, vol. 2013, Article ID 982317, 10 pages.

King "Supercritical Fluid Extraction: Present Status and Prospects," Grasas y Aceites, 2002, vol. 53, Fasc. 1, pp. 8-21.

Kivrak et al. "Free amino acid profiling in the giant puffball mushroom (*Calvatia gigantea*) using UPLC-MS/MS," Food Chemistry, 2014, vol. 158, pp. 88-92.

Klinke et al. "Inhibition of ethanol-producing yeast and bacteria by degradation products produced during pre-treatment of biomass," Applied Microbiology and Biotechnology, 2004, vol. 66, pp. 10-26.

Klotz et al. "A Medium for Enhancement of Chlamydospore Formation in *Fusarium* Species," Mycologia, 1988, vol. 80, pp. 108-109.

Kozubal et al. "Isolation and Distribution of a Novel Iron-Oxidizing Crenarchaeon from Acidic Geothermal Springs in Yellowstone National Park," Applied and Environmental Microbiology, Feb. 2008, vol. 74, No. 4, pp. 942-949.

Kramer et al. "A comparison of procedures to determine free fatty acids in rat heart," Journal of Lipid Research, 1978, vol. 19, pp. 103-106.

Kratochvil et al. "Multicomponent Biosorption in Fixed Beds," Wat. Res., 2000, vol. 34, No. 12, pp. 3186-3196.

Kratochvil et al. "Optimizing Cu Removal/Recovery in a Biosorption Column," Wat. Res., 1997, vol. 31, No. 9, pp. 2327-2339.

Lekha eta l. "Comparative Titres, Location and Properties of Tannin Acyl Hydrolase Produced by Aspergillus niger PKL 104 in Solid-State, Liquid Surface and Submerged Fermentations," Process Biochemistry, 1994, vol. 29, No. 6, pp. 497-503.

Lezinou et al. "Simultaneous Saccharification and Fermentation of Sweet Sorghum Carbohydrates to Ethanol in a Fed-Batch Process," Biotechnology Letters, Sep. 1994, vol. 16, No. 9, pp. 983-988.

Li et al. "Perspectives of microbial oils for biodiesel production," Appl Microbiol Biotechnol, 2008, vol. 80, pp. 749-756.

Lin et al. "Ethyl Acetate/Ethyl Alcohol Mixtures as an Alternative to Folch Reagent for Extracting Animal Lipids," Journal of Agricultural and Food Chemistry, 2004, vol. 52, pp. 4984-4986.

Lin et al. "Mixed culture fermentation from lignocellulosic materials using thermophilic lignocellulose-degrading anaerobes," Process Biochemistry, Feb. 2011, vol. 46, No. 2, pp. 489-493.

Liu et al. "Identification of the Characteristics for Forma Specials of Fusarium oxysporum Schl. Based on the Analysis of Fatty Acid Biomarkers," Scientia Agricultura Sinica, Dec. 2012, vol. 45, No. 24, pp. 4998-5012 (English abstract).

Lynd et al. "Metabolism of H2-CO2, Methanol, and Glucose by Butyribacterium methylotrophicum," Journal of Bacteriology, Mar. 1983, vol. 153, No. 3, pp. 1415-1423.

Madhosingh "Sterol and Fatty Acid Metabolism in Fusarium oxysporum," Agric. Biol. Chem., 1977, vol. 41, No. 7, pp. 1233-1238.

Mallette et al. "Resolution of volatile fuel compound profiles from Ascocoryne sarcoides: a comparison by proton transfer reaction-mass spectrometry and solid phase microextraction gas chromatography-mass spectrometry," AMB Express, 2012, vol. 2, 13 pages.

Matsumoto "Comparison of two fatty acid analysis protocols to characterize and differentiate *Fusarium oxysporum* f. sp. *lycopersici* and *F. oxysporum* f. sp. *radicis-lycopersici*," Mycoscience, Aug. 2006, vol. 47, No. 4, pp. 190-197.

May et al. "Semi-Plant Scale Production of Gluconic Acid by Mold Fermentation," Industrial and Engineering Chemistry, Dec. 1929, vol. 21, No. 12, pp. 1198-1203.

Mazur "Mechanical Properties of Sheets Comprised of Mycelium: A Paper Engineering Perspective," SUNY College of Environmental Science and Forestry, 2015, Honors Thesis, Paper 68, 39 pages.

McFadden et al. "Fusarium wilt (*Fusarium oxysporum* f. sp. *vasinfectum*) genes expressed during infection of cotton (*Gossypium hirsutum*)," Molecular Plant Pathology, 2006, vol. 7, No. 2, pp. 87-101.

Meng et al. "Biodiesel production from oleaginous microorganisms," Renewable Energy, 2009, vol. 34, pp. 1-5.

Merlin et al. "Optimization of Growth and Bioactive Metabolite Production: Fusarium Solani," Asian Journal of Pharmaceutical and Clinical Research, 2013, vol. 6, Suppl. 3, pp. 98-103.

Merrill et al. "Lipids and Lipid-Like Compounds of Fusarium," Lipids of Pathogenic Fungi, 1996, CRC Press, Chapter 9, pp. 200-217.

Miethke et al. "Siderophore-Based Iron Acquisition and Pathogen Control," Microbiology and Molecular Biology Reviews, Sep. 2007, vol. 71, No. 3, pp. 413-451.

Mohsen et al. "The effect of some environmental conditions on the growth and activity of the external enzymes for five sp. Of *Fusarium*," Journal of Babylon University/Pure and Applied Sciences, 2016, vol. 24, No. 3, pp. 630-646.

Moran "Biofuel Production Using and Acidophilic Fungus," MSU Student Research Celebration, Mar. 5, 2013, 1 page [retrieved online on Oct. 5, 2015 from: scholarworks.montana.edu/xmlui/handle/1/500].

Moyer "Effect of Alcohols on the Mycological Production of Citric Acid in Surface and Submerged Culture," Applied Microbiology, 1953, vol. 1, No. 1, pp. 7-13.

Mullins et al. "Agrobacterium-Mediated Transformation of Fusarium oxysporum: An Efficeint Tool for Insertional Mutagenesis and Gene Transfer," Phytopathology, 2001, vol. 91, No. 2, pp. 173-180.

Naim et al. "Production of Lipids and Sterols by Fusarium oxysporum (Schlecht). Utilization of Some Agro-Industrial By-products as Additives and Basal Medium," Agricultural Wastes, 1985, vol. 14, pp. 207-220.

Naqvi et al. "Production of Lipids by Fermentation Preliminary Report," Journal of Islamic Academy of Sciences, 1997, vol. 10, No. 1, pp. 13-18.

Narayanamurthy et al. "Comparative Studies on Submerged, Liquid Surface and Solid State Fermentation for Citric Acid Production by Aspergillus Niger RCNM 17," Aslan Journal of Microbol. Biotech. Env. Sc., 2008, vol. 10, No. 2, pp. 361-364.

Neilands "A Crystalline Organo-iron Pigment from a Rust Fungus (*Ustilago sphaerogena*)," J. Am. Chem. Soc., Oct. 1952, vol. 74, pp. 4846-4847.

Neilands "Microbial Iron Compounds," Ann. Rev. Biochem., 1981, vol. 50, pp. 715-731.

Neilands "Siderophores: Structure and Function of Microbial Iron Transport Compounds," The Journal of Biological Chemistry, 1995, vol. 270, No. 45, pp. 26723-26726.

Nelson et al. "Taxonomy, Biology, and Clinical Aspects of Fusarium Species," Clinical Microbiology Review, Oct. 1994, vol. 7, No. 4, pp. 479-504.

Nishimura "Selective media for Fusarium oxysporum," J. Gen. Plant Pathol., 2007, vol. 73, pp. 342-348.

Norregaard et al. "Filamentous Fungi Fermentation," Industrial Scale Suspension Cultrue of Living Cells, 2014, Wiley-VCH Verlag GmbH & Co., KGaA, pp. 130-162.

Oda et al. "Liquid-surface immobilization system and liquid-liquid interface bioreactor: Application to fungal hydrolysis," Process Biocehmistry, 2007, vol. 42, pp. 1553-1560.

Ogawa et al. "Production of Neutral Protease by Membrane-Surface Liquid Culture of Aspergillus orzyae IAM2704," Journal of Fermentation and Bioengineering, 1995, vol. 80, No. 1, pp. 35-40.

Oostra et al. "Intra-Particle Oxygen Diffusion Limitation in Solid-State Fermentation," Biotechnology and Bioengineering, Oct. 2001, vol. 75, No. 1, pp. 13-24.

(56) References Cited

OTHER PUBLICATIONS

Palmqvist et al. "Fermentation of lignocellulosic hydrolysates. II: inhibitors and mechanisms of inhibition," Bioresource Technology, 2000, vol. 74, pp. 25-33.
Panagiotou et al. "Simultaneous saccharification and fermentation of cellulose by Fusarium oxysporum F3-growth characteristis and metabolite profiling," Enzyme and Microbial Technology, 2005, vol. 36, pp. 693-699.
Papanikolaou et al. "Single cell oil (SCO) production by Morteirella isabellina grown on high-sugar content media," Bioresource Technology, 2004, vol. 95, pp. 287-291.
Park et al. "Multi-Stage Biofilm reactor for Acetic Acid Production at High Concentration," Biotechnology Letters, Jul. 1992, vol. 14, No. 7, pp. 609-612.
Pavko et al. "Comparison of Surface and Submerged Modes of Cultivation for Biomass Production of Fungus Rhizopus stolonifer," Chem. Biocehm. Eng. Q. 1996, vol. 10, No. 3, pp. 119-123.
Pawlak "A Survey of Standards for the U.S. Fiber/Textile/Apparel Industry," U.S. Department of Commerce, Apr. 1996, NISTIR 5823, pp. 22, 23, 27, 61 and 80.
Pinzi et al. "The Ideal Vegetable Oil-based Biodiesel Composition: A Review of Social, Economical and Technical Implications," Energy & Fuels, 2009, vol. 23, pp. 2325-2341.
Powell et al. "In Vivo Rearrangement of Foreign DNA by Fusarium oxysporum Produces Linear Self-Replicating Plasmids," Journal of Bacteriology, Jun. 1990, vol. 172, No. 6, pp. 3163-3171.
Rahardjo, "Fungal Mats in Solid-State Fermentation," Thesis, Apr. 18, 2005, 164 pages.
Rahardjo et al. "Contribution of Aerial Hyphae of Aspergillus oryzae to Respiration in a Model Solid-State Fermentation System," Biotechnology and Bioengineering, Jun. 2002, vol. 78, No. 5, pp. 539-544.
Renshaw et al. "Fungal siderophores: structures, functions and applications," Mycol. Res., Oct. 2002, vol. 106, No. 10, pp. 1123-1142.
Roosenberg II et al. "Studies and Syntheses of Siderophores, Microbial Iron Chelators, and Analogs as Potential Drug Delivery Agents," Current Medicinal Chemistry, 2000, vol. 7. pp. 159-197.
Ruan et al. "Co-Hydrolysis of Lignocellulosic Biomass for Microbial Lipid Accumulation," Biotechnology and Bioengineering, Apr. 2013, vol. 110, No. 4, pp. 1039-1049.
Ruiz et al. "Sugar fermentation by Fusarium oxysporum to produce ethanol," World J. Microbiol Biotechnol, 2007, vol. 23, pp. 259-267.
Sanchez-Rangel et al. "Environmental pH modulates transcriptomic responses in the fungus *Fusarium* sp. Associated with KSHB *Euwailacea* sp. Near fomicatus," BMC Genomics, 2018, vol. 19, 721, 21 pages.
Sankpal et al. "Nitrogen-Dependent Regulation of Gluconic and/or Citric Acid Production by Aspergillus niger," Journal of Microbiology and Biotechnology, 2000, vol. 10, No. 1, pp. 51-55.
Sciarini et al., "Concerning the Relation Between Structure and Action of Xanthones on Dehydrogenations by Fusaria," Proceedings of the National Academy of Sciences of the United States of America, vol. 29, No. 3-4, Mar. 15, 1943, pp. 121-126.
Seo et al. "Measurement of ethanol concentration using solvent extraction and dichromate oxidation and itss application to bioethanol production process," J Ind Microbiol Biotechnol, 2009, vol. 36, No. 285-292.
Sergeeva et al. "Lipids of Filamentous Fungi as a Material for Producing Biodiesel Fuel," Applied Biochemistry and Microbiology, 2008, vol. 44, No. 5, pp. 523-527.
Shah et al. "Comparative Profiles of Fungal Alpha Amylase Production by Submerged and Surface Fermentation," Biotechnology Letters, 1991, vol. 13, No. 5, pp. 361-364.
Singh et al. "Direct Fermentation of Cellulosic Materials by Fusarium Oxysporum 841: Acetic Acid/Ethanol Production and Tolerance," J. Gen. Appl. Microbiol., 1992, vol. 38, pp. 227-236.
Smith "An Overview of Ecological and Habitat Aspects in the Genus *Fusarium* with Special Emphasis on the Soil-Borne Pathogenic Forms," Plant Pathology Bulletin, 2007, vol. 16, pp. 97-120.
Somashekar et al. "Efficacy of extraction methods for lipid and fatty acid composition from fungal cultures," World Journal of Microbiology & Biotechnology, 2001, vol. 17, pp. 317-320.
Srivastava et al., "Identification of Limiting Factors for the Optimum Growth of Fusarium Oxysporum in Liquid Medium," Toxicol. Int., 2011, vol. 18(2), pp. 111-116.
Stamets "Notes on Nutritional Properties of Culinary-Medicinal Mushrooms," International Journal of Medicinal Mushrooms, 2005, vol. 7, pp. 103-110.
Starkey "Effect on pH on Toxicity of Copper to *Scytalidium* sp., a Copper-tolerant Fungus, and Some Other Fungi," Journal of General Microbiology, 1973, vol. 78, pp. 217-225.
Tanaka et al. "Production of laccase by membrane-surface liquid culture of Trametes versicolor using a poly(L-lactic acid) membrane," Biochemical Engineering Journal, 2007, vol. 33, pp. 188-191.
Tatum et al. "Naphthofurans Produced by Fusarium Oxysporum Isolated from Citrus," Phytochemistry, 1987, vol. 26, No. 9, pp. 2499-2500.
Tatum et al. "Naphthoquinones Produced by Fusarium Oxysporum Isolated from Citrus," Phytochemistry, 1985, vol. 24, No. 3, pp. 457-459.
Teunissen et al. "A Near-Isogenic *Fusarium oxysporum* f. sp. Lycopersici Strain with a Novel Combination of Avirulence Characteristics," Phytopathology, 2003, vol. 93, No. 11, pp. 1361-1367.
Thomas et al. "Employing Central Composite Design for Evaluation of Biomass Production by Fusarium venenatum In Vivo Antioxidant and Antihyperlipidemic Properties," Applied Biochemistry and Biotechnology, 2017, vol. 183, No. 1, pp. 91-109 (ABSTRACT only).
Trujillo et al. "Mathematically Modelling the Removal of Heavy Metals from a Wastewater Using Immobilized Biomass," Environ. Sci. Technol., 1991, vol. 25, No. 9, pp. 1559-1565.
Tsakali et al. "A review on whey composition and the methods used for its utilization for food and pharmaceutical products," Conference: 6th International Conference on Simulation and Modelling in the Food and Bio-Industry FOODSIM 2010, At CIMO Research Centre, Braganca, Portugal, 8 pages.
Tsezos et al. "An Investigation of Engineering Parameters for the Use of Immobilized Biomass Particles in Biosorption," J. Chem. Tech. Biotechnol., 1990, vol. 48, pp. 29-39.
Tyagi et al. "Effect of different pH on the growth and sporulation of Fusarium oxysporum: The causal organism of wilt disease of Tomato," International Journal of Basic and Applied Biology, Oct. 2014, vol. 2, No. 1, pp. 103-106.
Ulziijargal et al. "Nutrient Compositions of Culinary-Medicinal Mushroom Fruiting Bodies and Mycelia," International Journal of Medicinal Mushrooms, 2011, vol. 13, No. 4, pp. 343-349.
Vaccarino et al. "SCP from Orange Peel by Fermentation with Fungi-Submerged and 'Surface' Fermentations," Biological Wastes, 1989, vol. 29, pp. 279-287.
Van Leeuwen et al. "Fungal Treatment of Crop Processing Wastewaters with Value-Added Co-Products," Sustainable Bioenergy and Bioproducts, 2012, pp. 13-44.
Vinson et al., "The Nutritive Value of Fusaria," Science, vol. 101, No. 2624, dated Apr. 13, 1945, pp. 388-389.
Watanabe "Wettability of ceramic surfaces—A wide range control of surface wettability from super hydrophilicity to super hydrophobicity, from static wettability to dynamic wettability," Journal of the Ceramic Society of Japan, 2009, vol. 117, No. 12, pp. 1285-1292, pp. 1285.
Weber et al. "A microbial consortium involving the astaxanthin producer Xanthophyllomyces dendrorhous on freshly cut birch stumps in Germany," Mycologist, 2j006, vol. 20, pp. 57-61.
White et al., "Bioconversion of brewer's spent grains to bioethanol," FEMS Yeast Res, 2008, vol. 8, No. 7, pp. 1175-1184.
Whitely et al. "Lipid peroxidation in liver tissue specimens stored at subzero temperatures," Cyro-Letters, 1992, vol. 13, pp. 83-86.

(56) References Cited

OTHER PUBLICATIONS

Wiebe "Myco-protein from Fusarium venenatum: a well-established product for human consumption," Appl Microbiol Biotechnol, 2002, vol. 58, pp. 421-427.

Wiebe et al. "Quorn™ Myco-protein—Overview of a successful fungal product," Mycologist, Feb. 2004, vol. 18, No. 1, pp. 17-20.

Wucherpfennig et al. "Morphology engineering—Osmolality and its effect on Aspergillus niger morphology and productivity," Microbial Cell Factories, 2011, vol. 10:58, 15 pages.

Xie et al. "Enzymatic hydrolysates of corn stover pretreated by a N-methylpyrralidone-ionic liquid solution for microbial lipid production," Green Chemistry, 2012, vol. 14, pp. 1202-1210.

Xiros et al. "Enhanced ethanol production from brewer's spent grain by a Fusarium oxysporum consolidated system," Biotechnology for Biofuels, 2009, vol. 2, No. 4, 12 pages.

Xiros et al. "Evaluation of Fusarium oxysporum as an enzyme factory for the hydrolysis of brewer's spent grain with improved biodegradability for ethanol production," Industrial Crops and Products, 2008, vol. 28, pp. 213-224.

Zhou et al. "Multi-Energy Metabolic Mechanisms of the Fungus *Fusarium oxysporum* in Low Oxygen Environments," Bioscience, Biotechnology, and Biochemistry, 2010, vol. 74, No. 12, pp. 2431-2437.

International Search Report and Written Opinion for International (PCT) Patent Application No. PCT/US20/38194, dated Dec. 4, 2020 27 pages.

Dhillon et al., "Green synthesis approach: extraction of chitosan from fungus *mycelia*," Critical Reviews in Biotechnology, vol. 33, No. 4, Dec. 2013, DD. 379-403.

Shakir et al., "The Effect of Crosslinking Fibers with Polyvinyl Alcohol Using Citric Acid," Imperial Journal of Interdisciplinary Search, vol. 3, No. 4, 2017, pp. 758-764.

Ma et al., "Preparation and characteristics of biodegradable mulching films based on fermentation industry wastes," International Biodeterioration and Biodegradation, vol. 111, Apr. 28, 2016, pp. 54-61.

Official Action for U.S. Patent No. U.S. Appl. No. 17/410,853, dated Jun. 14, 2022, 10 pages.

\* cited by examiner

FUNGAL TEXTILE MATERIALS AND LEATHER ANALOGS

CROSS-REFERENCE TO RELATED APPLICATIONS

This application is a divisional of U.S. patent application Ser. No. 17/030,322, filed 23 Sep. 2020, which is a continuation of U.S. patent application Ser. No. 16/904,520, filed 17 Jun. 2020, which claims the benefit of priority of U.S. Provisional Patent Applications 62/862,680, filed 18 Jun. 2019; 62/951,332, filed 20 Dec. 2019; and 62/966,525, filed 27 Jan. 2020. All of the above-referenced applications are incorporated by reference herein in their entireties.

FIELD OF THE INVENTION

This invention relates generally to fungal materials, and particularly to materials derived from filamentous fungi that can be used as leather analogs and in other textiles and fabrics.

BACKGROUND OF THE INVENTION

Many current textile materials, including but not limited to leather, create environmental problems during manufacturing and may be difficult or impossible to recycle or dispose of in an environmentally safe way at the end of an article's useful life. By way of non-limiting example, the manufacture of leather depends on the rearing of cattle (which has a significant environmental impact in itself and may raise animal welfare concerns) and requires a tanning step, which may use highly toxic chemicals such as chromium, formic acid, mercury, and various solvents. Leather also biodegrades slowly, over times of about 25 to about 40 years. Many textile materials suffer from similar environmental or ethical concerns.

There is thus a need in the art for textile materials that may be produced cost-effectively with a minimum of environmental impact and without animal welfare or other ethical concerns. It is further advantageous for such materials to retain various physical and/or mechanical properties, e.g. tensile strength, tear strength, flexural rigidity, elasticity, texture, thermal properties, sensory attributes, etc., of conventional textile materials, e.g. leather.

SUMMARY OF THE INVENTION

In one aspect of the present invention, a method for preparing a durable sheet material comprising fungal biomass comprises (a) causing a solution to infiltrate an inactivated fungal biomass, the solution comprising a solvent and a component selected from the group consisting of a polymer, a crosslinker, and combinations and mixtures thereof; and (b) curing the biomass to remove solvent from the biomass and form the durable sheet material.

In embodiments, the fungal biomass may comprise fungal mycelia.

In embodiments, the inactivated fungal biomass may be size-reduced prior to step (a) and step (a) may comprise blending the size-reduced inactivated fungal biomass with the solution to form a blended composition. The method may, but need not, further comprise, casting the blended composition to form a cast sheet from which solvent is removed in step (b). The size-reduced inactivated fungal biomass may, but need not, have an average particle size of no more than about 125 microns.

In embodiments, the inactivated fungal biomass may comprise a cohesive fungal biomass and (a) may comprise agitating the inactivated fungal biomass and the solution together for a time period. The cohesive fungal biomass may, but need not, be produced by a surface fermentation process or a submerged solid surface fermentation process. The time period may, but need not, be selected from the group consisting of at least about 4 hours, at least about 5 hours, at least about 10 hours, at least about 15 hours, at least about 20 hours, or at least about 25 hours. The time period may, but need not, be between about 10 hours and about 20 hours. The agitating may, but need not, be carried out at a pressure other than atmospheric pressure, which may be sub-atmospheric pressure or super-atmospheric pressure. The method may, but need not, further comprise subjecting the inactivated fungal biomass to treatment with at least one chemical selected from the group consisting of calcium hydroxide and tannins.

In embodiments, the inactivated fungal biomass may comprise a fungal paste produced by submerged fermentation.

In embodiments, the polymer may be selected from the group consisting of polyvinyl alcohol, chitosan, polyethylene glycol, alginates, starches, polycaprolactones, polyacrylic acids, hyaluronic acid, and combinations thereof.

In embodiments, the polymer may be present in the durable sheet material in an amount selected from the group consisting of no more than about 25 wt % of the durable sheet material, no more than about 20 wt % of the durable sheet material, no more than about 15 wt % of the durable sheet material, no more than about 10 wt % of the durable sheet material, and no more than about 5 wt % of the durable sheet material.

In embodiments, the crosslinker may be selected from the group consisting of citric acid, tannic acid, suberic acid, adipic acid, succinic acid, extracted vegetable tannins, glyoxal, and combinations thereof.

In embodiments, the solution may further comprise a plasticizer. The plasticizer may, but need not, be selected from the group consisting of glycerol and esters thereof, polyethylene glycol, citric acid, oleic acid, oleic acid polyols and esters thereof, epoxidized triglyceride vegetable oils, castor oil, pentaerythritol, fatty acid esters, carboxylic ester-based plasticizers, trimellitates, adipates, sebacates, maleates, biological plasticizers, and combinations thereof.

In embodiments, the fungal biomass may comprise at least one filamentous fungus belonging to an order selected from the group consisting of Ustilaginales, Russulales, Agaricales, Pezizales, and Hypocreales.

In embodiments, the fungal biomass may comprise at least one filamentous fungus belonging to a family selected from the group consisting of Ustilaginaceae, Hericiaceae, Polyporaceae, Grifolaceae, Lyophyllaceae, Strophariaceae, Lycoperdaceae, Agaricaceae, Pleurotaceae, Physalacriaceae, Omphalotaceae, Tuberaceae, Morchellaceae, Sparassidaceae, Nectriaceae, and Cordycipitaceae.

In embodiments, the fungal biomass may comprise at least one filamentous fungus belonging to a genus selected from the group consisting of *Agaricus, Calocybe, Calvatia, Cordyceps, Disciotis, Fomes, Fusarium, Ganoderma, Grifola, Hericulum, Hypholoma, Hypsizygus, Morchella, Pholiota, Pleurotus, Polyporous, Sparassis, Stropharia, Tuber,* and *Ustilago.*

In embodiments, the fungal biomass may comprise at least one filamentous fungus selected from the group consisting of *Ustilago esculenta, Hericulum erinaceus, Polyporous squamosus, Grifola fondosa, Hypsizygus mar-*

*moreus, Hypsizygus ulmarius, Calocybe gambosa, Pholiota nameko, Calvatia gigantea, Agaricus bisporus, Stropharia rugosoannulata, Hypholoma lateritium, Pleurotus eryngii, Pleurotus ostreatus, Pleurotus ostreatus* var. *columbinus, Tuber borchii, Morchella esculenta, Morchella conica, Morchella importuna, Sparassis crispa, Fusarium venenatum,* MK7 ATCC Accession Deposit No. PTA-10698, *Disciotis venosa,* and *Cordyceps militaris.*

In embodiments, the solution may further comprise at least one of a pigment, a solubilizer, and a pH adjusting agent. The solubilizer may, but need not, be selected from the group consisting of hydrochloric acid, acetic acid, formic acid, lactic acid, and combinations and mixtures thereof. The pH adjusting agent may, but need not, be selected from the group consisting of hydrochloric acid, acetic acid, formic acid, lactic acid, and combinations and mixtures thereof.

In embodiments, the durable sheet material may comprise proteins crosslinked with isopeptide bonds.

In embodiments, the method may further comprise at least one of (i) adding a thermal dopant to the inactivated fungal biomass and (ii) adding a thermal dopant to the durable sheet material after step (b). An amount of the thermal dopant may, but need not, be selected from the group consisting of at least about 2.5 wt % of the durable sheet material, at least about 5 wt % of the durable sheet material, at least about 7.5 wt % of the durable sheet material, at least about 10 wt % of the durable sheet material, at least about 12.5 wt % of the durable sheet material, at least about 15 wt % of the durable sheet material, and at least about 17.5 wt % of the durable sheet material. An amount of the thermal dopant may, but need not, be selected from the group consisting of no more than about 20 wt % of the durable sheet material, no more than about 17.5 wt % of the durable sheet material, no more than about 15 wt % of the durable sheet material, no more than about 12.5 wt % of the durable sheet material, no more than about 10 wt % of the durable sheet material, no more than about 7.5 wt % of the durable sheet material, and no more than about 5 wt % of the durable sheet material. The thermal dopant may, but need not, be selected from the group consisting of a ceramic material, a metallic material, a polymeric material, and combinations thereof. The thermal dopant may, but need not, be selected from the group consisting of activated charcoal, aluminum oxide, bentonite, diatomaceous earth, ethylene vinyl acetate, lignin, nanosilica, polycaprolactone, polylactic acid, silicone, and yttrium oxide.

In embodiments, the inactivated fungal biomass may be a size-reduced inactivated fungal biomass.

In embodiments, the inactivated fungal biomass may comprise a biomat, or portion thereof, produced by a surface fermentation process. A carbon-to-nitrogen molar ratio in a growth medium of the surface fermentation process may, but need not, be between about 5 and about 20, or between about 7 and about 15.

In another aspect of the present invention, a textile composition comprises an inactivated fungal biomass; and at least one component selected from the group consisting of a plasticizer, a polymer, a crosslinker, and a dye, wherein the at least one component is distributed in the fungal mycelial biomass.

In embodiments, the textile composition may have a thickness of at least about 1 mm.

In embodiments, the textile composition may have a tear force of at least about 30 N.

In embodiments, the textile composition may have a tear strength of at least about 10 N/mm.

In embodiments, the textile composition may have a flexural rigidity of no more than about 5 gram-centimeters.

In embodiments, the textile composition may have a tensile strength of at least about 10 MPa.

In embodiments, the textile composition may have a water spotting grey scale rating of at least about 3.

In embodiments, the textile composition may have a light color fastness blue wool rating of at least about 4.

In embodiments, the textile composition may have a rub color fastness grey scale rating, when dry, of at least about 3.

In embodiments, the textile composition may have a rub color fastness grey scale rating, when wet, of at least about 2.

In embodiments, the textile composition may further comprise at least one backing layer of a non-fungal textile material. The non-fungal textile material may, but need not, be selected from the group consisting of an acrylic textile, an alpaca textile, an angora textile, a cashmere textile, a coir textile, a cotton textile, an eisengarn textile, a hemp textile, a jute textile, a Kevlar textile, a linen textile, a microfiber textile, a mohair textile, a nylon textile, an olefin textile, a pashmina textile, a polyester textile, a piña textile, a ramie textile, a rayon textile, a sea silk textile, a silk textile, a sisal textile, a spandex textile, a spider silk textile, a wool textile, and combinations and mixtures thereof.

In embodiments, the textile composition may further comprise a thermal dopant. T thermal dopant may, but need not, be selected from the group consisting of a ceramic material, a metallic material, a polymeric material, and combinations and mixtures thereof. The thermal dopant may, but need not, be selected from the group consisting of activated charcoal, aluminum oxide, bentonite, diatomaceous earth, ethylene vinyl acetate, lignin, nanosilica, polycaprolactone, polylactic acid, silicone, and yttrium oxide. A thermal characteristic of the textile composition may, but need not, be altered relative to the same thermal characteristic of the textile composition in the absence of the thermal dopant, wherein the thermal characteristic is selected from the group consisting of thermal effusivity, thermal conductivity, heat capacity, and combinations thereof.

In another aspect of the present invention, an article of manufacture comprises a textile composition as described herein, wherein the article of manufacture is selected from the group consisting of an article of clothing, an accessory item, and a furniture item.

In another aspect of the present invention, a method for making a durable sheet material comprises (a) contacting an inactivated fungal biomass with an aqueous solution comprising calcium hydroxide to form a limed inactivated fungal biomass; (b) contacting the limed inactivated fungal biomass with an aqueous solution comprising ammonium sulfate to form a delimed inactivated fungal biomass; (c) contacting the delimed inactivated fungal biomass with an aqueous solution comprising a polymer to form a pickled inactivated fungal biomass; (d) contacting the pickled inactivated fungal biomass with an aqueous solution comprising a crosslinker to form a tanned inactivated fungal biomass; (e) contacting the tanned inactivated fungal biomass with an aqueous solution comprising a plasticizer to form a plasticized inactivated fungal biomass; (f) drying the plasticized inactivated fungal biomass to form a dried inactivated fungal biomass; and (g) heat-pressing the dried inactivated fungal biomass to form the durable sheet material.

In embodiments, the method may further comprise, between any pair of steps selected from the group consisting of steps (a) and (b), steps (b) and (c), steps (c) and (d), and steps (d) and (e), rinsing the inactivated fungal biomass with water to remove residual aqueous solution.

In embodiments, at least one of steps (a) through (e) may comprise agitating the inactivated fungal biomass with the aqueous solution.

In embodiments, the aqueous solution of at least one of steps (a) through (c) may further comprise a surfactant or solubilizer. The surfactant or solubilizer may, but need not, be selected from the group consisting of polysorbates, hydrochloric acid, acetic acid, formic acid, lactic acid, and combinations and mixtures thereof.

In embodiments, the polymer may be selected from the group consisting of polyvinyl alcohol, chitosan, polyethylene glycol, alginates, starches, polycaprolactones, polyacrylic acids, hyaluronic acid, and combinations and mixtures thereof.

In embodiments, the aqueous solution of step (c) may further comprise a plasticizer selected from the group consisting of glycerol and esters thereof, polyethylene glycol, citric acid, oleic acid, oleic acid polyols and esters thereof, epoxidized triglyceride vegetable oils, castor oil, pentaerythritol, fatty acid esters, carboxylic ester-based plasticizers, trimellitates, adipates, sebacates, maleates, biological plasticizers, and combinations and mixtures thereof.

In embodiments, the aqueous solution of step (c) may further comprise an alkali metal halide. The alkali metal halide may, but need not, be sodium chloride.

In embodiments, the crosslinker may be selected from the group consisting of citric acid, tannic acid, suberic acid, adipic acid, succinic acid, extracted vegetable tannins, glyoxal, and combinations and mixtures thereof.

In embodiments, the plasticizer may be selected from the group consisting of glycerol and esters thereof, polyethylene glycol, citric acid, oleic acid, oleic acid polyols and esters thereof, epoxidized triglyceride vegetable oils, castor oil, pentaerythritol, fatty acid esters, carboxylic ester-based plasticizers, trimellitates, adipates, sebacates, maleates, biological plasticizers, and combinations and mixtures thereof.

In another aspect of the present invention, a method for making a durable sheet material comprises (a) inactivating a fungal biomass by boiling the biomass in water; (b) contacting the inactivated fungal biomass with an aqueous solution comprising calcium hydroxide to form a limed inactivated fungal biomass; (c) contacting the limed inactivated fungal biomass with an aqueous solution comprising ammonium sulfate to form a delimed inactivated fungal biomass; (d) contacting the delimed inactivated fungal biomass with an aqueous solution comprising an alkali metal halide to form a pickled inactivated fungal biomass; (e) contacting the pickled inactivated fungal biomass with a first crosslinker to form a tanned inactivated fungal biomass; (f) contacting the tanned inactivated fungal biomass with an aqueous solution comprising at least one of a second crosslinker and a polymer to form a re-tanned inactivated fungal biomass; (g) contacting the re-tanned inactivated fungal biomass with a fatliquoring oil to form a fatliquored inactivated fungal biomass; (h) adhering a non-fungal textile backing to the inactivated fungal biomass to form a backed inactivated fungal biomass; (i) heat-pressing the backed inactivated fungal biomass to form a heat-pressed inactivated fungal biomass; (j) drying the heat-pressed inactivated fungal biomass to form a dried inactivated fungal biomass; and (k) applying at least one of a finishing wax, a finishing oil, and nitrocellulose to the dried inactivated fungal biomass to form the durable sheet material.

In embodiments, the method may further comprise, between any pair of steps selected from the group consisting of steps (b) and (c), steps (c) and (d), and steps (e) and (f), rinsing the inactivated fungal biomass with water to remove residual aqueous solution.

In embodiments, at least one of steps (a) through (g) may comprise agitating the inactivated fungal biomass with the aqueous solution.

In embodiments, the aqueous solution of at least one of steps (b) and (c) may further comprise a surfactant or solubilizer. The surfactant or solubilizer may, but need not, be selected from the group consisting of polysorbates, hydrochloric acid, acetic acid, formic acid, lactic acid, and combinations and mixtures thereof.

In embodiments, the polymer may, but need not, be selected from the group consisting of polyvinyl alcohol, chitosan, polyethylene glycol, alginates, starches, polycaprolactones, polyacrylic acids, hyaluronic acid, and combinations and mixtures thereof.

In embodiments, the alkali metal halide may be sodium chloride.

In embodiments, the aqueous solution of at least one of steps (d) through (f) may comprise a pH adjusting agent. The pH adjusting agent may, but need not, comprise hydrochloric acid, acetic acid, formic acid, lactic acid, or a combination or mixture thereof, or a metal hydroxide.

In embodiments, the first crosslinker may comprise an aluminum salt, a chromium salt, a titanium salt, an aldehyde, or a combination or mixture thereof. The first crosslinker may, but need not, be an aluminum silicate.

In embodiments, the second crosslinker may be selected from the group consisting of citric acid, tannic acid, suberic acid, adipic acid, succinic acid, extracted vegetable tannins, glyoxal, and combinations and mixtures thereof.

In embodiments, the polymer may be selected from the group consisting of polyvinyl alcohol, chitosan, polyethylene glycol, alginates, starches, polycaprolactones, polyacrylic acids, hyaluronic acid, and combinations and mixtures thereof.

In embodiments, the aqueous solution of step (f) may further comprise an anionic dye.

In embodiments, the fatliquoring oil may be selected from the group consisting of sulfated castor oil, beeswax, coconut oil, vegetable oil, olive oil, linseed oil, oleic acid, and combinations and mixtures thereof.

In embodiments, the fatliquoring oil may comprise an emulsion and the method may further comprise, between steps (g) and (h), contacting the fatliquoring oil with an acid to dissociate the emulsion.

In embodiments, the finishing wax may be selected from the group consisting of carnauba wax, candelilla wax, and combinations and mixtures thereof.

Embodiments of the present invention generally relate to production of durable sheet materials comprising fungal biomass. In certain embodiments, durable sheet materials may have controlled, engineered, and/or tuned thermal properties. By way of first non-limiting example, thermal properties of durable sheet materials of the present invention may be controlled, engineered, and/or tuned by controlling the size, number, and/or spatial distribution of air bubbles in the durable sheet material. By way of second non-limiting example, thermal properties of durable sheet materials of the present invention may be controlled, engineered, and/or tuned by adding a thermal dopant having a desired thermal property (e.g. heat capacity, thermal conductivity, thermal effusivity, and combinations thereof) and thus modifying the same thermal property of the durable sheet material as a whole. By way of third non-limiting example, thermal properties of durable sheet materials of the present invention may be controlled, engineered, and/or tuned by controlling the mass, volume, thickness, spatial distribution, etc. of thermal dopants included in the durable sheet material, thereby providing for an engineered or designed spatial pattern of heat exchange in and through the durable sheet material.

Embodiments of the present invention provide for the manufacture of fungal textile materials, and particularly fungal leather analogs, from intact cohesive fungal biomasses (e.g. fungal biomats produced by surface fermentation or any other suitable process), size-reduced or homogenized fungal biomasses, or any other physical form of fungal biomass, especially filamentous fungal biomass. The materials of the present invention generally include both an inactivated fungal biomass and a component selected from the group consisting of a polymer, a plasticizer, a crosslinker, and a dye, and the methods of the present invention allow for the introduction of such component(s) to the inactivated fungal biomass to produce materials having desired chemical, physical, and/or thermal properties. The materials of the present invention may generally be provided as durable sheet materials suitable for use in the same or similar applications as conventional textiles.

DETAILED DESCRIPTION OF THE INVENTION

Figure 1:
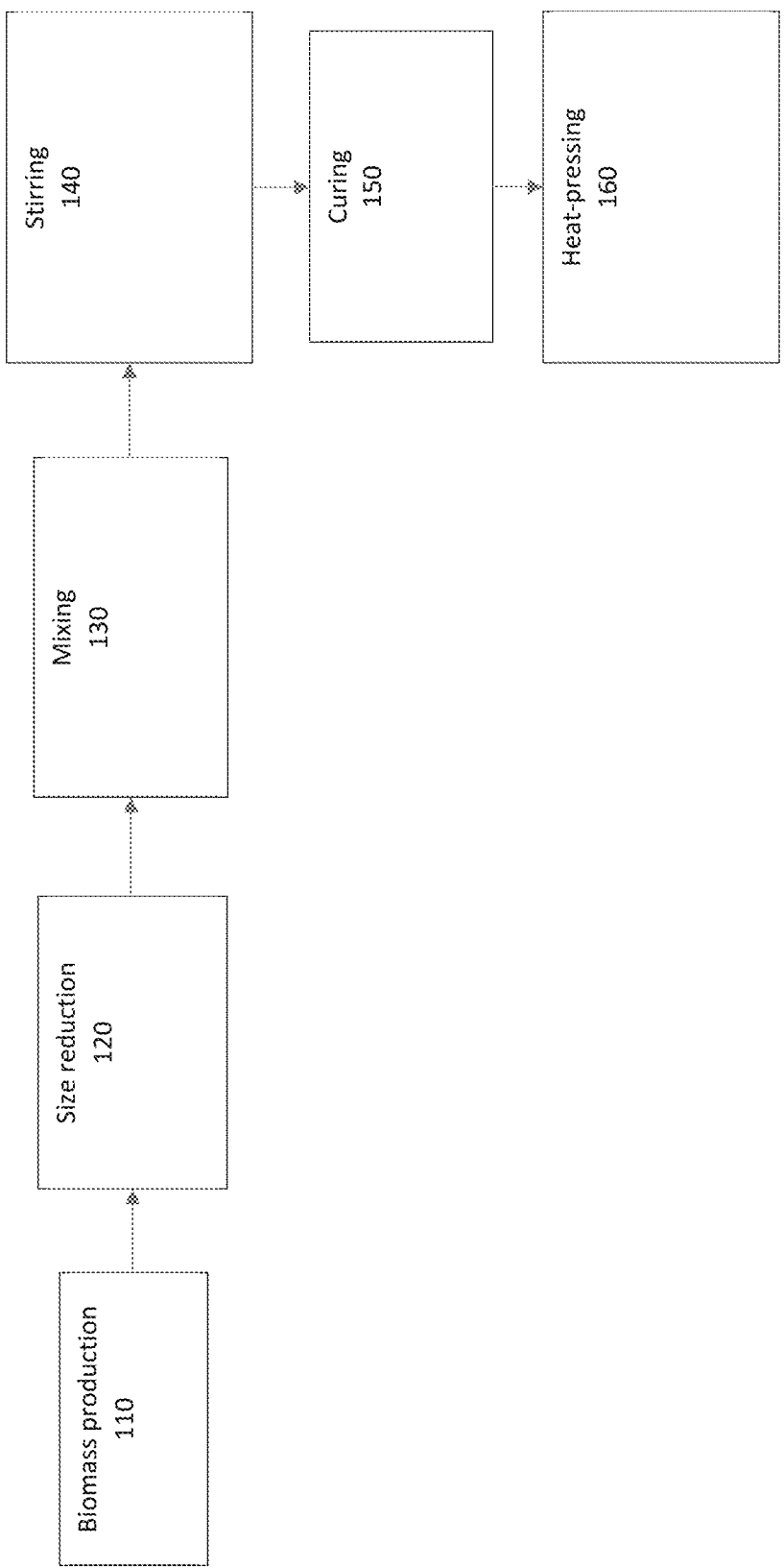
FIG. 1 is a generalized schematic of a method for making a fungal textile material, according to embodiments of the present invention.

As used herein, unless otherwise specified, the term "biodegradable" refers to a material that, under a given set of conditions (e.g. the conditions specified in ISO 20136: 2017, "Leather—determination of degradability by microorganisms"), biodegrades more quickly than "true" (i.e. animal) leather.

As used herein, unless otherwise specified, the term "degree of swelling" refers to the relative amount of change in the mass of a solid item when the solid is saturated with a liquid. By way of non-limiting example, a solid item that has a mass of 200 g when dry and a mass of 300 g when saturated with water has a degree of swelling in water of 50%, or 0.5. Where the term "degree of swelling" is used herein without explicitly identifying a liquid, the liquid may be assumed to be water.

As used herein, unless otherwise specified, the term "durable" refers to a material that has at least one of a tear strength of at least about 5 N/mm, a tear force of at least about 5 N, and a tensile strength of at least about 1.5 MPa.

As used herein, unless otherwise specified, the term "fungal biomass" refers to a mass of a fungus that has been cultured, fermented, or grown by any suitable process. It is to be expressly understood that fungal biomass may be produced by any of a number of methods known in the art and disclosed herein, including but not limited to surface fermentation methods, submerged fermentation methods, solid-substrate submerged fermentation (SSSF) methods, and methods as disclosed in PCT Application Publication WO2019/099474 ("the '474 publication"), the entirety of which is incorporated herein by reference.

As used herein, unless otherwise specified, the terms "hide leather" and "true leather" are interchangeable and each refer to a durable, flexible material created by tanning the hide or skin of an animal.

As used herein, unless otherwise specified, the term "inactivated" refers to fungal biomass that has been killed or otherwise prevented from actively growing by a suitable inactivation means, e.g. boiling, steaming, rinsing, irradiating, freezing, treating with an aqueous solution of at least 70% ethanol, treating with ethanol vapor, treating with bases or otherwise raising the pH (with or without heating), treating with acids or otherwise lowering the pH (with or without heating), or mechanically disrupting or destroying (such as by blending or otherwise size-reducing). It is to be expressly understood that a fungal biomass may be inactivated during, in combination with, and/or as a result of another process step, such as a size-reducing, liming, or deliming step.

As used herein, unless otherwise specified, the term "infiltration" refers to the permeation and/or saturation of a solution into a mass of solid material, such that the solution or a portion thereof is distributed in the mass of solid material, such as for example and without limitation, a polymer solution permeating the interstitial spaces in a fungal biomat comprised of mycelia. Without being bound by theory, the infiltration of a fungal mycelial biomass with a solution comprising components such as polymers and plasticizers, results in a textile material having such components distributed in the biomass after the solvent is removed by curing. Such a distribution can be substantially uniformly distributed or not uniformly distributed.

As used herein, unless otherwise specified, the term "loading ratio" refers to a weight ratio of fungal biomass to polymer in a fungal textile composition.

As used herein, unless otherwise specified, the term "mass loss upon soaking" refers to the relative amount of mass lost by a solid item after soaking in a liquid, disregarding the mass of liquid absorbed by the solid item. By way of non-limiting example, a solid item that has a mass of 100 grams when dry and a mass (disregarding the mass of absorbed liquid) of 95 grams after soaking in water has a mass loss upon soaking in water of 5%. Where the term "mass loss upon soaking" is used herein without explicitly identifying a liquid, the liquid may be assumed to be water.

As used herein, unless otherwise specified, the term "sheet" refers to a layer of solid material having a generally flat or planar shape and a high ratio of surface area to thickness.

As used herein, unless otherwise specified, the term "tannin" refers generally to any molecule that forms strong bonds with protein structures, and more particularly to a molecule that, when applied to hide leather, bonds strongly to protein moieties within the collagen structures of the skin to improve the strength and degradation resistance of the leather. The most commonly used types of tannins are vegetable tannins, i.e. tannins extracted from trees and plants, and chromium tannins such as chromium(III) sulfate. Other examples of tannins as that term is used herein include modified naturally derived polymers, biopolymers, and salts of metals other than chromium, e.g. aluminum silicate (sodium aluminum silicate, potassium aluminum silicate, etc.).

Referring now to FIG. 1, one embodiment of a method 100 for making a fungal textile material is illustrated. In a first step 110 of the method 100 illustrated in FIG. 1, a fungal biomass is produced by any of several suitable methods, including but not limited to methods described in PCT Application PCT/US2017/020050, filed 28 Feb. 2017 ("the '050 application"); PCT Application PCT/US2018/048626, filed 29 Aug. 2018 ("the '626 application"); U.S. Provisional Patent Application 62/811,421, filed 27 Feb. 2019 ("the '421 application"); and the '474 publication, the entireties of all of which are hereby incorporated by reference. As described in the '050 application, the '626 application, and the '421 application, the fungal biomass may be grown by surface fermentation in an artificial medium to form a cohesive structure of interwoven or interconnected mycelia called biomat. According to the methods described in the '050 application, the '626 application, and the '421 application, it may, in embodiments, be desirable to control an oil content and/or lipid content of the fungal biomass by providing a growth medium having a preselected ratio of carbon to nitrogen. Particularly, the production of certain lipids or oils, or amounts thereof, by the fungal biomass may result in fungal textile materials having certain desirable material characteristics, e.g. improved water resistance, decreased conditioning requirements, etc.; such characteristics may be amenable to control, engineering, or tuning by providing a preselected molar ratio of carbon to nitrogen in a fungal growth medium, which may in embodiments be between about 5 and about 20, or between about 7 and about 15. In some embodiments, the production of certain lipids or oils by the fungal biomass, e.g. oleic acid, linoleic acid, eicosenoic acid, palmitic acid, stearic acid, arachidic acid, behenic acid, etc. may allow for the use of certain polymers, solvents, etc. that may otherwise not be suitable in the practice of the invention and thereby provide properties of the fungal textile material that may otherwise be unattainable, or may provide additional or alternative synergistic effects of this kind.

In an optional second step 120 of the method 100 illustrated in FIG. 1, the fungal biomass may be size-reduced by any suitable method, which may, by way of non-limiting example, comprise being processed (e.g. in a blender, food processor, or similar size-reducing device), compressed (e.g. by moving jaws, rolls, gyratory cones, or similar compression device), impacted (e.g. by hammer, high-speed jet of material, rollers, or similar impact device), spray-dried, and the like. The size-reduction step may be carried out in any suitable device (e.g. a blender) for any suitable length of time (e.g. two minutes). During the size reduction step, at least a portion of a cohesive interconnected or interwoven mycelial network of the fungal biomass may be disrupted or destroyed.

In a third step 130 of the method 100 illustrated in FIG. 1, the fungal biomass is mixed with a solution of a synthetic polymer and/or a biopolymer. The synthetic polymer may be any synthetic polymer that is soluble in the solvent of choice, which may, but need not, be water; by way of non-limiting example, the synthetic polymer may be a polyvinyl alcohol, a polyethylene glycol, a polysiloxane, a polyphosphazene, a low- and/or high-density polyethylene, a polypropylene, a polyvinyl chloride, a polystyrene, a nylon, a polytetrafluoroethylene, a thermoplastic polyurethane, a polychlorotrifluoroethylene, a polycaprolactone, a polyacrylic acid, and/or any one or more synthetic polymers sold under various brand names (e.g. Bakelite, Kevlar, Mylar, Neoprene, Nomex, Orlon, Rilsan, Technora, Teflon, Twaron, Ultem, Vectran, Viton, Zylon, etc.). The biopolymer may be any polymeric molecule naturally produced by animals, plants, or fungi, including, by way of non-limiting example, cellulose, chitin, chitosan, collagen, fibroin, hyaluronic acid, keratin, alginates, starches, and combinations thereof. In embodiments, the solution (or another solution with which the biomat is combined in the same step or a preceding or following step) may also comprise additional components, such as, by way of non-limiting example, a plasticizer (e.g. glycerol and esters thereof, polyethylene glycol, citric acid, oleic acid, oleic acid polyols (e.g. mannitol, sorbitol) and esters thereof, epoxidized triglyceride vegetable oils (e.g. from soybean oil), castor oil, pentaerythritol, fatty acid esters, carboxylic ester-based plasticizers, trimellitates, adipates, sebacates, maleates, biological plasticizers, and combinations and mixtures thereof etc.) and/or a crosslinker (e.g. homobifunctional crosslinkers, heterobifunctional crosslinkers, photoreactive crosslinking agents, citric acid, tannic acid, suberic acid, adipic acid, succinic acid, extracted vegetable tannins, glyoxal, and combinations thereof). It is to be expressly understood that the size-reduction step (if any) and the mixing step can be carried out simultaneously or sequentially in any order.

In a fourth step 140 of the method 100 illustrated in FIG. 1, the biomass/solution mixture is stirred, typically at elevated temperature (by way of non-limiting example, about 90° C. to about 100° C.). After stirring, the biomass/solution mixture may optionally be further mixed with a dye to provide a desired color to the fungal textile material. In some embodiments, the dye may be added earlier in the process.

In a fifth step 150 of the method 100 illustrated in FIG. 1, the biomat/solution mixture is cured, optionally after being cast into a desired shape. The curing step may involve drying or the initiation of a chemical reaction and may drive off the solvent of the solution.

In a sixth step 160 of the method 100 illustrated in FIG. 1, the cured material is heat-pressed to form the desired fungal textile material. In embodiments, the fungal textile material may have at least one physical, mechanical, and/or aesthetic characteristic that mimics or closely resembles a physical, mechanical, and/or aesthetic characteristic of a conventional textile material such as leather.

Certain embodiments of the methods of the present invention may omit steps in which the fungal biomass is size-reduced (e.g. the second step 120 illustrated in FIG. 1). In some such embodiments, the biomass (e.g. a biomat produced according to the methods described in the '050 application, the '626 application, and/or the '421 application) may or may not have been previously size-reduced. In other embodiments, the biomass used may be a biomass that does not require size reduction, such as a fungal paste produced by submerged fermentation methods as known and described in the art.

Figure 2:
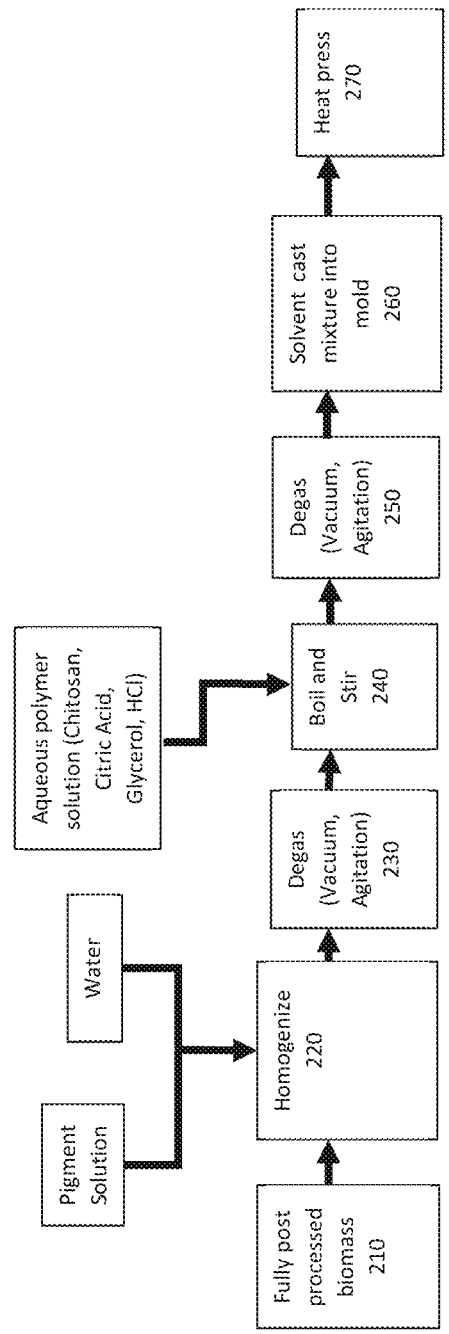
FIG. 2 is a generalized schematic of a method for making a fungal textile material, according to embodiments of the present invention.

Referring now to FIG. 2, another embodiment of a method 200 for making a fungal textile material is illustrated. In a first step 210 of the method 200 illustrated in FIG. 2, a fungal biomass is produced and processed by any of several suitable methods, including but not limited to methods described in the '050 application, the '626 application, the '421 application, and the '474 publication. The biomass may be boiled, rinsed, irradiated, and/or pressed to inactivate the organism and/or remove excess water and/or other liquid. The biomass may also be frozen, particularly where it is desirable or necessary to store the biomass for a period of time prior to performing the later steps and thus to extend the usable "shelf life" of the biomass.

In a second step 220 of the method 200 illustrated in FIG. 2, the fungal biomass is thawed (if previously frozen); size-reduced by any suitable method, which may, by way of non-limiting example, comprise being processed in a blender, food processor, mill, sonicator or similar size-reducing device; and blended or otherwise homogenized with water and, optionally, a pigment to provide a desired color to the fungal textile material. The size-reduction sub-step may be carried out in any suitable device (e.g. a blender) for any suitable length of time (e.g. two minutes). The blending/homogenizing sub-step produces a viscous, substantially homogeneous fungal paste. It is to be expressly understood that the size-reducing sub-step and the blending/homogenizing sub-step may be carried out simultaneously, sequentially in the same vessel, or sequentially in different vessels; by way of non-limiting example, water and optionally a pigment may be added to a blender together with the fungal biomass prior to the size-reduction sub-step, and these components may be blended simultaneously in the blender, thus carrying out the size-reduction sub-step and the blending/homogenizing sub-step simultaneously in the same vessel. In some embodiments, size-reducing the fungal biomass may also result in inactivation of the fungal biomass, e.g. by disrupting cellular structure of the fungus.

In an optional third step 230 of the method 200 illustrated in FIG. 2, the viscous, substantially homogeneous paste is degassed by any suitable method, which may, by way of non-limiting example, comprise one or more of agitation and vacuum treatment. Degassing the fungal material may provide improved qualities to the finished fungal textile product, including but not limited to a texture or "feel" that is more aesthetically pleasing to a user and/or more similar to a replicated material (e.g. true leather). In some embodiments, the degassing may be omitted; particularly, it may, in some embodiments, be desirable to allow at least some air bubbles or pockets to remain in the fungal paste, as this may impart certain desirable thermal or insulating properties to the finished fungal textile material.

In a fourth step 240 of the method 200 illustrated in FIG. 2, the fungal paste is mixed with a solution of a polymer in a solvent of choice. The solvent may, but need not, be water. The polymer may, but need not, be a biopolymer, i.e. any polymeric molecule naturally produced by animals, plants, or fungi, including, by way of non-limiting example, cellulose, chitin, chitosan, collagen, fibroin, hyaluronic acid, keratin, alginates, starches, and combinations thereof. In embodiments, the solution (or another solution with which the biomat is combined in the same step or a preceding or following step) may comprise, in addition to or as an alternative to a biopolymer, a synthetic polymer soluble in the solvent (e.g. a polyvinyl alcohol, a polyethylene glycol, a polysiloxane, a polyphosphazene, a low- and/or high-density polyethylene, a polypropylene, a polyvinyl chloride, a polystyrene, a nylon, a polytetrafluoroethylene, a thermoplastic polyurethane, a polychlorotrifluoroethylene, a polycaprolactone, a polyacrylic acid, and/or any one or more synthetic polymers sold under various brand names (e.g. Bakelite, Kevlar, Mylar, Neoprene, Nomex, Orlon, Rilsan, Technora, Teflon, Twaron, Ultem, Vectran, Viton, Zylon, etc.). In further embodiments, the solution may comprise one or more additional components, such as a plasticizer (e.g. glycerol and esters thereof, polyethylene glycol, citric acid, oleic acid, oleic acid polyols (e.g. mannitol, sorbitol) and esters thereof, epoxidized triglyceride vegetable oils (e.g. from soybean oil), castor oil, pentaerythritol, fatty acid esters, carboxylic ester-based plasticizers, trimellitates, adipates, sebacates, maleates, biological plasticizers, and combinations and mixtures thereof etc.), a crosslinker (e.g. homobifunctional crosslinkers, heterobifunctional crosslinkers, photoreactive crosslinking agents, citric acid, tannic acid, suberic acid, adipic acid, succinic acid, extracted vegetable tannins, glyoxal, and combinations thereof), a solubilizer (e.g. hydrochloric acid, acetic acid, formic acid, lactic acid, etc.), and/or a pH adjusting agent (e.g. hydrochloric acid, acetic acid, formic acid, lactic acid, etc.).

The solution may be made by combining the polymer and the solvent, and optionally one or more additional components, in a vessel and heating the combination while stirring. In embodiments in which the solution includes a solubilizer and/or a pH adjusting agent, either or both of these may be added to the solution after heating and stirring of the other components. Preferably, the polymer (biopolymer, synthetic polymer, or a combination thereof) is completely dissolved in the solvent before the solution is mixed with the optionally degassed fungal paste. The mixture may be heated (e.g. to about 90° C. and/or to boiling) and/or stirred for a time sufficient to ensure that the mixture is substantially homogeneous, e.g. between about 30 minutes and about 45 minutes.

In an optional fifth step 250 of the method 200 illustrated in FIG. 2, the mixture produced in the fourth step is degassed by any suitable method, which may, by way of non-limiting example, comprise one or more of agitation and vacuum treatment. Degassing the mixture may provide improved qualities to the finished fungal textile product, including but not limited to a texture or "feel" that is more aesthetically pleasing to a user and/or more similar to a replicated material (e.g. true leather). In some embodiments, the degassing may be omitted; particularly, it may, in some embodiments, be desirable to allow at least some air bubbles or pockets to remain in the mixture, as this may impart certain desirable thermal or insulating properties to the finished fungal textile material.

In a sixth step 260 of the method 200 illustrated in FIG. 2, the fungal mixture is cured, optionally after being cast into a desired shape (e.g. a flat or textured mold). The curing step may or may not involve curing or the initiation of a chemical reaction and may or may not drive off the solvent of the solution. The curing step may be carried out under ambient air at room temperature. The curing may be allowed to continue under conditions for a time sufficient to provide a desired mass (e.g. about 20% of the mass prior to drying/curing) and/or moisture content of the cured material.

In an optional seventh step 270 of the method 200 illustrated in FIG. 2, the cured material may be heat-pressed to form the desired fungal textile material. In embodiments, the fungal textile material may have at least one physical, mechanical, and/or aesthetic characteristic that mimics or closely resembles a physical, mechanical, and/or aesthetic characteristic of a conventional textile material such as leather. The temperature (e.g. about 100° C.) and/or time (e.g. between about 10 minutes and about 20 minutes) of the heat-pressing may be selected to provide the desired physical, mechanical, and/or aesthetic characteristic. The fungal textile material may, but need not, then be laminated to a textile backing; in these embodiments, a portion of the solution of the fourth step may, but need not, be utilized as an adhesive for adhering the fungal textile material to the textile backing.

Generally, the methods illustrated in FIGS. 1 and 2 cause a network of fungal filaments to be crosslinked together by a combination of a polymer (e.g. chitosan) and a crosslinker (e.g. citric acid). The polymer and crosslinker can form bonds via esterification reactions (between alcohol groups of the fungal filaments and/or the polymer, and carboxylic acid groups of the crosslinker and/or the fungal filaments) and/or amidation reactions (between amide groups of the fungal filaments and/or the polymer, and carboxylic acid groups of the crosslinker and/or the fungal filaments). These reactions may be catalyzed by, e.g. acidic conditions and/or heat (e.g. in a heat-pressing step). The use of a plasticizer such as glycerol can impart flexibility to the finished fungal textile material. The method of FIG. 1 can be used in conjunction with both intact and size-reduced fungal biomasses.

Figure 3:
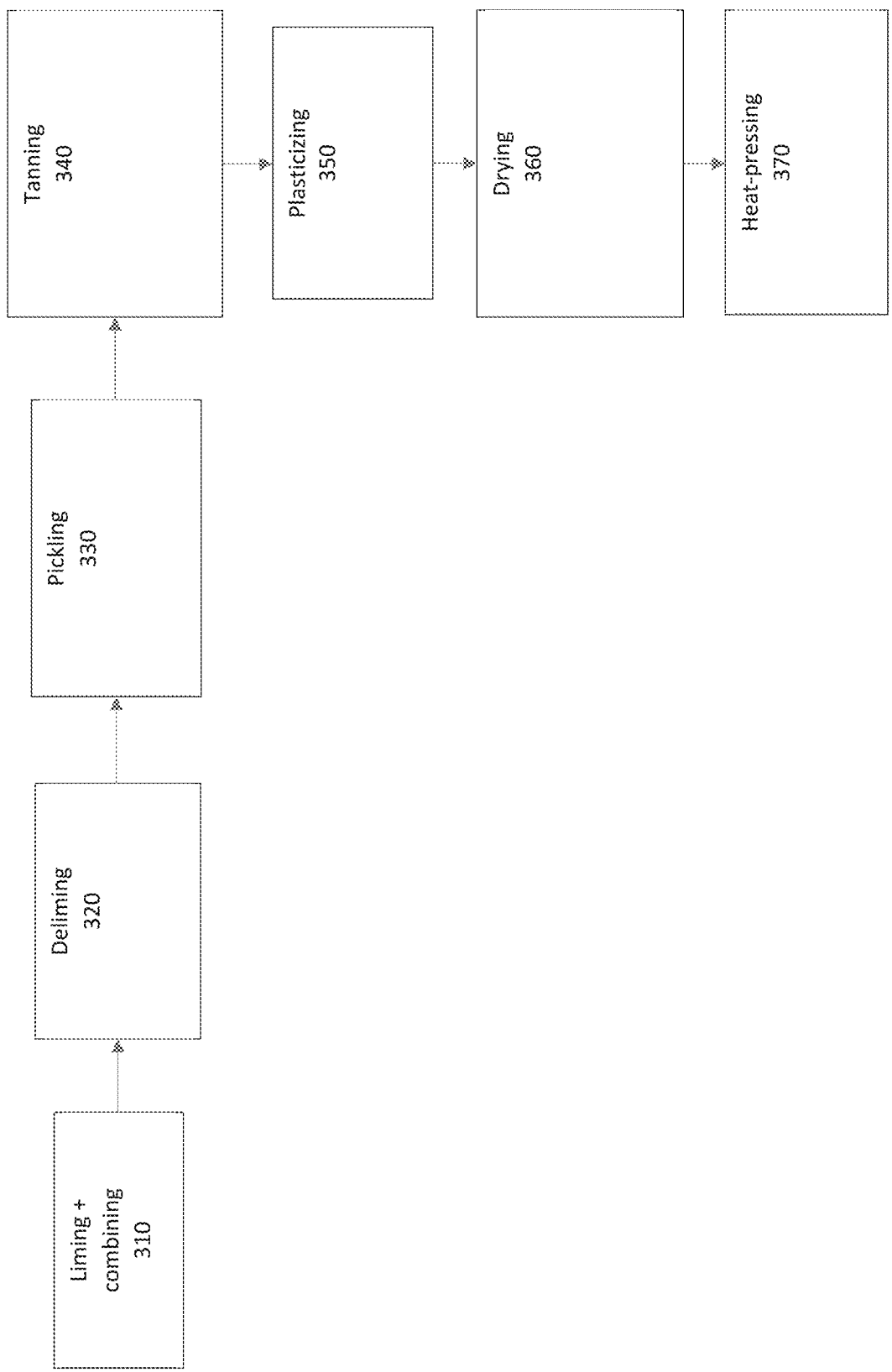
FIG. 3 is a generalized schematic of a method for making a fungal textile material, according to embodiments of the present invention.

Referring now to FIG. 3, another embodiment of a method 300 for making a fungal textile material is illustrated. In a liming step 310 of the method 300 illustrated in FIG. 3, an inactivated fungal biomass is added to an aqueous mixture or solution of components and agitated, e.g. on a shaker table. The aqueous mixture or solution comprises an aqueous solvent, a mass of which is typically about equal to that of the fungal biomass, and a liming substance, most commonly calcium hydroxide (i.e. slaked lime), in an amount of between about 0.01 wt % and about 6 wt % or any sub-range between those values, most commonly about 3 wt %, relative to the weight of the fungal biomass. The aqueous mixture or solution may optionally further include a solubilizer or surfactant, such as a polysorbate, in an amount of between about 0.01 wt % and about 1 wt % or any sub-range between those values, most commonly about 0.2 wt %, relative to the weight of the fungal biomass. The agitation may be carried out for any suitable time between about 1 minute and about 180 minutes or any sub-range between those values, most commonly about 90 minutes.

Prior to step 310, the fungal biomass may have been produced and processed by any of several suitable methods, including but not limited to methods described in the '050 application, the '626 application, the '421 application, and the '474 publication, and may be boiled, rinsed, irradiated, and/or pressed to inactivate the organism and/or remove excess water and/or other liquid. The biomass may also, prior to step 310, be frozen, particularly where it is desirable or necessary to store the biomass for a period of time prior to performing the later steps and thus to extend the usable "shelf life" of the biomass, and subsequently thawed.

Step 310 of the method 300 illustrated in FIG. 3 may be carried out on an intact fungal biomass, e.g. a cohesive fungal biomat produced by surface fermentation, or it may be carried out on a fungal biomass that has previously been size-reduced by any suitable method, which may, by way of non-limiting example, comprise being processed in a blender, food processor, mill, sonicator or similar size-reducing device. Any such size reduction may be carried out in any suitable device (e.g. a blender) for any suitable length of time (e.g. two minutes). In some embodiments, the fungal biomass may be active prior to size reduction and may be inactivated as a result of the size reduction, e.g. by disrupting cellular structure of the fungus. More generally, it is to be expressly understood that the fungal biomass may be inactivated during, in combination with, or as a result of any one or more other steps of the method 300, e.g. the liming step 310 (in which the pH of the fungal biomass is raised to at least about 7, or another pH sufficiently high to kill the fungus) or any of the other steps that follow (particularly if carried out at elevated temperature).

In a deliming step 320 of the method 300 illustrated in FIG. 3, the inactivated fungal biomass is added to an aqueous mixture or solution of components and agitated, e.g. on a shaker table. The aqueous mixture or solution comprises an aqueous solvent, a mass of which is typically about half that of the mass of the starting (i.e. prior to step 310) fungal biomass, and a deliming substance, most commonly ammonium sulfate, in an amount of between about 0.01 wt % and about 6 wt % or any sub-range between those values, most commonly about 3 wt %, relative to the weight of the starting (i.e. prior to step 310) fungal biomass. The aqueous mixture or solution may optionally further include a solubilizer or surfactant, such as a polysorbate, in an amount of between about 0.01 wt % and about 1 wt % or any sub-range between those values, most commonly about 0.2 wt %, relative to the weight of the starting (i.e. prior to step 310) fungal biomass. The agitation may be carried out for any suitable time between about 1 minute and about 180 minutes or any sub-range between those values, most commonly about 90 minutes.

In a pickling step 330 of the method 300 illustrated in FIG. 3, the inactivated fungal biomass is mixed with a solution of a polymer in an aqueous solvent. The polymer may, but need not, be a biopolymer, i.e. any polymeric molecule naturally produced by animals, plants, or fungi, including, by way of non-limiting example, cellulose, chitin, chitosan, collagen, fibroin, hyaluronic acid, keratin, alginates, starches, and combinations thereof. In embodiments, the solution (or another solution with which the inactivated fungal biomass is combined in the same step or a preceding or following step) may comprise, in addition to or as an alternative to a biopolymer, a synthetic polymer soluble in the solvent (e.g. a polyvinyl alcohol, a polyethylene glycol, a polysiloxane, a polyphosphazene, a low- and/or high-density polyethylene, a polypropylene, a polyvinyl chloride, a polystyrene, a nylon, a polytetrafluoroethylene, a thermoplastic polyurethane, a polychlorotrifluoroethylene, a polycaprolactone, a polyacrylic acid, and/or any one or more synthetic polymers sold under various brand names (e.g. Bakelite, Kevlar, Mylar, Neoprene, Nomex, Orlon, Rilsan, Technora, Teflon, Twaron, Ultem, Vectran, Viton, Zylon, etc.). In further embodiments, the solution may comprise one or more additional components, such as a plasticizer (e.g. glycerol and esters thereof, polyethylene glycol, citric acid, oleic acid, oleic acid polyols (e.g. mannitol, sorbitol) and esters thereof, epoxidized triglyceride vegetable oils (e.g. from soybean oil), castor oil, pentaerythritol, fatty acid esters, carboxylic ester-based plasticizers, trimellitates, adipates, sebacates, maleates, biological plasticizers, and combinations thereof), a crosslinker (e.g. homobifunctional crosslinkers, heterobifunctional crosslinkers, photoreactive crosslinking agents, citric acid, tannic acid, suberic acid, adipic acid, succinic acid, extracted vegetable tannins, glyoxal, and combinations thereof), a solubilizer (e.g. hydrochloric acid, acetic acid, formic acid, lactic acid, etc.), and/or a pH adjusting agent (e.g. hydrochloric acid, acetic acid, formic acid, lactic acid, etc.). An alkali metal halide (e.g. sodium chloride) may be provided to prevent swelling of the inactivated fungal biomass.

The solution may be made by combining the polymer and the solvent, and optionally one or more additional components, in a vessel and agitating or stirring the combination, optionally while heating the combination. In embodiments in which the solution includes a solubilizer and/or a pH adjusting agent, either or both of these may be added to the solution after heating and stirring of the other components. Preferably, the polymer (biopolymer, synthetic polymer, or a combination thereof) is completely dissolved in the solvent before the solution is mixed with the optionally degassed fungal paste. The mixture may be heated (e.g. to about 90° C. and/or to boiling) and/or stirred for a time sufficient to ensure that the mixture is substantially homogeneous, e.g. between about 1 minute and about 240 minutes or any sub-range between those values, and most typically between about 30 minutes and about 45 minutes or about 120 minutes.

The polymer solution to which the inactivated fungal biomass is added in step 330 of the method 300 generally includes a mass of aqueous solvent that is generally about equal to that of the starting (i.e. prior to step 310) fungal biomass; and the polymer in an amount of between about 0.01 wt % and about 10 wt % or any sub-range between those values, most commonly about 1 wt %, relative to the starting (i.e. prior to step 310) fungal biomass. Other components, if present during step 330, may be provided in any appropriate amount; by way of non-limiting example, a solubilizer or a pH adjusting agent may be provided in an amount of between about 0.01 wt % and about 10 wt % or any sub-range between those values, most commonly between about 0.5 wt % and about 2.5 wt %, relative to the starting (i.e. prior to step 310) fungal biomass, and the alkali metal halide may be provided in an amount of between about 0.01 wt % and about 14 wt % or any sub-range between those values, most commonly about 7 wt %, relative to the starting (i.e. prior to step 310) fungal biomass.

In a tanning step 340 of the method 300 illustrated in FIG. 3, the inactivated fungal biomass from the pickling step 330 is added to an aqueous solution comprising a crosslinking or tanning agent and agitated, e.g. on a shaker table. The aqueous solution comprises an aqueous solvent, a mass of which is typically about equal to that of the mass of the starting (i.e. prior to step 310) fungal biomass, and a crosslinking or tanning agent, e.g. citric acid and/or tannic acid, in an amount of between about 0.01 wt % and about 12 wt %, most commonly about 5 wt %, relative to the weight of the starting (i.e. prior to step 310) fungal biomass. The agitation may be carried out for any suitable time between about 1 minute and about 360 minutes or any sub-range between those values, most commonly about 180 minutes.

Although not illustrated in FIG. 3, the method 300 may optionally comprise one or more rinsing steps, in which the inactivated fungal biomass is rinsed with water to remove excess aqueous solution, after any one or more of liming step 310, deliming step 320, pickling step 330, and tanning step 340. A rinsing step may comprise draining the vessel containing the inactivated fungal biomass (e.g. a shaker flask) of excess aqueous solution, refilling the vessel with water, agitating the vessel, and draining the vessel of water.

In a plasticizing step 350 of the method 300 illustrated in FIG. 3, the inactivated fungal biomass is added to an aqueous solution comprising a plasticizer and agitated, e.g. on a shaker table. The aqueous solution comprises an aqueous solvent, a mass of which is typically about equal to that of the mass of the starting (i.e. prior to step 310) fungal biomass, and a plasticizer, e.g. glycerol, in an amount of between about 0.01 wt % and about 50 wt % or any sub-range between those values, most commonly about 25 wt %, relative to the weight of the starting (i.e. prior to step 310) fungal biomass. The agitation may be carried out for any suitable time between about 1 minute and about 180 minutes or any sub-range between those values, most commonly about 90 minutes. In some embodiments, the plasticizing step 350 may be a fatliquoring step, i.e. the plasticizer may be a fatliquoring oil such as sulfated castor oil, beeswax, coconut oil, vegetable oil, olive oil, linseed oil, oleic acid, sulfated fish oil, sulfated canola oil, soybean oil, palm oil, fatty acids, or a combination thereof.

In a drying step 360 of the method 300 illustrated in FIG. 3, the inactivated fungal biomass is dried, optionally after being cast into a desired shape (e.g. a flat or textured mold) if produced from a size-reduced fungal biomass. The drying step may or may not involve the initiation of a chemical reaction, but generally results in at least most of any residual water, solvents, and other liquids being driven from the inactivated fungal biomass. The drying may be passive (i.e. at room temperature without the use of a blower, fan, etc.) or active (i.e. under heating and/or using forced air, dry milling, etc.); when the drying is active, the temperature may be raised to a desired temperature above room temperature, most commonly about 80° F., and/or any suitable air forcing means (e.g. a blower, a fan, a forced-air dehydrator, etc.)

may be used. In some embodiments, at least a portion of the fungal material may be clamped or otherwise pressed to reduce shrinkage. The curing may be allowed to continue under conditions for a time sufficient to provide a desired mass (e.g. about 20% of the mass prior to drying/curing) and/or moisture content of the cured material, which may in embodiments be between about 1 minute and about 2 days or any sub-range between those values, most commonly about 1 day.

In a heat-pressing step 370 of the method 300 illustrated in FIG. 3, the inactivated fungal biomass is heat-pressed to form the desired fungal textile material. In embodiments, the fungal textile material may have at least one physical, mechanical, and/or aesthetic characteristic that mimics or closely resembles a physical, mechanical, and/or aesthetic characteristic of a conventional textile material such as leather; particularly, the heat-pressing step may be configured to impart a leather-like texture to the fungal textile material. The temperature (e.g. about 100° C.) and/or time (e.g. between about 1 minute and about 20 minutes, most commonly about 10 minutes) of the heat-pressing may be selected to provide the desired physical, mechanical, and/or aesthetic characteristic. The fungal textile material may, but need not, then be laminated to a non-fungal textile backing.

Figure 4:
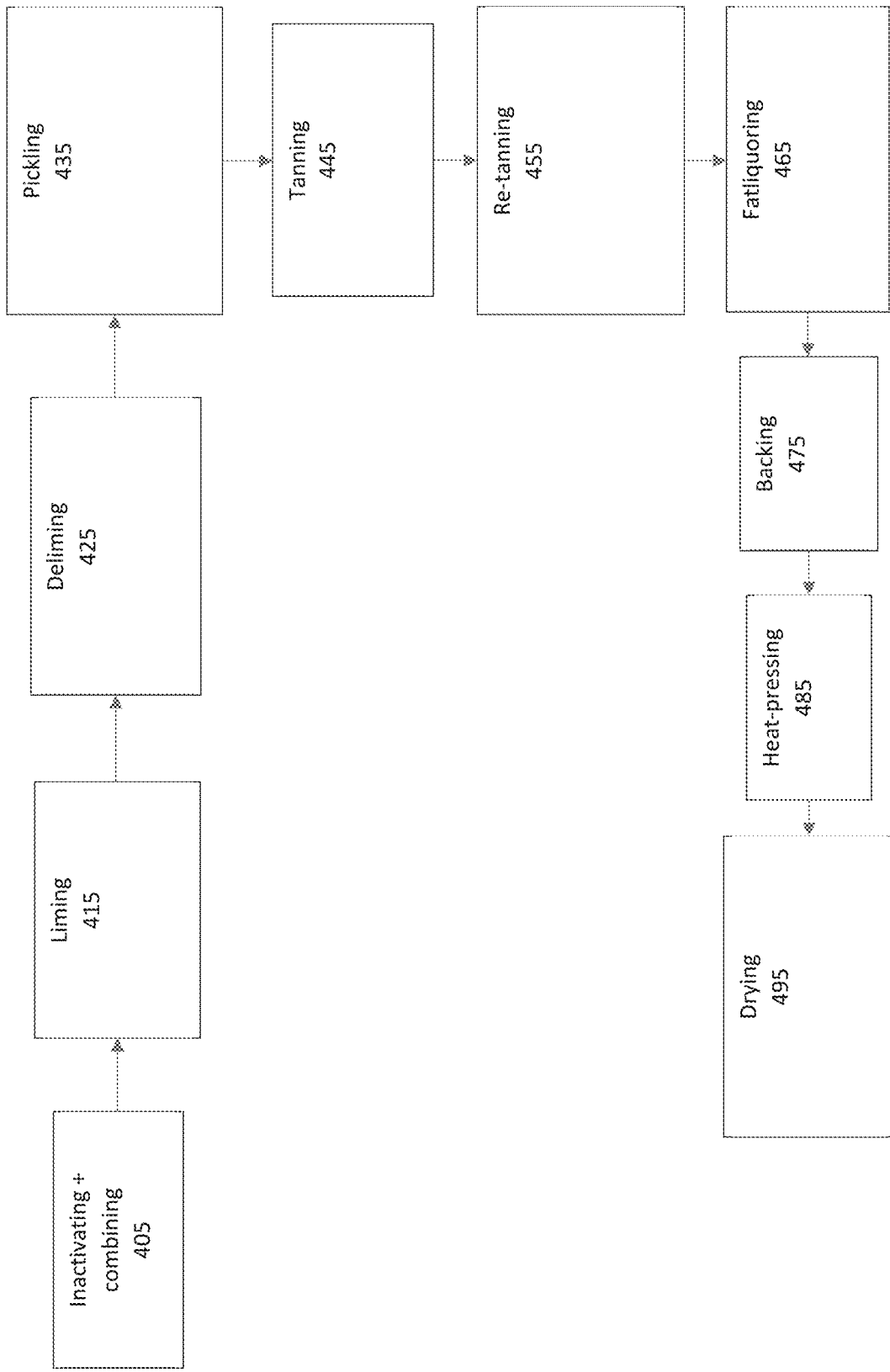
FIG. 4 is a generalized schematic of a method for making a fungal textile material, according to embodiments of the present invention.

Referring now to FIG. 4, another embodiment of a method 400 for making a fungal textile material is illustrated. In an inactivating step 405, the fungal biomass is inactivated to prevent active growth and metabolism of the fungus. This inactivation may commonly be effected by boiling the fungal biomass in a sufficient volume of water to completely submerge or surround the fungal biomass; this boiling is typically conducted for a period of between about 1 minute and about 60 minutes or any sub-range between those values, most commonly about 30 minutes. Of course, the inactivating step 405 may also be conducted by any other suitable means, such as by irradiating, freezing, size-reducing, or a combination of these with or without boiling.

Prior to step 405, the fungal biomass may have been produced and processed by any of several suitable methods, including but not limited to methods described in the '050 application, the '626 application, the '421 application, and the '474 publication. The biomass may also, prior to step 405, be frozen, particularly where it is desirable or necessary to store the biomass for a period of time prior to performing the later steps and thus to extend the usable "shelf life" of the biomass, and subsequently thawed.

Step 405 of the method 400 illustrated in FIG. 4 may be carried out on an intact fungal biomass, e.g. a cohesive fungal biomat produced by surface fermentation, or it may be carried out on a fungal biomass that has previously been size-reduced by any suitable method, which may, by way of non-limiting example, comprise being processed in a blender, food processor, mill, sonicator or similar size-reducing device. Any such size reduction may be carried out in any suitable device (e.g. a blender) for any suitable length of time (e.g. two minutes). In some embodiments, the fungal biomass may be active prior to size reduction and may be inactivated as a result of the size reduction, e.g. by disrupting cellular structure of the fungus.

Step 405 generally also includes dissolving, mixing, or suspending the inactivated fungal biomass in an aqueous solvent and may also include adding a solubilizer or surfactant, e.g. a polysorbate, to the inactivated fungal biomass and combining the solubilizer or surfactant with the inactivated fungal biomass, e.g. by agitation. A mass of the aqueous solvent may generally be between about half and about six times, most commonly about three times, that of the inactivated fungal biomass. The solubilizer or surfactant may be provided in an amount of between about 0.01 wt % and about 1 wt % or any sub-range between those values, most commonly about 0.2 wt %, relative to the weight of the fungal biomass. The agitation or other mechanical manipulation to combine the inactivated fungal biomass with the aqueous solvent, and optionally the solubilizer or surfactant, may be carried out for a period of between about 1 minute and about 60 minutes or any sub-range between those values, most commonly about 30 minutes.

In a liming step 415 of the method 400 illustrated in FIG. 4, the inactivated fungal biomass is added to an aqueous mixture or solution of components and agitated, e.g. on a shaker table. The aqueous mixture or solution comprises an aqueous solvent, a mass of which is typically about equal to that of the fungal biomass, and a liming substance, most commonly calcium hydroxide (i.e. slaked lime), in an amount of between about 0.01 wt % and about 10 wt % or any sub-range between those values, most commonly about 3 wt %, relative to the weight of the fungal biomass. The aqueous mixture or solution may optionally further include a solubilizer or surfactant, such as a polysorbate, in an amount of between about 0.01 wt % and about 1 wt % or any sub-range between those values, most commonly about 0.2 wt %, relative to the weight of the fungal biomass. The agitation may be carried out for any suitable time between about 1 minute and about 300 minutes or any sub-range between those values, most commonly about 150 minutes.

In a deliming step 425 of the method 400 illustrated in FIG. 4, the inactivated fungal biomass is added to an aqueous mixture or solution of components and agitated, e.g. on a shaker table. The aqueous mixture or solution comprises an aqueous solvent, a mass of which is typically about half that of the mass of the starting (i.e. prior to step 405) fungal biomass, and a deliming substance, most commonly ammonium sulfate or ammonium chloride, in an amount of between about 0.01 wt % and about 10 wt % or any sub-range between those values, most commonly about 3 wt %, relative to the weight of the starting (i.e. prior to step 405) fungal biomass. The aqueous mixture or solution may optionally further include a solubilizer or surfactant, such as a polysorbate, in an amount of between about 0.01 wt % and about 0.4 wt % or any sub-range between those values, most commonly about 0.2 wt %, relative to the weight of the starting (i.e. prior to step 405) fungal biomass. The agitation may be carried out for any suitable time between about 1 minute and about 150 minutes or any sub-range between those values, most commonly about 75 minutes.

In a pickling step 435 of the method 400 illustrated in FIG. 4, the inactivated fungal biomass is mixed with an acid, most commonly hydrochloric acid, or other pH adjusting agent. Sufficient pH adjusting agent is added to achieve a target pH of no more than about 4.0, typically between about 0.5 and about 3.5, more typically between about 1.0 and about 3.0, even more typically between about 1.5 and about 2.5, and most typically about 2.0. It is generally desirable to choose a molarity and/or molality of the acid, or a concentration of pH adjusting agent in an aqueous solvent, that allows this target pH to be achieved by adding a preselected mass or volume of acid or liquid solution. The acid or aqueous solution of pH adjusting agent may further comprise an alkali metal halide, e.g. sodium chloride, to prevent swelling of the fungal biomass; the alkali metal halide may be present in an amount of between about 0.01 wt % and about 14 wt % or any sub-range between those values, most commonly about 7 wt %, relative to the starting (i.e. prior to step 405) fungal biomass. The inactivated fungal biomass may be agitated together with the acid and/or pH adjusting agent, and optionally the alkali metal halide, for a period of between about 1 minute and about 180 minutes or any sub-range between those values, most commonly about 90 minutes.

In a tanning step 445 of the method 400 illustrated in FIG. 4, a first crosslinking or tanning agent is added to the inactivated fungal biomass and the combination is agitated, e.g. in a drum or on a shaker table. The crosslinking or tanning agent may in embodiments comprise an aldehyde, an aluminum salt, a chromium salt, or a titanium salt, and may commonly comprise an aluminum silicate. The crosslinking or tanning agent may generally be provided in an amount of between about 0.01 wt % and about 15 wt % or any sub-range between those values, most commonly between about 1.5 wt % and about 7.5 wt %, relative to the weight of the starting (i.e. prior to step 405) fungal biomass. The agitation may be carried out for any suitable time between about 1 minute and about 180 minutes or any sub-range between those values, most commonly between about 30 minutes and about 150 minutes. During the agitation, a base or other pH adjusting agent, e.g. sodium hydroxide, may commonly be added, either at one time or at multiple times, to achieve and/or maintain a target pH, which in embodiments is generally between about 2.0 and about 6.0, typically between about 2.5 and about 5.5, more typically between about 3.0 and about 5.0, even more typically between about 3.5 and about 4.5, and most typically about 4.0.

Although not illustrated in FIG. 4, the method 400 may optionally comprise one or more rinsing steps, in which the inactivated fungal biomass is rinsed with water to remove excess aqueous solution, after any one or more of liming step 415, deliming step 425, and tanning step 445. A rinsing step may comprise draining the vessel containing the inactivated fungal biomass (e.g. a shaker flask) of excess aqueous solution, refilling the vessel with water, agitating the vessel, and draining the vessel of water.

In a re-tanning step 455 of the method 400 illustrated in FIG. 4, a second crosslinking or tanning agent is added to the inactivated fungal biomass and the combination is agitated, e.g. in a drum or on a shaker table. The second crosslinking or tanning agent may in embodiments comprise, e.g., citric acid, and may be provided in an amount of between about 0.01 wt % and about 6 wt % or any sub-range between those values, most commonly about 3 wt %, relative to the weight of the starting (i.e. prior to step 410) fungal biomass. The agitation may be carried out for any suitable time between about 1 minute and about 480 minutes or any sub-range between those values, most commonly about 60 minutes.

The re-tanning step 455 may optionally comprise additional substeps to impart additional substances or characteristics to the inactivated fungal biomass and thus to the finished fungal textile material. By way of first non-limiting example, the inactivated fungal biomass may be mixed with an aqueous solution of any polymer as disclosed herein and agitated, e.g. in a drum or on a shaker table. The polymer may be provided in an amount of between about 0.01 wt % and about 30 wt % or any sub-range between those values, most commonly between about 0.5 wt % and about 5 wt %, relative to the weight of the starting (i.e. prior to step 410) fungal biomass. The agitation may be carried out for any suitable time between about 1 minute and about 480 minutes or any sub-range between those values, most commonly about 60 minutes. By way of second non-limiting example, a dye, such as an anionic dye, may be added to the inactivated fungal biomass and the combination may be agitated, e.g. in a drum or on a shaker table, for a time sufficient to impart a desired color to the inactivated fungal biomass (typically between about 1 minute and about 240 minutes or any sub-range between those values, and most typically about 120 minutes). The addition of the optional components (e.g. polymer, dye, etc.) may be carried out before, after, or simultaneously with addition of the second crosslinking or tanning agent.

Throughout the re-tanning step 455, acids, bases, and/or other pH adjusting agents may be added to maintain a target pH. By way of first non-limiting example, it may, in some embodiments, be desirable to begin the re-tanning step 455 at an initial pH of between about 2.0 and about 6.0 (more typically between about 2.5 and about 5.5, more typically between about 3.0 and about 5.0, more typically between about 3.5 and about 4.5, and most typically about 4.0) and gradually raise the pH to between about 3.5 and about 7.5 (more typically between about 4.0 and about 7.0, more typically between about 4.5 and about 6.5, more typically between about 5.0 and about 6.0, and most typically about 5.5) by adding a base or other pH increasing agent in one or more aliquots during agitation. By way of second non-limiting example, where the re-tanning step 455 includes the addition of a polymer, it may, in some embodiments, be desirable to maintain a pH of between about 3.5 and about 7.5 (more typically between about 4.0 and about 7.0, more typically between about 4.5 and about 6.5, more typically between about 5.0 and about 6.0, and most typically about 5.5) during agitation of the inactivated fungal biomass together with the polymer.

The polymer may, but need not, be a biopolymer, i.e. any polymeric molecule naturally produced by animals, plants, or fungi, including, by way of non-limiting example, cellulose, chitin, chitosan, collagen, fibroin, hyaluronic acid, keratin, alginates, starches, and combinations thereof. In embodiments, the solution (or another solution with which the inactivated fungal biomass is combined in the same step or a preceding or following step) may comprise, in addition to or as an alternative to a biopolymer, a synthetic polymer soluble in the solvent (e.g. a polyvinyl alcohol, a polyethylene glycol, a polysiloxane, a polyphosphazene, a low- and/or high-density polyethylene, a polypropylene, a polyvinyl chloride, a polystyrene, a nylon, a polytetrafluoroethylene, a thermoplastic polyurethane, a polychlorotrifluoroethylene, a polycaprolactone, a polyacrylic acid, and/or any one or more synthetic polymers sold under various brand names (e.g. Bakelite, Kevlar, Mylar, Neoprene, Nomex, Orlon, Rilsan, Technora, Teflon, Twaron, Ultem, Vectran, Viton, Zylon, etc.). In further embodiments, the solution may comprise one or more additional components, such as a plasticizer (e.g. glycerol and esters thereof, polyethylene glycol, citric acid, oleic acid, oleic acid polyols (e.g. mannitol, sorbitol) and esters thereof, epoxidized triglyceride vegetable oils (e.g. from soybean oil), castor oil, pentaerythritol, fatty acid esters, carboxylic ester-based plasticizers, trimellitates, adipates, sebacates, maleates, biological plasticizers, and combinations and mixtures thereof etc.), a crosslinker (e.g. homobifunctional crosslinkers, heterobifunctional crosslinkers, photoreactive crosslinking agents, citric acid, tannic acid, suberic acid, adipic acid, succinic acid, extracted vegetable tannins, glyoxal, and combinations thereof), a solubilizer (e.g. hydrochloric acid, acetic acid, formic acid, lactic acid, etc.), and/or a pH adjusting agent (e.g. hydrochloric acid, acetic acid, formic acid, lactic acid, etc.). An alkali metal halide (e.g. sodium chloride) may be provided to prevent swelling of the inactivated fungal biomass.

The solution may be made by combining the polymer and the solvent, and optionally one or more additional components, in a vessel and agitating or stirring the combination, optionally while heating the combination. In embodiments in which the solution includes a solubilizer and/or a pH adjusting agent, either or both of these may be added to the solution after heating and stirring of the other components. Preferably, the polymer (biopolymer, synthetic polymer, or a combination thereof) is completely dissolved in the solvent before the solution is mixed with the inactivated fungal biomass. The mixture may be heated (e.g. to about 90° C. and/or to boiling) and/or stirred for a time sufficient to ensure that the mixture is substantially homogeneous, e.g. between about 1 minute and about 240 minutes, and most typically between about 30 minutes and about 45 minutes or about 120 minutes.

In a plasticizing step 465 of the method 400 illustrated in FIG. 4, a plasticizer is added to the inactivated fungal biomass and the combination is agitated, e.g. in a drum or on a shaker table. In embodiments, the plasticizing step may be a fatliquoring step, i.e. the plasticizer may comprise a fatliquoring oil such as sulfated castor oil, beeswax, coconut oil, vegetable oil, olive oil, linseed oil, oleic acid, sulfated fish oil, sulfated canola oil, soybean oil, palm oil, fatty acids, or a combination thereof, and may be provided in any suitable amount. The agitation may be carried out for any suitable time between about 1 minute and about 120 minutes or any sub-range between those values, most commonly about 60 minutes. The plasticizer may be provided as an emulsion, especially when the plasticizer is a traditional leather fatliquoring oil, and in some such embodiments the plasticizing step 465 may be concluded by adding an acid, e.g. hydrochloric acid, to the emulsion to split the emulsion and allow for easier draining and removal of the plasticizer.

In a backing step 475 of the method 400 illustrated in FIG. 4, at least one backing layer of a non-fungal textile material is applied to the inactivated fungal biomass and adhered to the inactivated fungal biomass. The non-fungal textile material may, in embodiments, include any one or more of an acrylic textile, an alpaca textile, an angora textile, a cashmere textile, a coir textile, a cotton textile, an eisengarn textile, a hemp textile, a jute textile, a Kevlar textile, a linen textile, a microfiber textile, a mohair textile, a nylon textile, an olefin textile, a pashmina textile, a polyester textile, a piña textile, a ramie textile, a rayon textile, a sea silk textile, a silk textile, a sisal textile, a spandex textile, a spider silk textile, and a wool textile. The adhesive may be any suitable laminating adhesive used in textiles, e.g. polyvinyl acetate, and may in some embodiments include any suitable amount of a crosslinker or plasticizer, e.g. citric acid.

In a heat-pressing step 485 of the method 400 illustrated in FIG. 4, the inactivated fungal biomass, together with the non-fungal textile backing, is heat-pressed. In embodiments, the fungal textile material may have at least one physical, mechanical, and/or aesthetic characteristic that mimics or closely resembles a physical, mechanical, and/or aesthetic characteristic of a conventional textile material such as leather; particularly, the heat-pressing step may be configured to impart a leather-like texture to the fungal textile material. The temperature (e.g. about 100° C.) and/or time (e.g. between about 1 minute and about 20 minutes, most commonly about 10 minutes) of the heat-pressing may be selected to provide the desired physical, mechanical, and/or aesthetic characteristic.

In a drying step 495 of the method 400 illustrated in FIG. 4, the inactivated fungal biomass is dried, optionally after being cast into a desired shape (e.g. a flat or textured mold), to form the fungal textile material. The drying step may or may not involve the initiation of a chemical reaction, but generally results in at least most of any residual water, solvents, and other liquids being driven from the inactivated fungal biomass. The drying may be passive (i.e. at room temperature without the use of a blower, fan, etc.) or active (i.e. under heating and/or using forced air); when the drying is active, the temperature may be raised to a desired temperature above room temperature, most commonly about 80° F., and/or any suitable air forcing means (e.g. a blower, a fan, a forced-air dehydrator, etc.) may be used. In some embodiments, at least a portion of the fungal material may be clamped or otherwise pressed to reduce shrinkage. The curing may be allowed to continue under conditions for a time sufficient to provide a desired mass (e.g. about 18% of the mass prior to drying/curing) and/or moisture content of the cured material, which may in embodiments be between about 1 minute and about 2 days, most commonly about 1 day.

Although not illustrated in FIG. 4, the method 400 may include at least one additional post-processing or final handling step. Particularly, one or more traditional leather finishing waxes or oils (e.g. carnauba wax, candelilla wax) or nitrocellulose may be added to the fungal textile material, in any suitable amount and for any suitable time.

Figure 5:
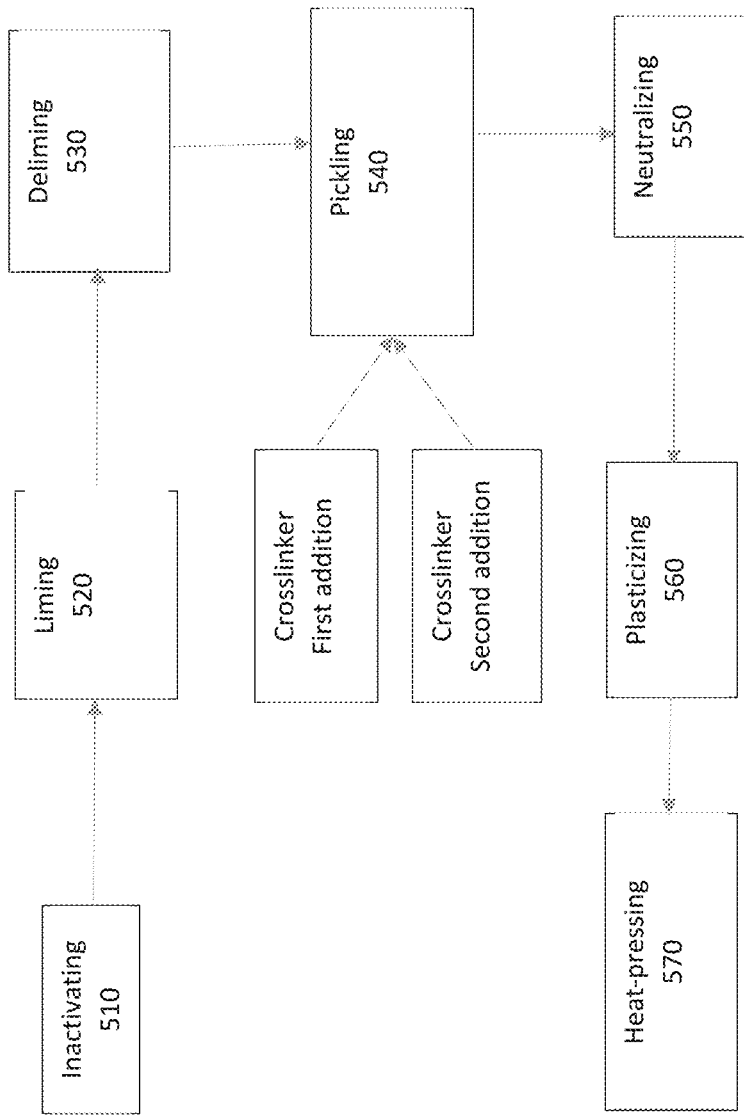
FIG. 5 is a generalized schematic of a method for making a fungal textile material, according to embodiments of the present invention.

Referring now to FIG. 5, another embodiment of a method 500 for making a fungal textile material is illustrated. In an inactivating step 510 of the method 500 illustrated in FIG. 5, a fungal biomass is inactivated as described herein, e.g. with respect to inactivating step 405 of the method 400 illustrated in FIG. 4. In a liming step 520 of the method 500 illustrated in FIG. 5, the inactivated fungal biomass is limed as described herein, e.g. with respect to liming step 310 of the method 300 illustrated in FIG. 3 and/or liming step 415 of the method 400 illustrated in FIG. 4. In a deliming step 530 of the method 500 illustrated in FIG. 5, the inactivated fungal biomass is delimed as described herein, e.g. with respect to deliming step 320 of the method 300 illustrated in FIG. 3 and/or deliming step 425 of the method 400 illustrated in FIG. 4.

In a pickling step 540 of the method 500 illustrated in FIG. 5, the inactivated fungal biomass is pickled as described herein, e.g. with respect to pickling step 330 of the method 300 illustrated in FIG. 3 and/or pickling step 435 of the method 400 illustrated in FIG. 4. However, one difference in the pickling step 540 of the method 500 illustrated in FIG. 5 relative to the pickling steps of other embodiments lies in the addition of at least two aliquots of crosslinker, e.g. tannic acid, to the combination of inactivated fungal biomass and polymer solution, or vice versa, such that the inactivated fungal biomass may be contacted with the polymer solution before being contacted with the first aliquot of crosslinker, or simultaneously with being contacted with the first aliquot of crosslinker, or after being contacted with the first aliquot of crosslinker but before being contacted with the second aliquot of crosslinker, or simultaneously with being contacted with the second aliquot of crosslinker, or after being contacted with the second aliquot of crosslinker. In this way, the method 500 of FIG. 5 may, in a sense, combine pickling, tanning, and re-tanning steps, e.g. steps 330 and 340 of method 300 and/or steps 435, 445, and 455 of method 400, into a single step comprising pickling, tanning, and re-tanning substeps.

In a neutralizing step 550 of the method 500 illustrated in FIG. 5, the pH of the inactivated fungal biomass is neutralized by contacting the inactivated fungal biomass with a pH neutralizing agent, which in most embodiments is a basic pH neutralizing agent, e.g. sodium bicarbonate, but may in some embodiments be an acidic pH neutralizing agent. The pH neutralizing agent may be provided as part of an aqueous solution, and may (but need not) be provided in a suitable amount to provide a pH of about 7. As with other steps, the neutralizing step 550 may be carried out with agitation, e.g. in a shaker flask.

In a plasticizing step 560 of the method 500 illustrated in FIG. 5, the inactivated fungal biomass is plasticized as described herein, e.g. with respect to plasticizing step 350 of the method 300 illustrated in FIG. 3 and/or plasticizing step 465 of the method 400 illustrated in FIG. 4. In a heat-pressing step 570 of the method 500 illustrated in FIG. 5, the inactivated fungal biomass is heat-pressed as described herein, e.g. with respect to heat-pressing step 370 of the method 300 illustrated in FIG. 3 and/or heat-pressing step 485 of the method 400 illustrated in FIG. 4.

Figure 6:
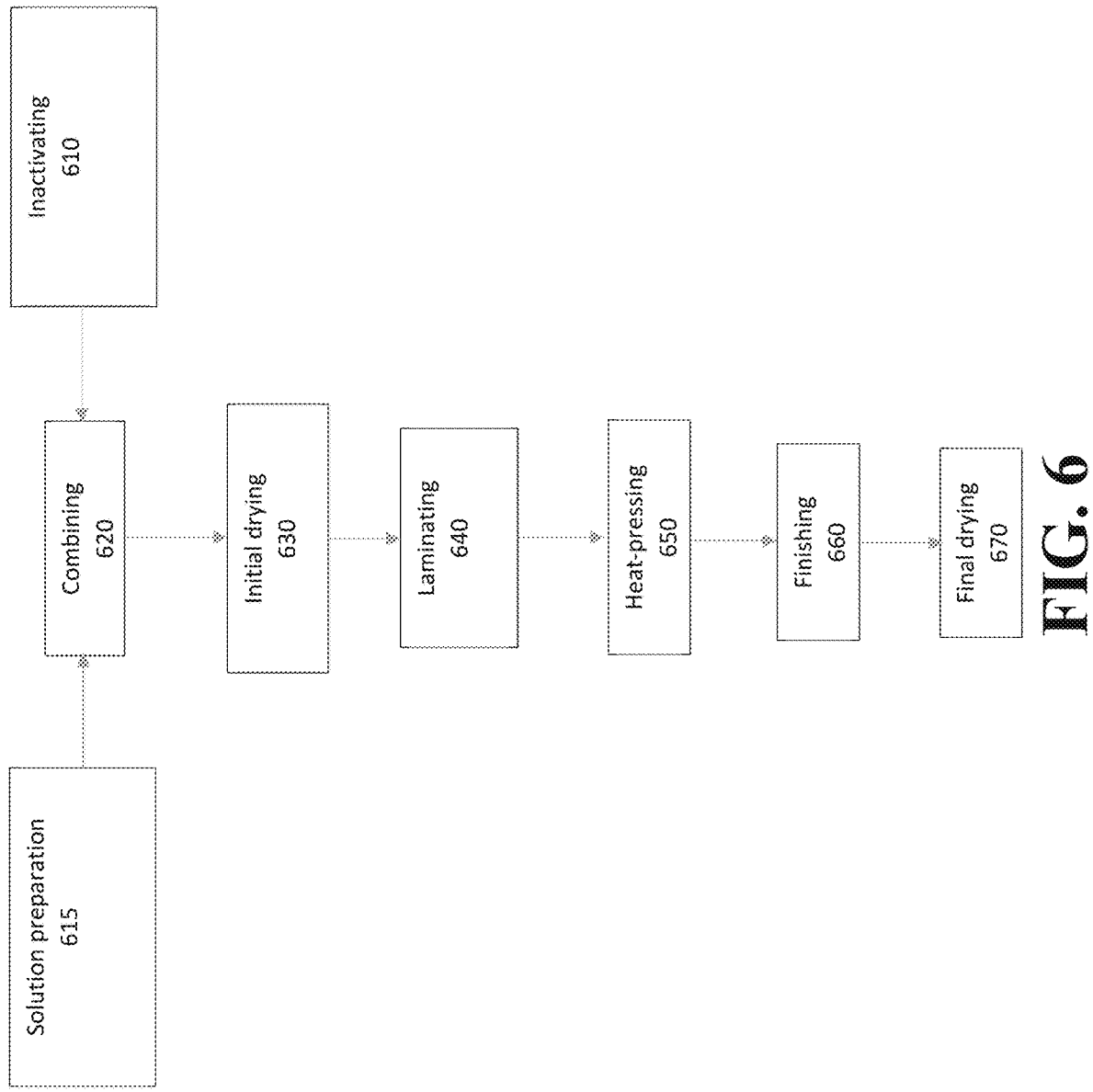
FIG. 6 is a generalized schematic of a method for making a fungal textile material, according to embodiments of the present invention.

Referring now to FIG. 6, another embodiment of a method 600 for making a fungal textile material is illustrated. In an inactivating step 610 of the method 600 illustrated in FIG. 6, a fungal biomass is inactivated as described herein, e.g. with respect to inactivating step 405 of the method 400 illustrated in FIG. 4. Separately, in a polymer solution preparation step 615 of the method 600 illustrated in FIG. 6, a polymer solution is prepared as described herein, e.g. with respect to pickling step 330 of the method 300 illustrated in FIG. 3. In a combining step 620 of the method 600 illustrated in FIG. 6, the inactivated fungal biomass is combined with the polymer solution as described herein, e.g. with respect to pickling step 330 of the method 300 illustrated in FIG. 3 and/or pickling step 435 of the method 400 illustrated in FIG. 4. In an initial drying step 630 of the method 600 illustrated in FIG. 6, the inactivated fungal biomass is dried as described herein, e.g. with respect to drying step 360 of the method 300 illustrated in FIG. 3 and/or drying step 495 of the method 400 illustrated in FIG. 4. In a laminating step 640 of the method 600 illustrated in FIG. 6, the inactivated fungal biomass is laminated together with one or more other inactivated fungal biomasses and/or layers of non-fungal textile materials, by any suitable method, to form a composite fungal sheet. In a heat-pressing step 650 of the method 600 illustrated in FIG. 6, the composite fungal sheet is heat-pressed as described herein, e.g. with respect to heat-pressing step 370 of the method 300 illustrated in FIG. 3 and/or heat-pressing step 485 of the method 400 illustrated in FIG. 4. In a finishing step 660 of the method 600 illustrated in FIG. 6, one or more traditional leather finishing waxes or oils (e.g. carnauba wax, candelilla wax) or nitrocellulose may be added to the composite fungal sheet, in any suitable amount and for any suitable time. In a final drying step 670 of the method 600 illustrated in FIG. 6, the composite fungal sheet is dried as described herein, e.g. with respect to drying step 360 of the method 300 illustrated in FIG. 3 and/or drying step 495 of the method 400 illustrated in FIG. 4, to form the fungal textile material.

Generally, the methods illustrated in FIGS. 3-5 utilize a series of chemical washes, which are conducted with agitation to increase diffusion of chemical species into the fungal structure and soften the feel of the finished fungal textile material. The liming steps of these methods swell the matrix of the fungal structure and cleave certain fungal proteins, allowing for better diffusion of chemical species into the fungus and exposing chemically active sites for reaction in later process steps. Vegetable tannins can then be effective to form large hydrogen bond networks and thus crosslink the fungal structure, providing a strength, color, smell, and/or chemical stability characteristic of true leather. As in the methods illustrated in FIGS. 1 and 2, a strengthening polymer (e.g. chitosan) and another non-tannin crosslinker (e.g. citric acid) can be employed; in addition to having the effects described above with respect to FIGS. 1 and 2, the strengthening polymer and non-tannin crosslinker can form complexes with the tannin crosslinker. Likewise, a plasticizer (e.g. glycerol) can also be incorporated into the methods.

It is to be expressly understood that any one or more filamentous fungi may suitably be used to form fungal textile materials of the present invention, including but not limited to one or more filamentous fungi belonging to a phylum selected from the group consisting of Ascomycota and Basidiomycota; one or more filamentous fungi belonging to an order selected from the group consisting of Ustilaginales, Russulales, Agaricales, Pezizales, and Hypocreales; one or more filamentous fungi belonging to a family selected from the group consisting of Ustilaginaceae, Hericiaceae, Polyporaceae, Grifolaceae, Lyophyllaceae, Strophariaceae, Lycoperdaceae, Agaricaceae, Pleurotaceae, Physalacriaceae, Omphalotaceae, Tuberaceae, Morchellaceae, Sparassidaceae, Nectriaceae, and Cordycipitaceae; one or more filamentous fungi belonging to a genus selected from the group consisting of *Agaricus, Calocybe, Calvatia, Cordyceps, Disciotis, Fomes, Fusarium, Ganoderma, Grifola, Hericulum, Hypholoma, Hypsizygus, Morchella, Pholiota, Pleurotus, Polyporous, Sparassis, Stropharia, Tuber, Ustilago*; and/or one or more filamentous fungi belonging to a species selected from the group consisting of *Ustilago esculenta, Hericulum erinaceus, Polyporous squamosus, Grifola fondosa, Hypsizygus marmoreus, Hypsizygus ulmarius, Calocybe gambosa, Pholiota nameko, Calvatia gigantea, Agaricus bisporus, Stropharia rugosoannulata, Hypholoma lateritium, Pleurotus eryngii, Pleurotus ostreatus, Pleurotus ostreatus* var. *columbinus, Tuber borchii, Morchella esculenta, Morchella conica, Morchella importuna, Sparassis crispa, Fusarium venenatum*, MK7 ATCC Accession Deposit No. PTA-10698, *Disciotis venosa*, and *Cordyceps militaris*.

In the practice of the present invention, inactivated fungal biomass is allowed to soak in and/or is agitated with the polymer, plasticizer, and/or crosslinker solution for a time sufficient to allow the mat to be penetrated by and/or saturated with the polymer, plasticizer, and/or crosslinker, generally at least about one hour. After soaking in and/or being agitated with the solution, the wet mat is removed from the solution (whereupon excess solution may be removed from one or more surfaces of the mat).

Plasticizers suitable for use in the fungal textile materials of the present invention include but are not limited to glycerol and esters thereof, polyethylene glycol, citric acid, oleic acid, oleic acid polyols (e.g. mannitol, sorbitol) and esters thereof, epoxidized triglyceride vegetable oils (e.g. from soybean oil), castor oil, pentaerythritol, fatty acid esters, carboxylic ester-based plasticizers, trimellitates, adipates, sebacates, maleates, biological plasticizers, and combinations and mixtures thereof. In the practice of the present invention, the plasticizer is typically present in the fungal textile material in an amount of between about 0.5 wt % and about 50 wt % or any sub-range between those values, including, by way of non-limiting example, about 50 wt %, about 37.5 wt %, about 25 wt %, or about 12.5 wt %.

Polymers suitable for use in the fungal textile materials of the present invention include but are not limited to polyvinyl alcohol, chitosan, polyethylene glycol, polycaprolactones, polyacrylic acids, hyaluronic acid, alginates, and combinations and mixtures thereof. In embodiments, two or more polymers may be included in any weight ratio between about 99:1 and about 1:99; typically about 99:1, about 90:10, about 80:20, about 70:30, about 60:40, about 50:50, about 40:60, about 30:70, about 20:80, about 10:90, or about 1:99; and more typically about 50:50. A loading ratio of the textile composition may take any value between about 99:1 and about 1:99; typically about 99:1, about 95:5, about 90:10, about 85:15, about 80:20, about 75:25, about 70:30, about 65:35, about 60:40, about 55:45, about 50:50, about 45:55, about 40:60, about 35:65, about 30:70, about 25:75, about 20:80, about 15:85, about 10:90, about 5:95, and about 1:99; and more typically about 70:30.

Crosslinkers suitable for use in the fungal textile materials of the present invention include but are not limited to citric acid, tannic acid, suberic acid, adipic acid, succinic acid, extracted vegetable tannins, glyoxal, and combinations and mixtures thereof. In embodiments, the fungal textile material may comprise proteins crosslinked with isopeptide bonds, the formation of which may in some embodiments be catalyzed by transglutaminase.

Relative amounts of filamentous fungus, plasticizer, polymer, crosslinker, additional components, etc. in the fungal textile materials of the present invention may be selected to provide a fungal textile material having one or more desired physical, mechanical, sensory (e.g. olfactory, tactile, etc.) and/or aesthetic characteristics. In embodiments, a scented additive, e.g. a leather fragrance oil, may be added to the fungal textile material to provide a desired olfactory characteristic, e.g. a leather-like aroma, to the fungal textile material.

The filamentous fungus may make up about 20%-90%, or any sub-range between those values, of the fungal textile material. In some embodiments, the filamentous fungus may make up between about 25-85%, about 30-80%, about 35-75% of the fungal textile material. For instance, in a non-limiting example, in some embodiments, it may make up between about 40 wt % and about 60 wt % of the fungal textile material.

By way of further non-limiting examples, one or more polymers (e.g. chitosan) may make up between about 1 wt % and about 40 wt %, or any sub-range between those values, or between about 5 wt % and about 20 wt %, of the fungal textile material. By way of third non-limiting example, one or more crosslinkers (e.g. citric acid) may make up between about 0.01 wt % and about 8 wt %, or any sub-range between those values, or between about 0.05 wt % and about 6 wt %, or between about 0.1 wt % and about 4 wt % of the fungal textile material. By way of fourth non-limiting example, one or more plasticizers (e.g. glycerol) may make up between about 0.5 wt % and about 80 wt %, or any sub-range between those values, or between about 9 wt % and about 60 wt %, or between about 17.5 wt % and about 40 wt % of the fungal textile material.

Embodiments of the present invention include fungal textile materials, and particularly fungal leather analog materials, having engineered and/or tuned thermal properties. By way of first non-limiting example, the thermal effusivity of the fungal textile material, i.e. the rate at which the fungal textile material exchanges heat with its surroundings, may be engineered or tuned according to the present invention. By way of second non-limiting example, the thermal conductivity of the fungal textile material, i.e. the quantity of heat transferred through the fungal textile material, may be engineered or tuned according to the present invention. By way of third non-limiting example, the heat capacity, i.e. the amount of heat to be supplied to a given mass of the fungal textile material to produce a unit change in its temperature, may be engineered or tuned according to the present invention. The volumetric heat capacity of the fungal textile material, i.e. the quantity of heat a volume of the fungal textile material can store, may be engineered or tuned according to the present invention. The ability to thermally engineer and/or tune the fungal textile materials allow the fungal textile material to have a desired "heat feel" and thus represents a major improvement over fungal or other non-animal textile materials of the prior art, which frequently suffer from a drawback of "feeling cold" (i.e. having poor thermal properties) to a user and/or offering insufficient insulation, e.g. to a wearer of an article of clothing made from the fungal textile material; the present invention thus allows for the creation of, e.g., fungal textiles that retain a greater quantity of heat and are thus suitable for use in articles of winter clothing. One further advantage and benefit of the present invention lies in the ability to produce textile materials that may have a combination of two or more of these or other thermal properties not achievable by conventional textile materials, e.g. it is possible to increase one thermal property while increasing, holding constant, or decreasing one or more other thermal properties, and/or it is possible to hold one thermal property constant while increasing, holding constant, or decreasing one or more other thermal properties, and/or it is possible to decrease one thermal property while increasing, holding constant, or decreasing one or more other thermal properties.

Thermal properties of fungal textile materials of the present invention may be engineered or tuned by including in the fungal textile material a thermal dopant. Thermal dopants suitable for use in the fungal textile materials of the present invention include materials that modify one or more of thermal effusivity, thermal conductivity, and heat capacity of the fungal textile material, as compared to the fungal textile material in the absence of the thermal dopant. Such thermal dopants may comprise, but are not necessarily limited to, polymeric, ceramic, and metallic materials having known thermal properties, and/or any other material having a desired thermally conductive and/or thermally insulative property. Further non-limiting examples of thermal dopants suitable for use in the present invention include activated charcoal, aluminum oxide, bentonite, diatomaceous earth, ethylene vinyl acetate, lignin, nanosilica, polycaprolactone, polylactic acid, silicone, and yttrium oxide. In some embodiments, the thermal dopant may comprise an engineered coating and/or an engineered spatial distribution of thermally conductive and/or thermally insulative materials throughout the fungal textile material to produce a preselected thermal profile.

In the practice of the present invention, thermal dopants may be added and/or introduced into the fungal textile material at any suitable point in the manufacturing method. As a first non-limiting example, a thermal dopant may be provided in the polymer solution, i.e. combined with the polymer and solvent before being subsequently combined with a fungal biomass. As a second non-limiting example, a thermal dopant may be combined with the inactivated fungal biomass, water, and optional pigment before or during a size-reducing and/or blending/homogenizing step of the manufacturing method. As a third non-limiting example, a thermal dopant may be added to the mixture of the fungal paste and the polymer solution while the paste/polymer solution mixture is being stirred and/or heated. As a fourth non-limiting example, a thermal dopant, and in some embodiments an engineered or designed spatial pattern or structure of a thermal dopant, may be integrated with the fungal textile material. As a fifth non-limiting example, a thermal dopant may be added before or during a casting step, e.g. by providing the thermal dopant in a tray or mold in which the sheet is to be cast or by sprinkling or otherwise distributing particles of a dopant over a surface of the fungal material after casting. As a sixth non-limiting example, a thermal dopant may be added to the fungal textile material after the fungal textile material has been cured.

The amount of the thermal dopant may be selected to provide a desired thermal property to the resulting fungal textile material without compromising other material properties (e.g. flexibility, tensile strength, etc.) of the fungal textile material. Typically, thermal dopants, when provided, may make up between about 0.1 wt % and about 25%, or any sub-range between those values, of the fungal textile material. In some embodiments, the dopants may be present at about 0.1 to about 20 wt %, or at about 0.1 to about 15 wt % of the fungal textile material. For instance, in various embodiments, the dopants may make up about 1 wt %, about 2 wt %, about 3 wt %, about 4 wt %, about 5 wt %, about 6 wt %, about 7 wt %, about 8 wt %, about 9 wt %, about 10 wt %, about 11 wt %, about 12 wt %, about 13 wt %, about 14 wt %, about 15 wt %, or any tenth of a weight percent between 0.1 and 25, of the fungal textile material.

In embodiments, the fungal composition formed after mixing with the polymer solution may be cast to at least partially overlie a scaffold or substrate comprising a thermal dopant. In embodiments, a force may be applied to at least one of the fungal composition and the scaffold or substrate to provide a heterogeneous spatial distribution of the fungal composition and the scaffold or substrate in the cast sheet. In embodiments, the fungal composition and a thermal dopant may each be selectively applied to predetermined regions of a casting area to provide a heterogeneous spatial distribution of the blended composition and the thermal dopant in the cast sheet. In embodiments, the cast sheet may comprise a multilayer structure having at least a first layer and a second layer, the first layer comprising at least a portion of the fungal composition and the second layer comprising at least a portion of the thermal dopant.

Embodiments of the present invention include articles of clothing partially or completely constructed of a fungal textile material of the invention. Such articles of clothing include, by way of non-limiting example, protective garments, shirts, pants, shorts, jackets, coats, belts, hats, gloves, shoes, boots, sandals, flip-flops, watch straps, and aprons.

Embodiments of the present invention include accessory items partially or completely constructed of a fungal textile material of the invention. Such accessory items include, by way of non-limiting example, wallets, purses, cases, suitcases, luggage items, bags, backpacks, and hip packs.

Embodiments of the present invention include furniture items partially or completely constructed of a fungal textile material of the invention. Such furniture items include, by way of non-limiting example, chairs, recliners, couches, sofas, loveseats, and ottomans.

Embodiments of the present invention include coverings partially or completely constructed of a fungal textile material of the invention. Such coverings include, by way of non-limiting example, coverings for automobile seats, airplane seats and train seats.

Fungal textile materials according to the present invention may be manufactured such that they are characterized by a desired material, mechanical, and/or physical property. As a first non-limiting example, fungal textile materials may be manufactured to have a desired tensile strength, which may in embodiments be at least about 15 MPa or between about 4 MPa and about 15 MPa., or any sub-range between those values. As a second non-limiting example, fungal textile materials may be manufactured to have a desired strain at break, which may in embodiments be between about 50 percent and about 60 percent, or between about 10 percent and about 70 percent, or any sub-range between those values. As a third non-limiting example, fungal textile materials may be manufactured to have a desired degree of swelling, which may in embodiments be between about 50 percent and about 60 percent, or between about 30 percent and about 120 percent, or any sub-range between those values. As a fourth non-limiting example, fungal textile materials may be manufactured to have a desired mass loss upon soaking, which may in embodiments be no more than about 5 percent. As a fifth non-limiting examples, fungal textile materials may be manufactured to have a desired average fungal particle size, which may in embodiments be no more than about 25 nanometers, no more than about 50 nanometers, no more than about 75 nanometers, no more than about 100 nanometers, no more than about 125 nanometers, no more than about 150 nanometers, no more than about 175 nanometers, no more than about 200 nanometers, no more than about 225 nanometers, no more than about 250 nanometers, no more than about 275 nanometers, no more than about 300 nanometers, no more than about 325 nanometers, no more than about 350 nanometers, no more than about 375 nanometers, no more than about 400 nanometers, no more than about 425 nanometers, no more than about 2 micrometers, no more than about 4 micrometers, no more than about 6 micrometers, no more than about 8 micrometers, no more than about 10 micrometers, no more than about 15 micrometers, no more than about 20 micrometers, no more than about 30 micrometers, no more than about 40 micrometers, no more than about 50 micrometers, no more than about 75 micrometers, no more than about 100 micrometers, no more than about 150 micrometers, no more than about 200 micrometers, no more than about 250 micrometers, no more than about 300 nanometers, no more than about 400 micrometers, no more than about 500 micrometers and no more than about 750 micrometers. In some embodiments, the fungal biomass may comprise fungal filaments having a length of at least about 1 centimeter, at least about 2 centimeters, at least about 3 centimeters, at least about 4 centimeters, at least about 5 centimeters, at least about 6 centimeters, at least about 7 centimeters, at least about 8 centimeters, at least about 9 centimeters, at least about 10 centimeters, at least about 20 centimeters, at least about 30 centimeters, at least about 40 centimeters, at least about 50 centimeters, at least about 60 centimeters, at least about 70 centimeters, at least about 80 centimeters, or at least about 90 centimeters. As a sixth non-limiting example, fungal textile materials may be manufactured to have a desired type of particle size distribution, which may in embodiments be a bimodal, approximately bimodal, trimodal, or approximately trimodal particle size distribution. As a seventh non-limiting example, fungal textile materials may be manufactured to have a desired tear strength, which may in embodiments be between about 5 N/mm and about 25 N/mm, or any sub-range between those values. As an eighth non-limiting example, fungal textile materials may be manufactured to have a desired color fastness to wet rub, dry rub, and/or xenon light of at least about 4 in grey scale. As a ninth non-limiting example, fungal textile materials may be manufactured to have a desired flexural rigidity, which may in embodiments be no more than about 5 gram-centimeters. One of the advantages and benefits of the present invention lies in the ability to produce textile materials that may have a combination of two or more of these or other material, mechanical, and/or physical properties not achievable by conventional textile materials, e.g. a combination of high tear strength (in some embodiments, at least about 1 N/mm, or at least about 2 N/mm, or at least about 3 N/mm, or at least about 4 N/mm, or at least about 5 N/mm, or at least about 6 N/mm, or at least about 7 N/mm, or at least about 8 N/mm, or at least about 9 N/mm, or at least about 10 N/mm, or at least about 11 N/mm, or at least about 12 N/mm, or at least about 13 N/mm, or at least about 14 N/mm, or at least about 15 N/mm, or at least about 16 N/mm, or at least about 17 N/mm, or at least about 18 N/mm, or at least about 19 N/mm, or at least about 20 N/mm) and low flexural rigidity (in some embodiments, no more than about 10 gram-centimeters, or no more than about 9 gram-centimeters, or no more than about 8 gram-centimeters, or no more than about 7 gram-centimeters, or no more than about 6 gram-centimeters, or no more than about 5 gram-centimeters, or no more than about 4 gram-centimeters, or no more than about 3 gram-centimeters, or no more than about 2 gram-centimeters, or no more than about 1 gram-centimeter).

In some embodiments, a fungal leather analog material made from a size-reduced inactivated fungal biomass and being devoid of any non-fungal textile backing may be provided. Such fungal leather analog materials may have any one or more of the following properties: a thickness of between about 1 and about 2 mm or between about 1.15 and about 1.6 mm, a tear strength of between about 6 and about 12 N or between about 7.4 and about 10.5 N, a tensile strength of between about 3 and about 10 N/mm$^2$ or between about 4.7 and about 8.1 N/mm$^2$, a flexural rigidity of between about 1 and about 11 g·cm, a water spotting grey scale rating of 4 to 5, a light color fastness blue wool rating of at least 4, a rub color fastness grey scale rating when dry of 4 to 5, and a rub color fastness grey scale rating when dry of 4 to 5. Such fungal leather analog materials can easily take on various textures or embossments.

In some embodiments, a fungal leather analog material made from a size-reduced inactivated fungal biomass and having a non-fungal textile backing adhered on one side may be provided. Such fungal leather analog materials may have any one or more of the following properties: a thickness of between about 1 and about 3 mm or between about 1.95 and about 2.09 mm, a tear strength of between about 20 and about 50 N or between about 33 and about 37 N, a tensile strength of between about 3 and about 10 N/mm$^2$ or between about 5.8 and about 6.8 N/mm$^2$, a flexural rigidity of between about 1 and about 11 g·cm, a water spotting grey scale rating of 4 to 5, a light color fastness blue wool rating of at least 4, a rub color fastness grey scale rating when dry of 4 to 5, and a rub color fastness grey scale rating when dry of 4 to 5. Such fungal leather analog materials can easily take on various textures or embossments.

In some embodiments, a composite fungal leather analog material made from a size-reduced inactivated fungal biomass and having a non-fungal textile layer adhered between two layers of fungal material (i.e. a material in which the non-fungal layer is "sandwiched" between fungal layers) may be provided. Such fungal leather analog materials may have any one or more of the following properties: a thickness of between about 1 and about 4 mm or between about 2.2 and about 2.8 mm, a tear strength of between about 25 and about 60 N or between about 34 and about 52 N, a tensile strength of between about 7 and about 14 N/mm$^2$ or between about 8.7 and about 11.4 N/mm$^2$, a flexural rigidity of between about 1 and about 11 g·cm, a water spotting grey scale rating of 4 to 5, a light color fastness blue wool rating of at least 4, a rub color fastness grey scale rating when dry of 4 to 5, and a rub color fastness grey scale rating when dry of 4 to 5. Such fungal leather analog materials can easily take on various textures or embossments.

In some embodiments, a fungal leather analog material made from an inactivated fungal biomass taking the form of one or more intact or whole biomats (e.g. a biomass produced by surface fermentation and not subjected to size reduction) and being devoid of any non-fungal textile backing may be provided. Such fungal leather analog materials may have any one or more of the following properties: a thickness of between about 0.1 and about 1.5 mm per biomat or between about 0.5 and about 0.9 mm per biomat, a tear strength of between about 1 and about 3 N per biomat, a tensile strength of about 3 N/mm$^2$ per biomat, a flexural rigidity of between about 1 and about 11 g·cm, and a water spotting grey scale rating of 4 to 5. Such fungal leather analog materials can have advantages such as warmth, drapability, softness, appearance, and smell that closely mimic the same qualities of true leather.

In some embodiments, fungal leather analog materials made from inactivated fungal biomass, and methods of manufacture thereof, may provide environment advantages and benefits relative to true leather in addition to the non-use of animal products. Particularly, the methods of manufacture of the present invention may generate no, or at least smaller quantities of, highly toxic or environmentally hazardous materials used in traditional leather tanning processes, such as hexavalent chromium compounds. Additionally, leather analog materials according to the present invention may be biodegradable, i.e. biodegrade more quickly under a given set of conditions than true leather.

One feature of the invention is the ability to permit various chemical components (a polymer, a crosslinker, etc.) to infiltrate the mycelial matrix of an inactivated fungal biomass. Where the inactivated fungal biomass is a size-reduced fungal biomass, this infiltration may be the result of the high surface area of fungal particles in contact with the infiltrating fluid(s). Where the inactivated fungal biomass is an intact or cohesive fungal biomass (e.g. a biomat produced by surface fermentation), this infiltration may be achieved by any one or more of an extended time of contact between the fungal biomass and the fluid(s), agitation of the fungal biomass together with the fluid(s), application of sub- or superatmospheric pressure to the fungal biomass and the fluid(s), and so on.

It is one aspect of the present invention to provide a method for preparing a durable sheet material comprising fungal biomass, comprising (a) combining an inactivated fungal biomass with at least one component selected from the group consisting of a plasticizer, a polymer, a crosslinker, and a dye to form a combined composition; (b) casting the combined composition to form a cast sheet; (c) removing solvent from the cast sheet; and (d) curing the cast sheet to form the durable sheet material. It is to be expressly understood that this method can be used in conjunction with either intact cohesive biomass (e.g. a biomat produced by surface fermentation) or size-reduced fungal biomass.

In embodiments, step (d) may comprise drying the cast sheet.

In embodiments, step (d) may comprise initiating a chemical reaction within or on a surface of the cast sheet.

In embodiments, the method may further comprise adding at least one of a natural fiber material, a synthetic material, and combinations thereof to the blended composition. The natural fiber material may, but need not, comprise a cellulosic material. The natural fiber material may, but need not, comprise cotton fiber. The at least one of the natural fiber material and the synthetic material may, but need not, be in the form of a plurality of particles, a sheet, or a combination thereof.

In embodiments, the method may further comprise inactivating a fungal biomass to form the inactivated fungal biomass.

In embodiments, the method may further comprise size-reducing a fungal biomass.

In embodiments, the method may further comprise adding a thermal dopant to at least one of the inactivated fungal biomass, the blended composition, and the cast sheet.

It is another aspect of the present invention to provide a method for preparing a durable sheet material comprising fungal biomass, comprising (a) contacting an inactivated fungal biomass with a solution comprising at least one component selected from the group consisting of a plasticizer, a polymer, a crosslinker, and a dye; (b) removing a solvent from the biomass; and (c) curing the biomass to form the durable sheet material.

In embodiments, the method may further comprise inactivating a fungal biomass to form the inactivated fungal biomass.

It is another aspect of the present invention to provide a textile composition, comprising an inactivated fungal biomass; and at least one component selected from the group consisting of a plasticizer, a polymer, a crosslinker, and a dye.

In embodiments, the textile composition may comprise a plasticizer, a polymer, and a crosslinker.

In embodiments, the fungal biomass may comprise a fungus belonging to a phylum selected from the group consisting of Ascomycota and Basidiomycota.

In embodiments, the fungal biomass may comprise a fungus belonging to a genus selected from the group consisting of *Fusarium, Fomes*, and *Ganoderma*. The fungus may, but need not, belong to a species selected from the group consisting of *Fusarium venenatum, Fomes fomentarius, Ganoderma applanatum, Ganoderma curtisii, Ganoderma formosanum, Ganoderma nei-japonicum, Ganoderma resinaceum, Ganoderma sinense*, and *Ganoderma tsugae*.

In embodiments, the fungal biomass may comprise a fungus selected from the group consisting of *Fusarium venenatum* and MK7 ATCC Accession Deposit No. PTA-10698.

In embodiments, the plasticizer may comprise at least one selected from the group consisting of glycerol, polyethylene glycol, citric acid, and oleic acid. The plasticizer may, but need not, comprise glycerol. The glycerol may, but need not, be present in the textile composition in an amount of between about 0.5 wt % and about 50 wt %. %, or any sub-range between those values. In embodiments, the glycerol may, but need not, be present in an amount of about 50 wt %, about 37.5 wt %, about 25 wt %, or about 12.5 wt %.

In embodiments, the polymer may comprise at least one selected from the group consisting of polyvinyl alcohol, chitosan, polyethylene glycol, and hyaluronic acid. The polymer may, but need not, comprise polyvinyl alcohol. The polymer may, but need not, comprise chitosan. The polymer may, but need not, comprise polyvinyl alcohol and chitosan. A weight ratio of polyvinyl alcohol to chitosan may, but need not, be selected from the group consisting of about 99:1, about 90:10, about 80:20, about 70:30, about 60:40, about 50:50, about 40:60, about 30:70, about 20:80, about 10:90, and about 1:99 or any range formed by two of those ratios. The weight ratio of polyvinyl alcohol to chitosan may, but need not, be about 50:50.

In embodiments, the textile composition may comprise a polymer, wherein a loading ratio of the textile composition is selected from the group consisting of about 99:1, about 95:5, about 90:10, about 85:15, about 80:20, about 75:25, about 70:30, about 65:35, about 60:40, about 55:45, about 50:50, about 45:55, about 40:60, about 35:65, about 30:70, about 25:75, about 20:80, about 15:85, about 10:90, about 5:95, and about 1:99 or any range formed by two of those ratios. The loading ratio may, but need not, be about 70:30.

In embodiments, the crosslinker may comprise at least one selected from the group consisting of citric acid, tannic acid, suberic acid, adipic acid, succinic acid, glyoxal, and extracted vegetable tannins. The crosslinker may, but need not, comprise adipic acid.

It is another aspect of the present invention to provide an article of clothing, comprising a textile composition of the invention.

In embodiments, the article may be a protective garment.

In embodiments, the article of clothing may be selected from the group consisting of a shirt, a pant, a short, a jacket, a coat, a belt, a hat, a glove, a shoe, a boot, a sandal, a flip-flop, a watch strap, and an apron.

It is another aspect of the present invention to provide an accessory item, comprising a textile composition of the invention.

In embodiments, the accessory item may be selected from the group consisting of a wallet, a purse, a case, a suitcase, a luggage item, a bag, a backpack, and a hip pack.

It is another aspect of the present invention to provide a furniture item, comprising a textile composition of the present invention.

In embodiments, the furniture item may be selected from the group consisting of a chair, a recliner, a couch, a sofa, a loveseat, an ottoman, and a vehicle seat.

In embodiments, the textile composition may have a tensile strength of at least about 15 MPa.

In embodiments, the textile composition may have a strain at break of between about 30 percent and about 60 percent.

In embodiments, the textile composition may have a degree of swelling of between about 30 percent and about 60 percent.

In embodiments, the textile composition may have a mass loss upon soaking of no more than about 30 percent.

In embodiments, the fungal biomass may have an average particle size selected from the group consisting of no more than about 25 nanometers, no more than about 50 nanometers, no more than about 75 nanometers, no more than about 100 nanometers, no more than about 125 nanometers, no more than about 150 nanometers, no more than about 175 nanometers, no more than about 200 nanometers, no more than about 225 nanometers, no more than about 250 nanometers, no more than about 275 nanometers, no more than about 300 nanometers, no more than about 325 nanometers, no more than about 350 nanometers, no more than about 375 nanometers, no more than about 400 nanometers, no more than about 425 nanometers, no more than about 2 micrometers, no more than about 4 micrometers, no more than about 6 micrometers, no more than about 8 micrometers, no more than about 10 micrometers, no more than about 15 micrometers, no more than about 20 micrometers, no more than about 30 micrometers, no more than about 40 micrometers, no more than about 50 micrometers, no more than about 75 micrometers, no more than about 100 micrometers, no more than about 150 micrometers, no more than about 200 micrometers, no more than about 250 micrometers, no more than about 300 nanometers, no more than about 400 micrometers, no more than about 500 micrometers and no more than about 750 micrometers.

In embodiments, the fungal biomass may have a bimodal or approximately bimodal particle size distribution.

In embodiments, the fungal biomass may have a trimodal or approximately trimodal particle size distribution.

In embodiments, the textile composition may comprise transglutaminase.

In embodiments, the textile composition may comprise proteins crosslinked with isopeptide bonds. Formation of the crosslinking isopeptide bonds may, but need not, be catalyzed by transglutaminase.

In embodiments, the textile composition may further comprise a thermal dopant. The thermal dopant may, but need not, be selected from the group consisting of activated charcoal, aluminum oxide, bentonite, diatomaceous earth, lignin, nanosilica, polycaprolactone, polylactic acid, silicone, and yttrium oxide.

It is another aspect of the present invention to provide a method for preparing a durable sheet material comprising fungal biomass, comprising (a) homogenizing an inactivated fungal biomass with a fluid comprising water to form a fungal paste; (b) combining the fungal paste with an aqueous solution comprising a polymer to form a blended composition; (c) casting the blended composition to form a cast sheet; (d) removing solvent from the cast sheet; and (e) curing the cast sheet to form the durable sheet material. It is to be expressly understood that fungal biomass suitable for use in this method may be produced by any of a number of methods known in the art and disclosed herein, including but not limited to surface fermentation methods, submerged fermentation methods, solid-substrate submerged fermentation (SSSF) methods, and methods as disclosed in the '474 publication.

In embodiments, the fluid of step (a) may further comprise a pigment.

In embodiments, the method may further comprise inactivating a fungal biomass to provide the inactivated fungal biomass.

In embodiments, step (a) may further comprise simultaneously size-reducing the inactivated fungal biomass.

In embodiments, the inactivated fungal biomass may be a size-reduced fungal biomass.

In embodiments, the polymer may comprise chitosan.

In embodiments, the aqueous solution of step (b) may further comprise at least one of a crosslinker, a plasticizer, a solubilizer, and a pH adjusting agent. The aqueous solution may, but need not, comprise a crosslinker, wherein the crosslinker comprises citric acid. The aqueous solution may, but need not, comprise a plasticizer, wherein the plasticizer comprises glycerol.

In embodiments, the method may further comprise, between steps (a) and (b), degassing the fungal paste.

In embodiments, the method may further comprise, between steps (b) and (c), degassing the blended composition.

In embodiments, the method may further comprise adding at least one thermal dopant to at least one of the inactivated fungal biomass, the fluid of step (a), the fungal paste, the aqueous solution of step (b), the blended composition, the cast sheet, and a tray, mold, or other vessel into which the blended composition is cast in step (c).

In embodiments of any of the above methods, the fungal biomass may be produced by a method comprising culturing a fungal inoculum by at least one of surface fermentation, submerged fermentation, solid-substrate submerged fermentation, and a fermentation method as described in the '474 publication. The fungal biomass may, but need not, be a biomat.

Embodiments of any of the above methods may further comprise maintaining or introducing at least one bubble of a gas.

Embodiments of the above textile compositions may comprise at least one bubble of a gas.

In embodiments, the fungal biomass may comprise fungal filaments having a length of at least about 1 centimeter, at least about 2 centimeters, at least about 3 centimeters, at least about 4 centimeters, at least about 5 centimeters, at least about 6 centimeters, at least about 7 centimeters, at least about 8 centimeters, at least about 9 centimeters, at least about 10 centimeters, at least about 20 centimeters, at least about 30 centimeters, at least about 40 centimeters, at least about 50 centimeters, at least about 60 centimeters, at least about 70 centimeters, at least about 80 centimeters, at least about 90 centimeters, at least about 100 centimeters, at least about 200 centimeters, at least about 300 centimeters, at least about 400 centimeters, at least about 500 centimeters, at least about 600 centimeters, at least about 700 centimeters, at least about 800 centimeters, or at least about 900 centimeters.

In embodiments, the fungal biomass may comprise fungal filaments having a length of no more than about 1 centimeter, no more than about 9 millimeters, no more than about 8 about millimeters, no more than about 7 millimeters, no more than about 6 millimeters, no more than about 5 millimeters, no more than about 4 millimeters, no more than about 3 millimeters, no more than about 2 millimeters, no more than about 1 millimeter, no more than about 900 micrometers, no more than about 800 micrometers, no more than about 700 micrometers, no more than about 600 micrometers, no more than about 500 micrometers, no more than about 400 micrometers, no more than about 300 micrometers, no more than about 200 micrometers, no more than about 100 micrometers, no more than about 90 micrometers, no more than about 80 micrometers, no more than about 70 micrometers, no more than about 60 micrometers, no more than about 50 micrometers, no more than about 40 micrometers, no more than about 30 micrometers, no more than about 20 micrometers, no more than about 10 micrometers, no more than about 9 micrometers, no more than about 8 micrometers, no more than about 7 micrometers, no more than about 6 micrometers, no more than about 5 micrometers, no more than about 4 micrometers, no more than about 3 micrometers, no more than about 2 micrometers, or no more than about 1 micrometer.

The invention is further illustratively described by way of the following non-limiting Examples.

Example 1

Textile Material Manufacturing Process

Fungal textile materials according to the present invention may, in embodiments, be made according to the methods described in this Example. In particular, the methods described in this Example may be employed to manufacture a leather analog textile material, i.e. a fungal textile material that may replicate, simulate, and/or substitute for true leather.

The first step or steps in these methods of making a fungal textile material generally include obtaining a mat of fungal material, comprising fungal mycelia, from a suitable reactor, which may in embodiments entail producing a fungal biomat according to the methods described in the '050 application, the '626 application, the '421 application, and/or the '474 publication. These mats are then inactivated, in some embodiments by steaming for not less than 30 minutes, and the inactivated mat may then be cut into a desired size and geometry. In some embodiments, the mat may be partially or completely dried in a dehydrator at elevated temperature, e.g. between about 130° F. and about 160° F.

The inactivated mat is then placed into a solution of one or more components selected to impart a desired characteristic to the final fungal textile material. Generally, the solution comprises one or more of a polymer, a plasticizer, and a crosslinker. Polymers suitable for use in solution according to the present invention include but are not limited to polyvinyl alcohol, chitosan, polyethylene glycol, hyaluronic acid, polycaprolactones, polyacrylic acids, and combinations and mixtures thereof. Plasticizers suitable for use in solution according to the present invention include but are not limited to glycerol and esters thereof, polyethylene glycol, citric acid, oleic acid, oleic acid polyols (e.g. mannitol, sorbitol) and esters thereof, epoxidized triglyceride vegetable oils (e.g. from soybean oil), castor oil, pentaerythritol, fatty acid esters, carboxylic ester-based plasticizers, trimellitates, adipates, sebacates, maleates, biological plasticizers, and combinations and mixtures thereof. Crosslinkers suitable for use in solution according to the present invention include but are not limited to citric acid, tannic acid, suberic acid, adipic acid, succinic acid, extracted vegetable tannins, glyoxal, and combinations and mixtures thereof.

The inactivated mat is allowed to soak in the polymer, plasticizer, and/or crosslinker solution for a time sufficient to allow the mat to be penetrated by and/or saturated with the polymer, plasticizer, and/or crosslinker, generally at least about two hours and most typically about 24 hours. After soaking in the solution, the wet mat is removed from the solution (whereupon excess solution may be removed from one or more surfaces of the mat).

An optional step in the methods of the present invention, which may be preferable in some embodiments, includes lamination of two or more mats after soaking. In the practice of the present invention, mats may be laminated by vertically stacking two or more mats or arranging the mats in any desired spatial orientation (horizontal vs. vertical, parallel vs. perpendicular vs. oblique, etc.), which may in some cases include natural fibers in addition to the fungal mycelia, and soaking the vertically stacked mats in a polymer solution, which may be the same as or different from the solution used for the earlier soaking step. Generally, lamination of two or more mats according to the present invention includes the removal of air bubbles trapped between layers, e.g. by pressing the stacked mats, by rolling, by vacuum extraction, etc.

Wet mats (or laminates of mats) are then dried, generally for between about 30 minutes and about 120 minutes, in a dehydrator at elevated temperature, e.g. between about 130° F. and about 160° F., to remove substantially all of the liquid from an outer surface of the mat (or laminate) but retain at least some liquid in an interior of the mat (or laminate). The mats are then removed from the dehydrator and, in some embodiments, heat-pressed, e.g. between textured silicon molds, at elevated temperature (e.g. about 130° C.); typically, mats are heat-pressed in intervals of between about 20 seconds and about 30 seconds for a total time of between about 3 minutes and about 10 minutes.

Example 2

Fungal Growth Through Fibers

Fungal textile materials according to the present invention may, in embodiments, be made according to the methods described in this Example. In particular, the methods described in this Example may be employed to manufacture a textile material that incorporates both filamentous fungus and other natural or synthetic fibers.

The first step or steps in these methods of making a fungal textile material generally include providing a growth medium for filamentous fungus, which may in embodiments include growth media as described in the '050 application, the '626 application, the '421 application, and/or the '474 publication, but which may also include other types of growth medium. Particularly, a growth medium may be formulated with an alternative carbon source or different carbon content, which may in embodiments promote the consumption of natural fibers by the fungus to be cultured in the growth medium. By way of non-limiting example, conventional growth media may be altered by replacing glycerol with hydrolyzed cellulose, crystalline cellulose, or other cellulosic compounds to promote production of cellulase enzymes by the filamentous fungus. By way of further non-limiting example, the total amount of cellulosic material may be carefully controlled, e.g. to about 10 wt % of the growth medium, to provide for desired growth characteristics of the filamentous fungus. After the growth medium is prepared, it is generally boiled for a period of no less than 30 minutes to eliminate competitive or pathogenic microorganisms, then sealed and left to cool. The cooled medium is typically pH adjusted, e.g. using hydrogen chloride, and inoculated with an inoculum of a filamentous fungus (e.g. MK7 ATCC Accession Deposit No. PTA-10698) at a rate of about 5 vol %; the medium is generally stirred to provide uniform dispersal of the fungal inoculum.

A reactor for the production of filamentous fungus biomass is prepared by providing a sanitary reactor, e.g. a Saran wrap reactor or the like, and cleaning and/or sterilizing an interior (e.g. walls, doors, racks, trays, etc.) of the reactor (e.g. with ethanol). Separately, natural fibers which are to serve as a substrate and/or structural material for the fungal textile material are placed into one or more Pyrex trays, generally at a rate of about 0.5 grams to about 5 grams per tray, covered in aluminum foil, and dry-autoclaved to eliminate competitive or pathogenic microorganisms, then allowed to cool; the Pyrex trays are then placed into the cleaned reactor (generally onto trays of the reactor).

The inoculated medium is then poured or otherwise introduced into the Pyrex trays in the reactor, generally at a rate of about 200 mL per tray. It is generally desirable to introduce the inoculated medium into a corner of the Pyrex tray rather than its center, to allow the growth medium to flow beneath the fibers within the Pyrex tray and thus to allow the fibers to float on the surface of the liquid medium. After an incubation period, generally between about three days and about three weeks, each Pyrex tray contains a fungal biomass grown through the natural substrate and/or structural fibers, which may then be harvested for further processing.

Example 3

Incorporation of Oil(s)

In the production of true (i.e. non-fungal) leather, the leather material is generally subjected to an oiling process, whereby the leather material is coated with one or more oils, or more commonly with a mixture of oil(s), an emulsifier, and a penetrating aid. This oiling process lubricates the leather and improves its ability to flex without cracking (dry leather fibers generally crack or break easily) and may also impart color and water resistance to the leather material. In the practice of the present invention, oils may be likewise incorporated into fungal leather analog materials, or produced in situ by the filamentous fungus itself during a fermentation process, to provide similar advantages and benefits. This Example describes embodiments of such oil incorporation processes for fungal leather analog materials.

In "emulsion" oil incorporation methods according to the present invention, one or more oils, fats, and/or waxes are provided. The oils, fats, and/or waxes may be selected for their utility as emulsifiers and/or surfactants (e.g. salts, soaps, and other amphiphilic molecules), and may include, by way of non-limiting example, any one or more of sulfated castor oil, beeswax, coconut oil, vegetable oil, olive oil, linseed oil and oleic acid sulfated fish oil, sulfated canola oil, soybean oil, palm oil, fatty acids. Emulsions formed with the aid of surfactants may provide more stable conditions for penetration of the leather; those of ordinary skill in the art can select an anionic, cationic, or non-ionic surfactant to improve the wetting action of the emulsion on the fibers of the leather material. These oils, fats, and/or waxes are rapidly stirred in a vessel (e.g. via magnetic stir bar), and in some embodiments heat may be applied to melt one or more of the oils, fats, and/or waxes to ensure complete mixing, while water (preferably deionized water) is gradually added to the mixture until a milky emulsion is formed; most typically, water makes up between about 50 vol % and about 70 vol % of this emulsion. The stirring rate is subsequently reduced (e.g. via magnetic stir bar or orbital shaker), whereupon fungal leather analog materials according to the present invention are introduced to the vessel. The fungal leather analog materials are generally allowed to remain in the agitated emulsion for a period of between about 20 minutes and about four hours, then removed from the emulsion and allowed to air-dry for between about 24 hours and about 48 hours. This oiling process may be carried out before, after, and/or in lieu of heat-pressing of the fungal leather analog material.

In "stuffing" oil incorporation methods according to the present invention, one or more liquefied oils or waxes, including but not limited to oils or waxes suitable for use in the "emulsion" method described above, may be mechanically rubbed onto the surface of a fungal leather analog material to "work" the oils or waxes into the structure of the fungal leather analog material. As in the "emulsion" method, the fungal leather analog material is then allowed to air-dry for between about 24 hours and about 48 hours, and the "stuffing" oiling process may be carried out before, after, and/or in lieu of heat-pressing of the fungal leather analog material.

Example 4

Vegetable Tanning

In the practice of the present invention, the use of a dicarboxylic acid as the crosslinker generally necessitates heat-pressing of the fungal textile material because crosslinking of carboxylic acids to the chemical moieties found in the fungal textile material generally occurs only at elevated temperature (e.g. about 130° C.). As an alternative, natural tannins, such as tannins extracted from vegetable material or other plant material, may bond to and/or induce chemical bonding in (i.e. crosslink) the fungal textile material at lower temperature than dicarboxylic acids and thus eliminate the need for heat-pressing, which may improve the water resistance of the fungal textile material. Without wishing to be bound by any particular theory, it is believed that tannins interact with fungal textile materials in much the same way that they interact with animal hides or skins, i.e. bonding with protein moieties to improve the strength and degradation resistance of the material.

Elimination of the need to heat-press the fungal textile material may have further advantages and benefits for downstream processing. By way of non-limiting example, oil incorporation processes (such as those described in Example 3) typically require a relatively "open" structure of the fungal textile material; heat-pressing closes the structure of the fungal textile material and thus makes it difficult for the oil to penetrate into the leather structure, and while the oil incorporation process may be performed before heat-pressing, this can in some cases interfere with crosslinking reactions and/or cause oils to leach from the fungal textile material during heat-pressing. This Example describes embodiments of a process for crosslinking a fungal textile material using vegetable tannins to avoid these and other drawbacks.

In vegetable tanning methods according to the present invention, mats of fungal biomass are produced by any suitable method, including but not limited to methods as disclosed herein and/or in the '050 application, the '626 application, and/or the '421 application, and steamed as described in Example 1. The steamed mats are washed one or more times with deionized water, brine, or a combination or mixture thereof, and the washed mats are then placed in a solution containing tannin compounds. The tannin compounds may comprise any one or more commercial plant-extracted tannins and/or pure tannic acid, and generally make up between about 0.5 wt % and about 20 wt % of the tanning solution. The fungal mats are generally allowed to remain in the tanning solution for between about one day and about 30 days, and in some embodiments the fungal mats may be transferred between two or more tanning solutions, e.g. tanning solutions having different compositions and/or concentrations of tannin compounds, during the tanning process.

After tanning, the fungal mats may be oiled by any suitable method, e.g. one or both of the methods described in Example 3, and/or may be subjected to a plasticizing solution or process (e.g. using polyethylene glycol (PEG) and/or glycerol as a plasticizer). The plasticized and/or oiled material is finally allowed to air-dry, generally for between about 24 hours and about 72 hours. It is to be expressly understood that further crosslinking, e.g. using dicarboxylic acids as crosslinkers, may, in embodiments, be performed after the vegetable tanning process described in this Example.

Example 5

Effects of Polymer-Plasticizer Ratio on Textile Material Properties

This Example describes the effect of a ratio of polymer to plasticizer in the solution of the present invention on material properties of fungal textile materials, and fungal leather analog materials particularly. Polymers (i.e. long-chain molecules chemically bonded to biological structures within the fungal textile material) improve the tensile strength of the fungal textile material, whereas plasticizers (i.e. smaller molecules that do not chemically bond to the biological structures or the polymers) improve the flexibility and decrease the brittleness of the fungal textile material. Thus, without wishing to be bound by any particular theory, it is believed that varying a polymer-to-plasticizer ratio (hereinafter "PP ratio") may enable those of ordinary skill in the art to precisely control, select, or tune physical properties of fungal textile materials produced according to the present invention.

Biomats of MK7 ATCC Accession Deposit No. PTA-10698 (hereinafter "MK7") were grown and steamed or boiled for 30 minutes to inactivate the fungus. The inactivated biomats were cut into approximately 4 cm×6 cm rectangles, each of which was placed into a solution comprising both a polymer (either polyvinyl alcohol (PVA) or chitosan) and a plasticizer (glycerol) and left to soak overnight. After soaking, each rectangle was dried for between about 45 minutes and about one hour in a tabletop dehydrator, then heat-pressed at 275° F. in 30-second intervals for a total of four minutes. The samples were then air-dried at room temperature overnight and subsequently tested for degree of swelling (DOS), mass loss upon soaking (ML), tensile strength (TS), and subjective flexibility (six evaluations, 0-10 scale). The results are presented in Table 1.

to 8.61 MPa) and the wide range of flexibilities (0.67 to 9.83 on a subjective 0-10 scale) obtained by varying concentration of polymer to plasticizer.

Samples that utilized PVA as the polymer displayed more consistent results in the mid-range of each testing parameter, while samples that contained chitosan as the polymer displayed less consistent results that more broadly spanned the extremes of the parameter ranges. This result may be partially attributable to the differences between steamed and boiled biomat samples; boiled samples were able to more uniformly incorporate the contents of polymer solutions and therefore showed better performance, whereas steamed samples tended to be much more brittle. It appeared that PVA was more readily and uniformly absorbed by steamed biomats than chitosan, which may explain the more consistent data obtained for PVA samples.

Example 6

Effect of Glycerol Content on Textile Material Properties

The procedure of Example 5 was repeated, except that the polymer/plasticizer solution contained no polymer (i.e. no PVA or chitosan) and the plasticizer (i.e. glycerol) content

TABLE 1

Material Properties of MK7 Leather Analog Samples with Varying Polymer-Plasticizer Ratios

| Sample No. | PVA wt % | Chitosan wt % | Glycerol wt % | PP ratio | DOS % | ML % | TS (MPa) | Flexibility |
|---|---|---|---|---|---|---|---|---|
| 1 | 10 | 0 | 15 | 0.67 | 113.84 | 39.93 | 3.88 | 9.00 |
| 2 | 10 | 0 | 10 | 1.00 | 127.91 | 32.23 | 5.09 | 8.83 |
| 3 | 10 | 0 | 8 | 1.25 | 125.87 | 28.43 | 4.99 | 6.00 |
| 4 | 10 | 0 | 4 | 2.50 | 142.46 | 18.66 | NA | 1.67 |
| 5 | 5 | 0 | 10 | 0.50 | 120.84 | 33.21 | 3.29 | 8.83 |
| 6 | 5 | 0 | 8 | 0.63 | 130.81 | 27.92 | 3.89 | 8.67 |
| 7 | 5 | 0 | 4 | 1.25 | 125.05 | 21.89 | NA | 2.83 |
| 8 | 0 | 4 | 15 | 0.27 | 147.65 | 36.01 | 2.70 | 5.00 |
| 9 | 0 | 4 | 10 | 0.40 | 177.02 | 26.80 | 8.61 | 3.83 |
| 10 | 0 | 4 | 6 | 0.67 | 189.90 | 21.46 | 5.78 | 3.33 |
| 11 | 0 | 4 | 4 | 1.00 | 229.21 | 36.46 | 7.68 | 2.67 |
| 12 | 0 | 4 | 2 | 2.00 | 164.35 | 17.39 | NA | 0.67 |
| 13 | 0 | 2 | 15 | 0.13 | 97.39 | 40.63 | 3.25 | 9.83 |
| 14 | 0 | 2 | 10 | 0.20 | 107.74 | 25.65 | 4.43 | 6.00 |
| 15 | 0 | 2 | 6 | 0.33 | 114.43 | 22.28 | 8.46 | 4.17 |
| 16 | 0 | 2 | 4 | 0.50 | 128.01 | 18.56 | NA | 0.67 |

Certain trends were evident regardless of the type of polymer (PVA vs. chitosan) used: an increase in tensile strength as the PP ratio increases, an increase in the degree of swelling as the PP ratio increases, a decrease in mass loss as the PP ratio increases, and a decrease in flexibility as the PP ratio increases. The introduction of polymers into MK7 biomats and subsequent heat-pressing causes the formation of covalent and non-covalent bonds between the fungal mycelia and polymer molecules. These polymer molecules also bind to one another to create an entanglement of bound structures. Plasticizing agents, such as glycerol, are "free floating" molecules that remain unbound to both the polymers and the MK7 structures and serve to block the formation of chemical bonds between polymers and biomass. When plasticizers are sparsely present, more chemical bonding can occur, leading to materials of increased strength and brittleness. When plasticizers are present in abundance, they block the formation of chemical bonds and lead to materials that are flexible but lack strength. This phenomenon is evidenced by the wide range of tensile strengths (2.70 MPa was varied to assess the effect of glycerol content on the material properties of the fungal textile material.

Figure 7:
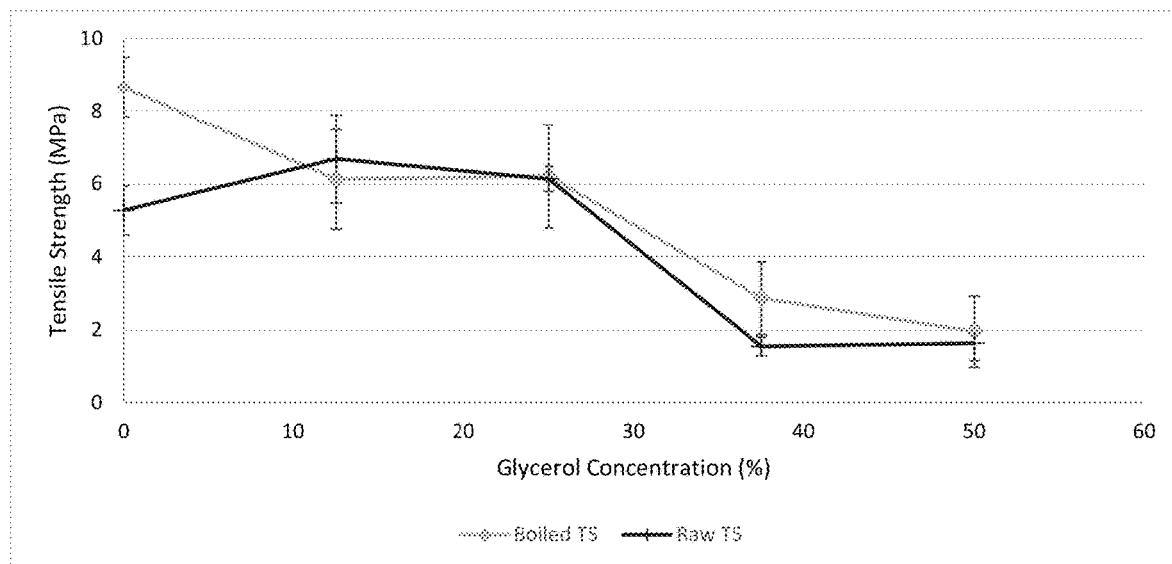
FIG. 7 is a graph of the tensile strength of an MK7 leather analog material as a function of glycerol content, according to embodiments of the present invention.
Figure 8:
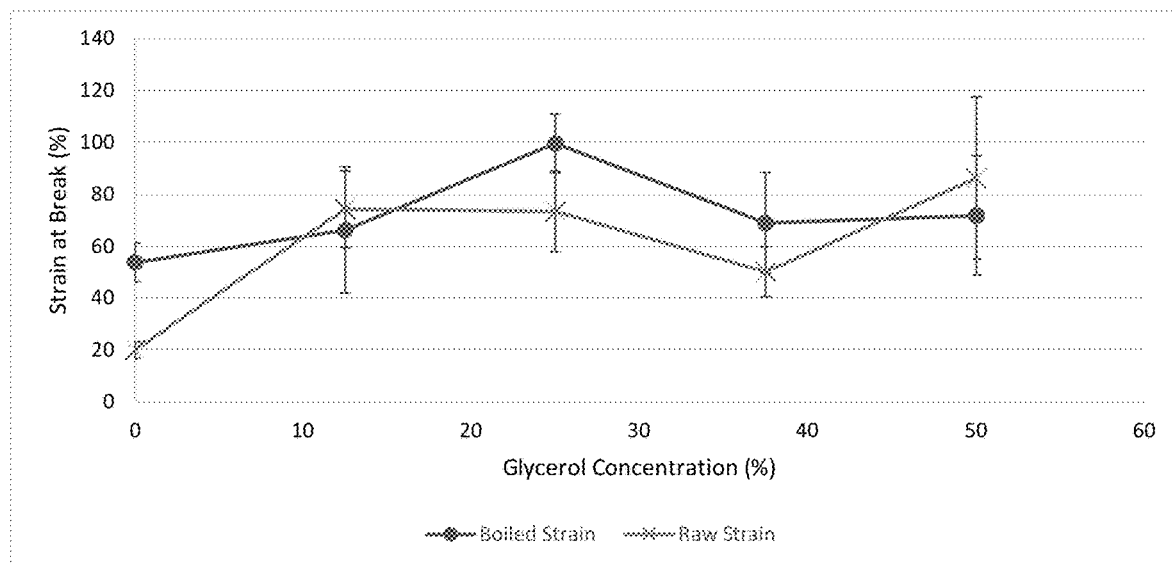
FIG. 8 is a graph of the strain at break of an MK7 leather analog material as a function of glycerol content, according to embodiments of the present invention.
Figure 9:
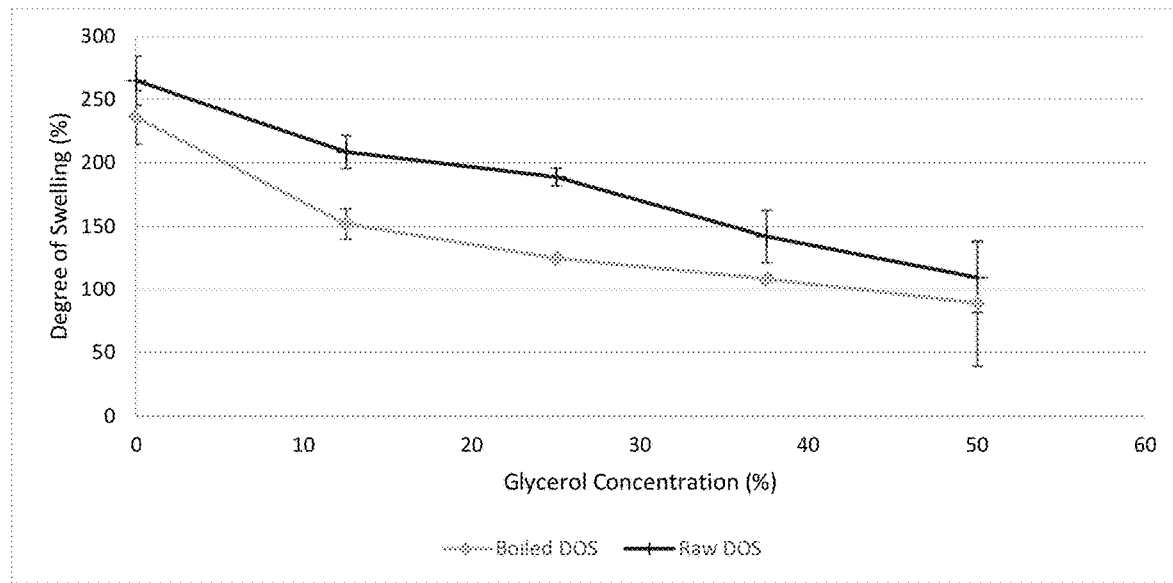
FIG. 9 is a graph of the degree of swelling of an MK7 leather analog material as a function of glycerol content, according to embodiments of the present invention.
Figure 10:
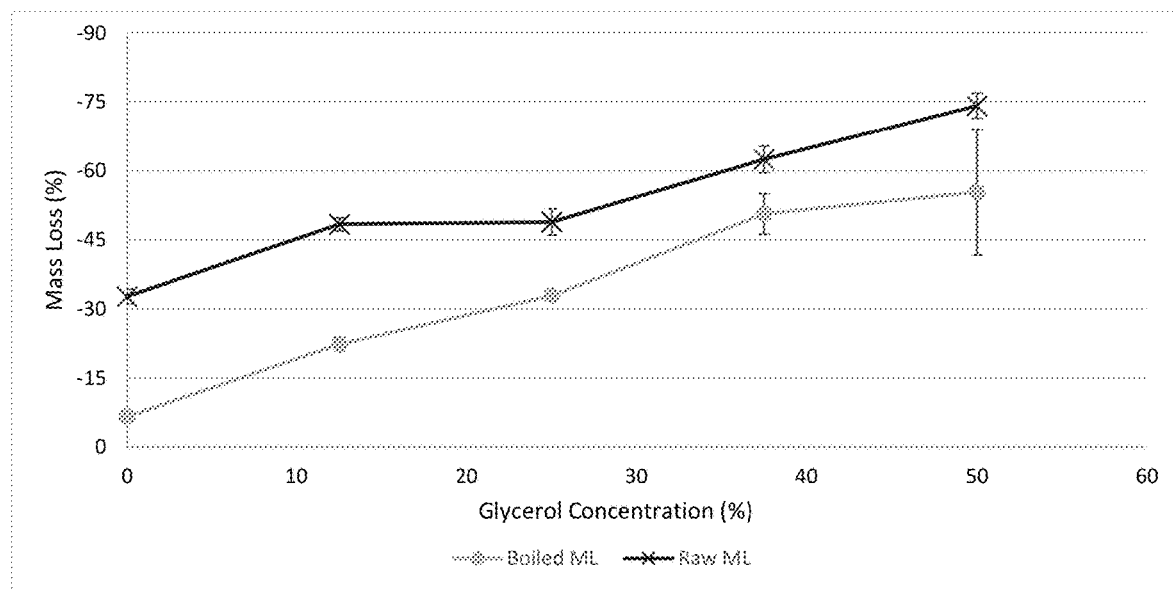
FIG. 10 is a graph of the mass loss upon soaking of an MK7 leather analog material as a function of glycerol content, according to embodiments of the present invention.

Over the range of glycerol concentration tested for MK7 leather samples, distinct trends in TS, strain at break (SAB), DOS, and ML were observed. The TS of MK7 leather, as illustrated in FIG. 7, was observed to decrease with an increase in glycerol concentration; a maximum TS of 8.65 MPa was achieved for samples made from pre-boiled biomass and no added glycerol, and a minimum TS value of 1.55 MPa was recorded for the raw biomass sample with an added glycerol concentration of 37.5%. The SAB of MK7 leather, as illustrated in FIG. 8, was observed to increase with an increase in glycerol concentration, although the samples made from pre-boiled biomass were less representative of this trend, most likely due to incomplete drying of some samples prior to strain testing. Additionally, the DOS of MK7 leather, as illustrated in FIG. 9, was observed to decrease with an increase in glycerol concentration, while the ML, as illustrated in FIG. 10, was observed to increase with an increase in glycerol concentration.

Glycerol acts by disrupting polymer-polymer interactions, increasing free space, and thus increasing the mobility of the polymer molecules. In MK7 leather embodiments according to the present invention, there is a mixture of PVA and/or chitosan polymers, along with native MK7 cells and excreted biopolymers (EPS). In the absence of glycerol, the added polymers, cells, and biopolymers can form more hydrogen, ionic, and covalent bonds to one another; molecular mobility and free space are low, while bond concentration is high. In this state, the material is more rigid and requires more energy to stretch or bend. Measured TS are therefore higher, and strains lower, when the glycerol concentration is low, and vice versa.

Example 7

Effect of Loading Ratio on Textile Material Properties

The procedure of Example 5 was repeated, except that the polymer/plasticizer solution contained no plasticizer (i.e. no added glycerol) and the total polymer content (i.e. total amount of PVA and/or chitosan) was varied to assess the effect of loading ratio on the material properties of the fungal textile material.

Figure 11:
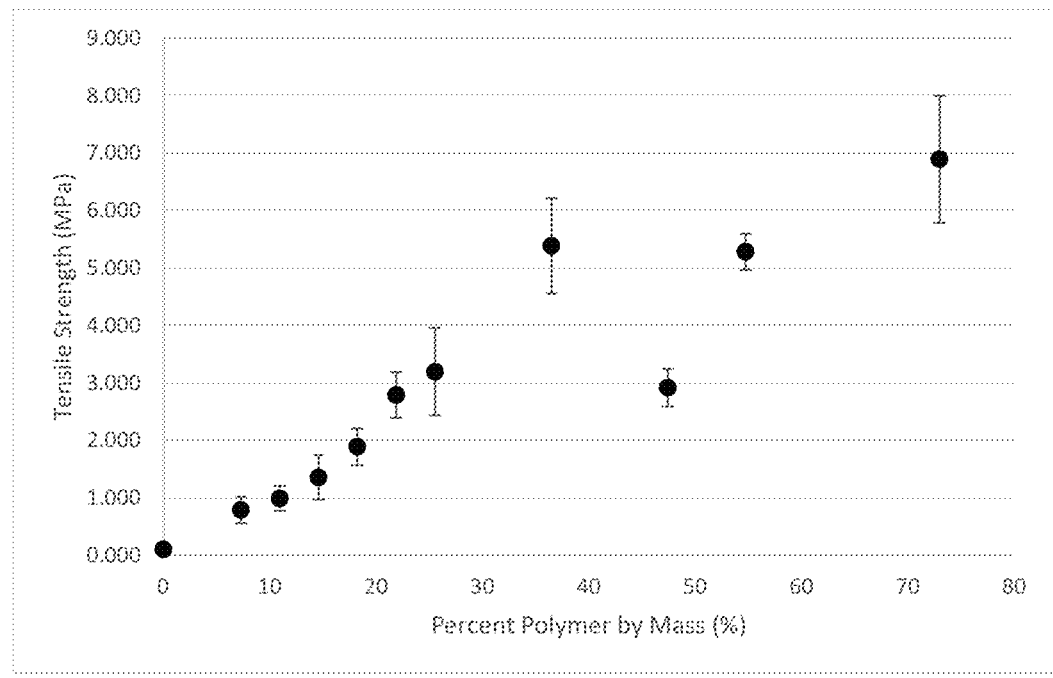
FIG. 11 is a graph of the tensile strength of an MK7 leather analog material as a function of loading ratio, according to embodiments of the present invention.

The TS of MK7 leather, as illustrated in FIG. 11, was shown to increase with an increase in polymer concentration; in other words, at the lowest loading ratio, the highest tensile strength was observed and vice versa. The TS was observed to increase linearly with polymer concentration up to a polymer concentration of about 36.5%, and then a drop in TS was observed at a polymer concentration of about 47.5%. At polymer concentrations of more than about 47.5%, the TS increased linearly to a maximum value of 6.89 MPa at a polymer concentration of 73%. Without wishing to be bound by any particular theory, it is believed that this effect is attributable to the many hydroxyl and amine groups present in PVA and chitosan molecules; these groups can form covalent and non-covalent bonds with biological structures and with other polymer molecules. As the polymer concentration increases, so too does the concentration of intermolecular bonds. High bond concentration then leads to improved strength of material. Additionally, the unprocessed biomass used to create the leather samples contains both remaining glycerol from media and EPS molecules created by the organism. The glycerol, and likely some components of the EPS, serve as plasticizing agents to the leather structure. Based on the results of the glycerol concentration experiment, it can be reasonably inferred that increasing the biomass concentration, and thus the plasticizer concentration, likely causes a decrease in the TS of samples.

Figure 12:
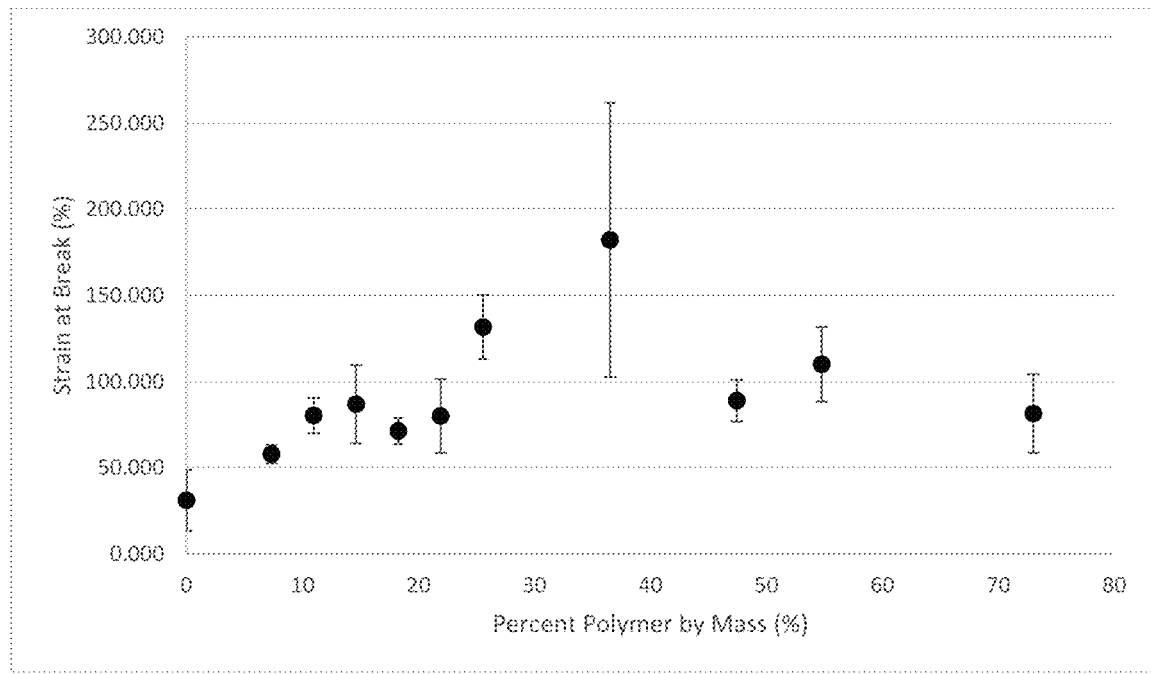
FIG. 12 is a graph of the strain at break of an MK7 leather analog material as a function of loading ratio, according to embodiments of the present invention.

The SAB of MK7 leather samples, as illustrated in FIG. 12, was observed to increase linearly with polymer concentration to a maximum value of 182% at a polymer concentration of 36.5%. As polymer concentration increased past 36.5%, the SAB was observed to then decrease linearly. Without wishing to be bound by any particular theory, it is believed that this effect is attributable to the competing effects of intermolecular bonding and plasticization within the leather structure. At high loading ratios, biomass and plasticizer concentrations are high while bond concentration is low, and the lack of intermolecular bonds leads to a material that has a low tension limit; thus, during tensile testing, the tension limit is likely reached prior to significant material strain, causing material failure at low strains. At the median loading ratio (a polymer concentration of 37.5%), by contrast, significant intermolecular bonding likely occurs. Additionally, due to significant incorporation of biomass at the median loading ratio, the samples are also significantly plasticized. These properties lead to a material with both a moderately high tension limit, and a moderately high strain limit. During tensile tests, the material can stretch significantly prior to reaching either its tension or strain limits. At lower loading ratios, the samples are no longer significantly plasticized. They contain a large concentration of polymers that form intermolecular bonds and therefore have a high tensile limit. However, the lack of plasticizing molecules leads to low strain limits and maximum TS values are reached at lower corresponding SAB values.

Figure 13:
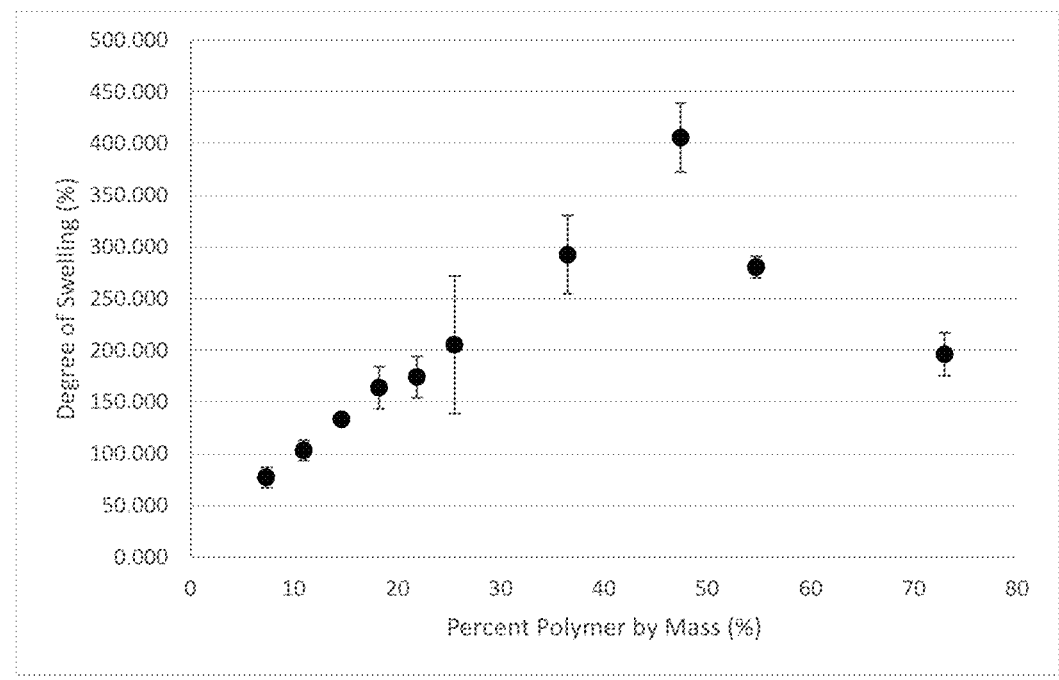
FIG. 13 is a graph of the degree of swelling of an MK7 leather analog material as a function of loading ratio, according to embodiments of the present invention.

A similar trend to that of SAB was observed for the DOS of leather samples, as illustrated in FIG. 13. The DOS of samples increased linearly with an increase in polymer concentration to a maximum value of 405% at a polymer concentration of 47.5%. As the polymer concentration increased past 47.5%, a linear decrease in DOS was observed. PVA and chitosan are known to form hydrogels, i.e. materials that comprise a three-dimensional mesh or network of physically and chemically bound polymer molecules. When not fully crosslinked, the hydrogel network is flexible and contains spaces between polymer strands, and the hydrogel can thus stretch and hold large amounts of water in the spaces between the polymer strands. When fully crosslinked, spaces between polymer strands are bound and the material is less able to flex as water is absorbed. In this crosslinked state, hydrogels have less water holding capacity. Without wishing to be bound by any particular theory, it is believed that, at high loading ratios, there are fewer available bonding sites for water molecules due to the small quantity of polymer molecules. Therefore, at high loading ratios, there is less capacity to absorb water. The maximum DOS values were observed at median polymer concentrations; at these concentrations, there was a relatively high polymer concentration, and a relatively high biomass concentration. The biomass contains absorbed glycerol and leads to a plasticized polymer network with low crosslinking and a high water holding capacity. As the polymer concentration increases further, the plasticization effect decreases with decreasing absorbed glycerol. This leads to a more highly crosslinked material that is unable to hold as much water.

Figure 14:
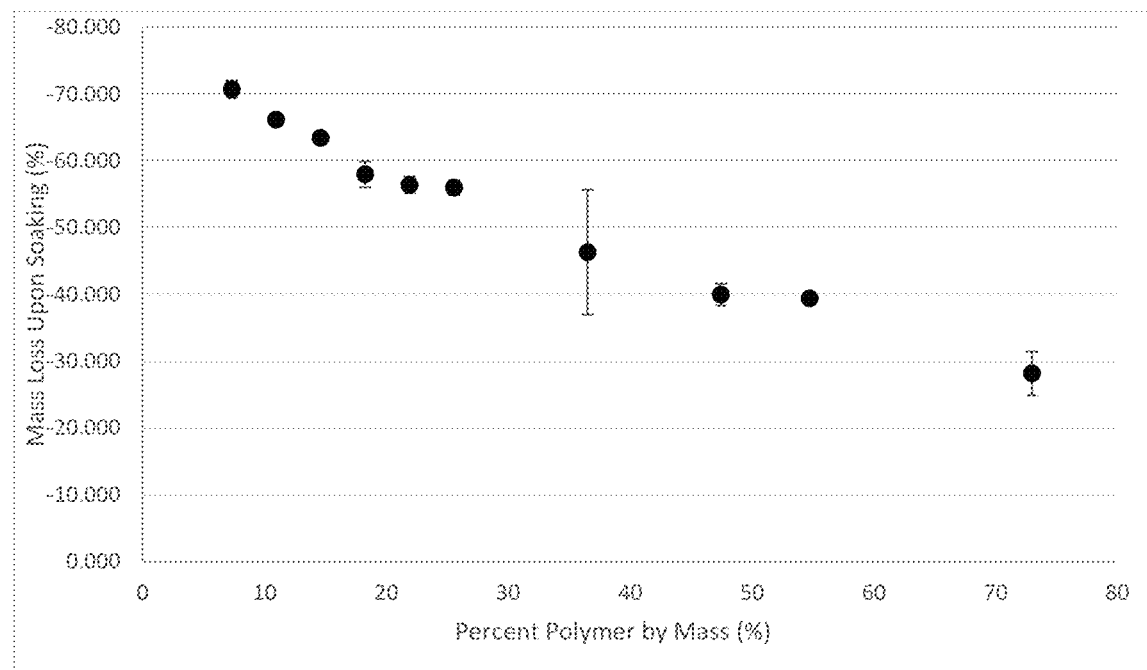
FIG. 14 is a graph of the mass loss upon soaking of an MK7 leather analog material as a function of loading ratio, according to embodiments of the present invention.

The ML values of MK7 leather however did not display any local maxima. Instead, the ML values, as illustrated in FIG. 14, were observed to decrease linearly with an increase in polymer concentration. Without wishing to be bound by any particular theory, it is believed that this effect is attributable to the decreasing amount of biomass associated with decreasing loading ratio. The biomass contains a large proportion of water-soluble compounds, which may diffuse into the aqueous phase when the biomass is soaked. The difference in mass from before and after soaking is therefore much higher for high loading ratio samples that contain significant masses of soluble compounds.

Example 8

Effect of Polyvinyl Alcohol-Chitosan Ratio on Textile Material Properties

The procedure of Example 5 was repeated, except that the polymer/plasticizer solution contained no plasticizer (i.e. no added glycerol), the total polymer content (i.e. total amount of PVA and/or chitosan) was held constant, and the ratio of PVA to chitosan was varied to assess the effect of varying polymer compositions on the material properties of the fungal textile material.

Figure 15:
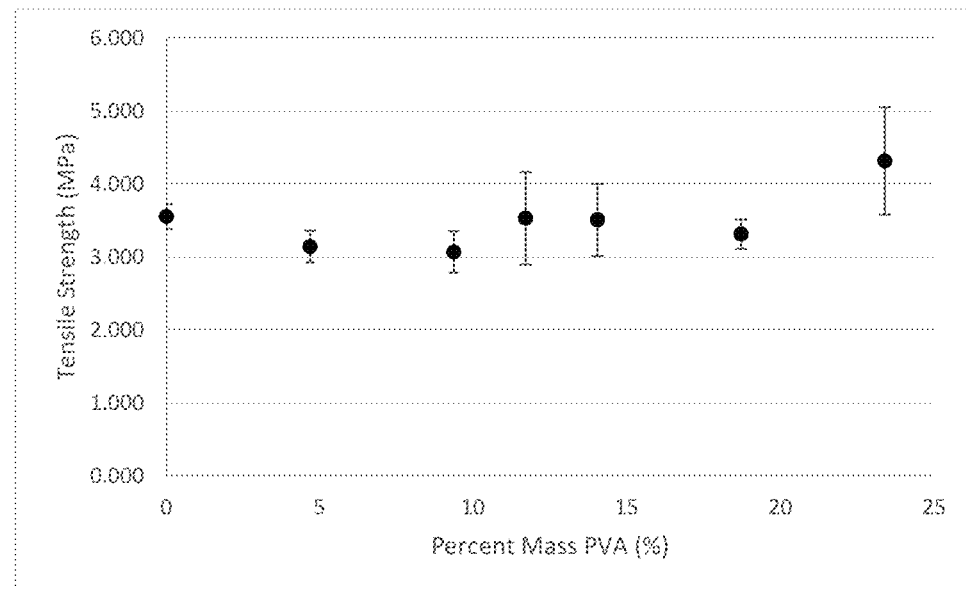
FIG. 15 is a graph of the tensile strength of an MK7 leather analog material as a function of polyvinyl alcohol:chitosan ratio, according to embodiments of the present invention.
Figure 16:
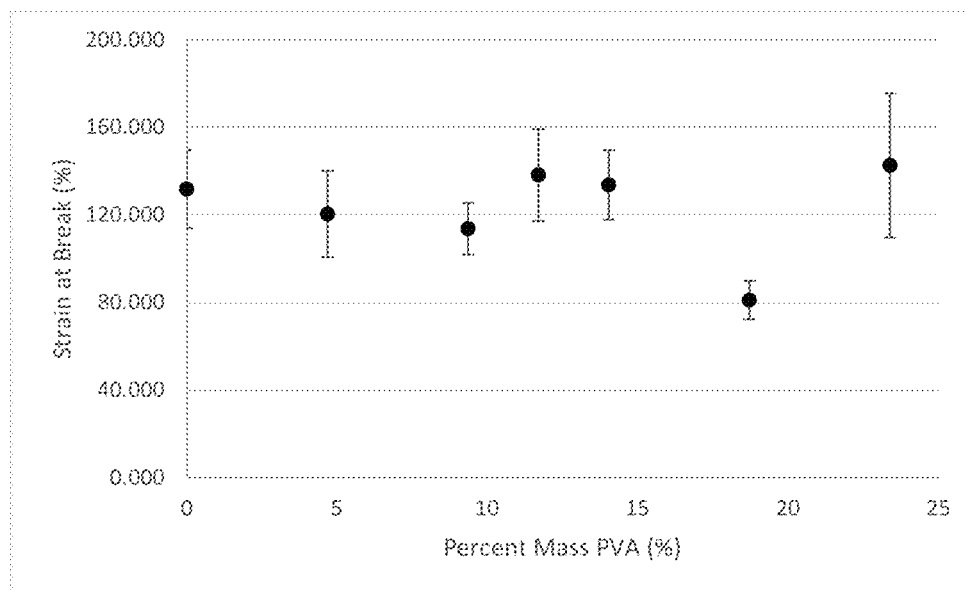
FIG. 16 is a graph of the strain at break of an MK7 leather analog material as a function of polyvinyl alcohol:chitosan ratio, according to embodiments of the present invention.

The TS of MK7 leather samples, as illustrated in FIG. 15, were observed to have local maxima at PVA:chitosan weight ratios of 0:100, 50:50, and 100:0. These points correspond to PVA concentrations of 0%, 11.7%, and 23.4% and TS values at these points were 3.55 MPa, 3.53 MPa, and 4.32 MPa, respectively. The SAB of samples, as illustrated in FIG. 16, was observed to have local maxima at the same PVA: chitosan ratios observed for the TS. Values for SAB at these points were 143%, 138%, and 132%, respectively. Without wishing to be bound by any particular theory, it is possible that local TS maxima are observed when one polymer is absent and when the polymers are present in equal amounts because chemical bonding of one polymer may be disrupted by the inclusion of small amounts of the other polymer, i.e. chitosan, present in small amounts, may form aggregates within a larger matrix of PVA and vice versa. The polymer aggregates would compete with the biomass for binding sites of the large polymer matrix leading to decreased strength while also disrupting the ability of polymer molecules to move and stretch. This would explain the low values of TS and SAB observed at PVA:chitosan ratios of 80:20, 60:40, 40:60, and 20:80. When approximately equal amounts of each polymer are added, aggregates may not form and a homogenous polymer matrix may thus be present. In the absence of aggregates, there would be an increased degree of bonding between polymers and biomass. Additionally, lack of aggregates would allow for the movement and flexure of polymer molecules. This would explain the increase in TS and SAB observed at the 50:50 PVA: chitosan ratio.

Figure 17:
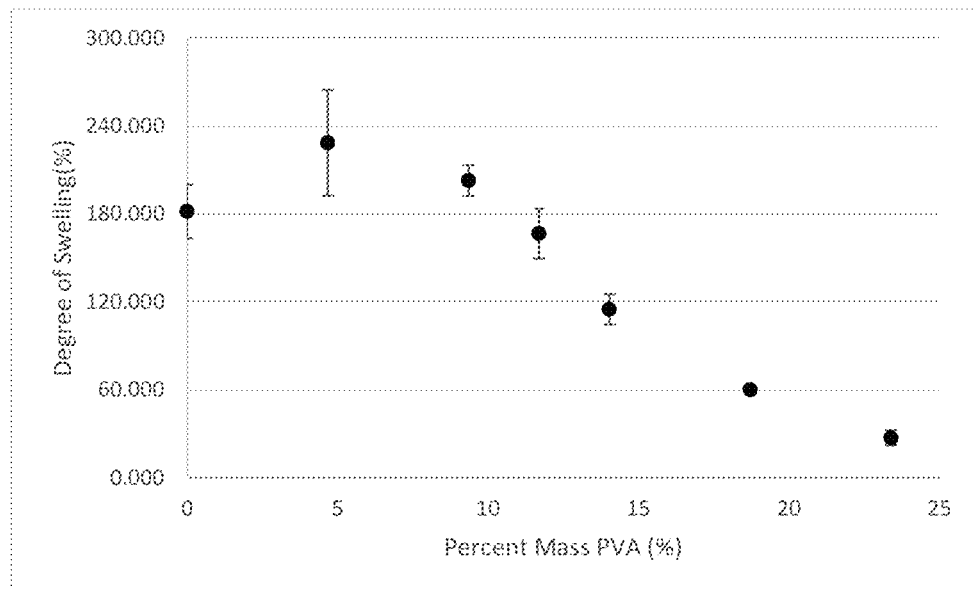
FIG. 17 is a graph of the degree of swelling of an MK7 leather analog material as a function of polyvinyl alcohol:chitosan ratio, according to embodiments of the present invention.
Figure 18:
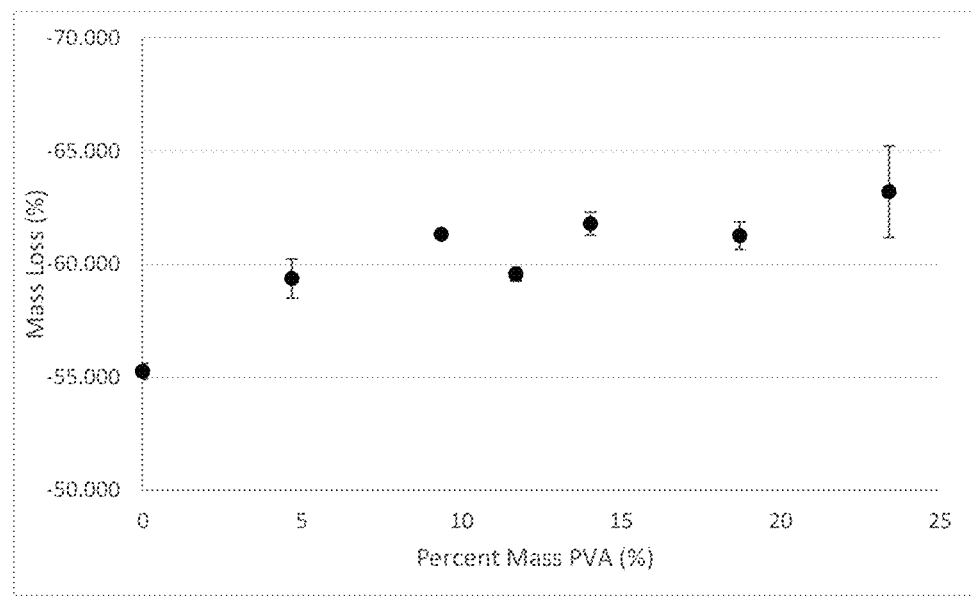
FIG. 18 is a graph of the mass loss upon soaking of an MK7 leather analog material as a function of polyvinyl alcohol:chitosan ratio, according to embodiments of the present invention.
Figure 19A:
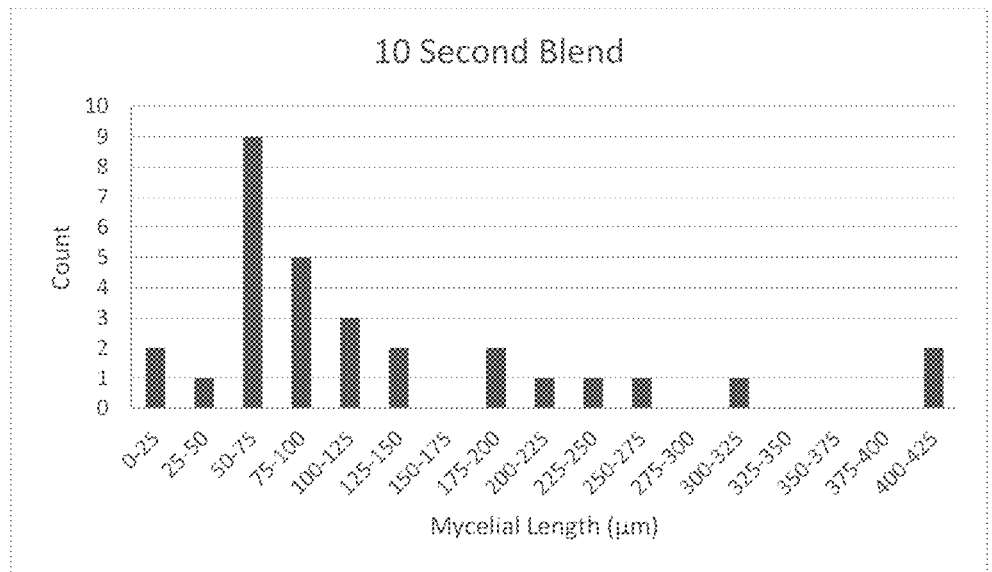
FIGS. 19A, 19B, 19C, and 19D are histograms of size-reduced fungal particles after 10 seconds, 20 seconds, 40 seconds, and 60 seconds, respectively, of blending in a conventional household blender, according to embodiments of the present invention.
Figure 19B:
Figure 19C:
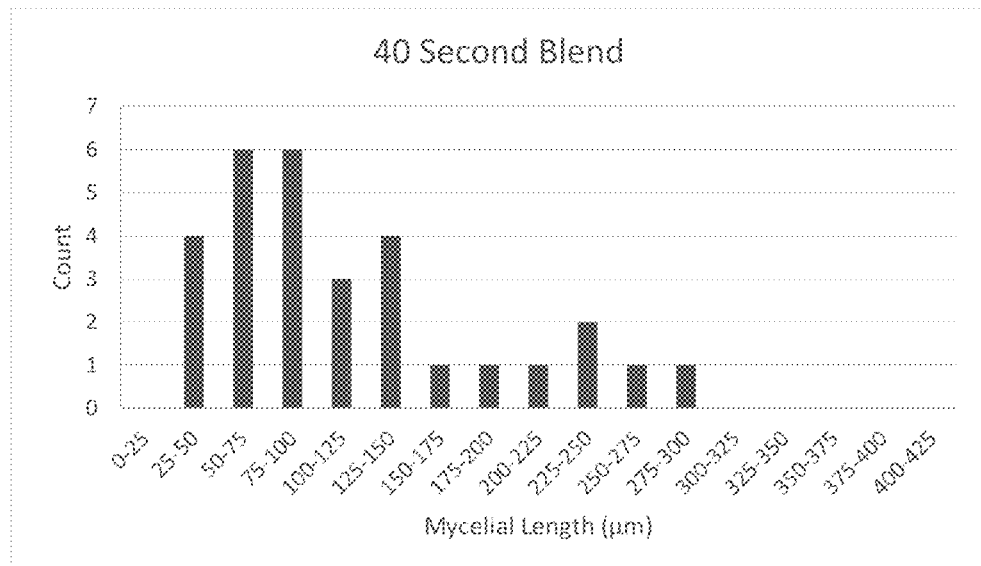
Figure 19D:

The DOS of leather samples, as illustrated in FIG. 17, was observed to decrease with an increase in the PVA concentration of samples. The ML of samples, as illustrated in FIG. 18, displayed an opposite trend. DOS values were three times as large in samples with chitosan as the sole polymer as compared to samples with PVA as the sole polymer. Without wishing to be bound by any particular theory, it is believed that chitosan molecules have a higher affinity for water molecules than molecules of PVA, possibly due to the positive charge on the amine group of chitosan at low pH. This charged amine group may also be more likely to bind to other molecules, e.g. biomass particles, glycerol, or EPS constituents, within the system. Due to the charged amine group, chitosan molecules may be more likely to remain bound during soaking, which would explain the lower ML values observed at higher concentrations of Ch and vice versa.

Example 9

Effect of Blending Time on Fungal Particle Length 40 grams of raw (unprocessed) fungal biomass and 40 mL of deionized water were placed into a small Oster blender and blended for 10 seconds. 3 mL of the resulting mixture was removed from the blender and combined with 27 mL of deionized water to form 30 mL of a "10-second blend" test material. The remaining mixture in the blender was blended for an additional 10 seconds, and another 3 mL sample was removed and combined with 27 mL of deionized water to form 30 mL of a "20-second blend" test material. This process was repeated with another 20 seconds of blending to obtain a "40-second blend," and again after still another 20 seconds of blending to obtain a "60-second blend." Each of the test materials was then further diluted 9:1 in deionized water to form four 300 mL samples, each comprising 1 vol % of the blended mixture.

75 µL of each of the four 1 vol % samples was placed onto a microscope slide, and photomicrographs of each sample were taken. In each photomicrograph, the apparent length of 30 fungal particles was measured, and these apparent lengths were converted to the true length of each particle based on the magnification used in the microscope. Histograms of particle length for the blends are illustrated in FIGS. 19A, 19B, 19C, and 19D, respectively.

Example 10

Effect of Loading Ratio on Foaming During Manufacture

Figure 20:
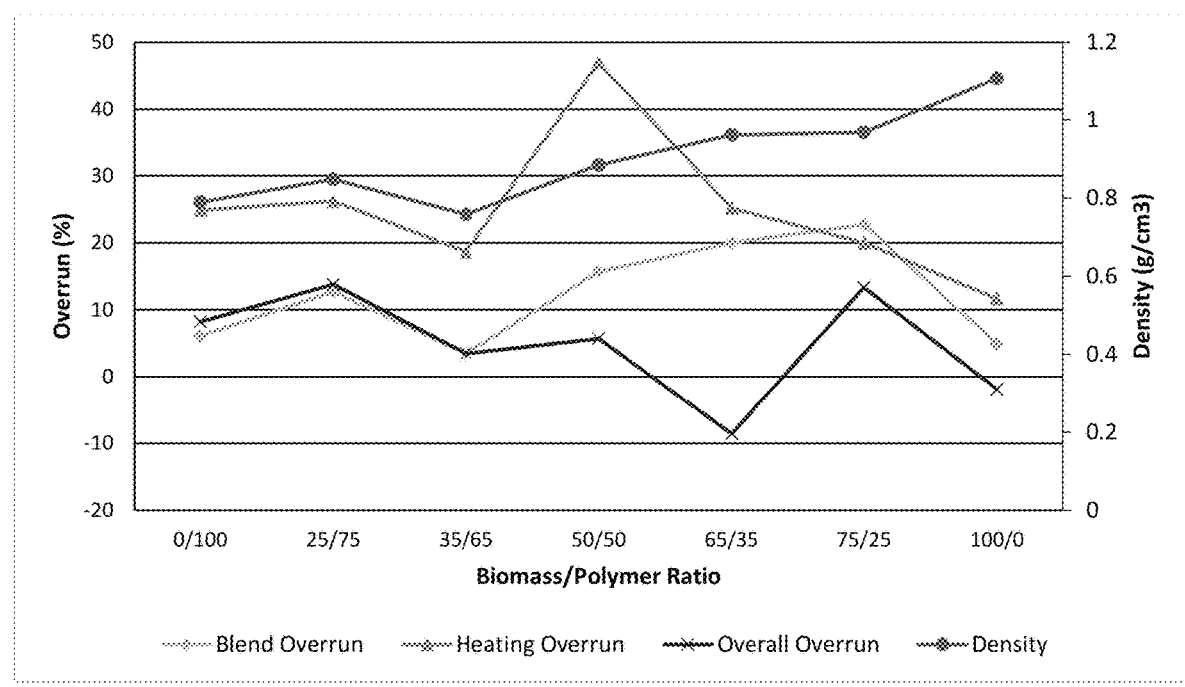
FIG. 20 is a graph of blend overrun, heating overrun, overall overrun, and density of solutions of fungal particles in water as a function of loading ratio, according to embodiments of the present invention.

Raw (unprocessed) fungal biomass was chopped into pieces approximately 1 cm square and added in varying amounts to each of several 400 mL beakers together with water, a PVA solution, chitosan, and adipic acid. The height of the mixture in each beaker was measured, and each mixture was then blended for one minute using a Hamilton Beach HB08 hand mixer, whereupon the height of the mixture was measured again. Each mixture was then stirred (large stir bar, 60 rpm) at 180° C. for 30 minutes, after which the height of the mixture was measured a third time, and then a fourth time after addition of a volume of acetic acid to the beaker; the mixture was stirred for 10 additional minutes during cooling. Each mixture was then poured into a flat tray, allowed to dry for two days at room temperature, then removed from the tray and heat-pressed at 275° F. in silicone textured molds for ten minutes at a time, five separate times. The density of each heat-pressed sample was then measured. FIG. 20 illustrates the "blend overrun," "heating overrun," and "overall overrun"—respectively, the change in volume relative to the starting mixture after blending, heating, and acetic acid addition—as well as the density for each mixture as a function of the loading ratio.

Example 11

Physical Properties of Fungal Leather Analogs—Size-Reduced Vs. Intact Biomass

Eight samples of a fungal leather analog material were produced according to the method illustrated in FIG. 3 and the description associated therewith, except as otherwise noted. Of these eight samples, three were made from inactivated fungal biomass that was size-reduced prior to step 310—a first sample had no non-fungal textile backing, a second sample had a non-fungal textile (cotton) backing on one side of the fungal layer, and a third sample had a non-fungal textile (cotton) layer "sandwiched" between two fungal layers. The other five samples were made from intact (non-size-reduced) biomats produced by a surface fermentation process—fourth, fifth, and sixth samples had no non-fungal textile backing, a seventh sample had a non-fungal textile (cotton) backing on one side of the fungal layer, and a third sample had a non-fungal textile (cotton) layer "sandwiched" between two fungal layers.

The size-reduced fungal biomasses were prepared as follows: water and thawed (previously frozen) processed biomass were added to a Vitamix blender in a 1:1 mass ratio. These were bended together for approximately 2 minutes to produce a homogenous mixture of size-reduced biomass in water. Separately, a solution of water, glycerol, chitosan, citric acid, and hydrochloric acid was prepared, with the respective components in a mass ratio of 200:17.5:6.3:1:13.5 respectively. The total mass of solution was equal to that of the biomass-water blended mixture. Once the chitosan was dissolved, the aqueous polymer solution and the biomass-water mixture were combined. The newly formed mixture was stirred under heat for approximately 30 min such that a homogenous paste was formed. This paste was then cast into a flat nonstick tray and allowed to dry at ambient conditions. Once dried, the newly formed sheet material was heat pressed at 100° C. for 10 minutes.

For those samples having non-fungal (cotton) layers, cotton backing material was adhered to the sample using an aqueous solution of chitosan (1% w/v), citric acid (1% w/v), and hydrogen chloride (1% v/v). The chitosan solution was painted onto appropriate side(s) of the fungal layer, and the cotton was applied to the wetted surface. The chitosan adhesive was allowed to dry for approximately 20 minutes, and the sample was then heat-pressed at 275° F. for two minutes to bond the backing material.

The eight fungal leather analog material samples were tested for nine physical properties—thickness, tensile strength, tensile force, elongation at break, tear resistance, density, flexural rigidity, degree of swelling, and mass loss after soaking. The results of these tests are given in Table 2 below.

glass trays were placed in a wrapped reactor at a temperature of 27° C. and allowed to incubate for 120 hours, with photographs of each tray taken at 72, 96, and 120 hours. The biomass from each tray was then harvested and inactivated in deionized water at 70° C. for 30 minutes. The wet yield of each sample was determined after inactivation to assess relative growth performance.

Each sample of biomass was then transformed into a fungal leather analog material according to the method described in Example 11 above. After tanning, various physical parameters of each sample were measured. The results are given in Table 3 (the values shown are the average for each CN ratio).

TABLE 3

| Parameter | CN ratio | | | |
|---|---|---|---|---|
| | 5 | 8.875 | 10 | 20 |
| Wet mass (g) | 63.25 | 95.7 | 84.175 | 82.5 |
| Finished mass (g) | 6.35 | 13.375 | 10.4 | 8.475 |
| Thickness (mm) | 0.565 | 1.115 | 0.8975 | 0.6575 |
| Density (g/cm$^3$) | 0.89101 | 1.07821 | 0.97116 | 0.94101 |
| Tensile strength (MPa) | 1.41537 | 1.71588 | 2.551 | 2.01343 |

TABLE 2

| Parameter | Unit | Size-reduced biomass | | | Intact biomass | | | | |
|---|---|---|---|---|---|---|---|---|---|
| | | | | | No textile #1 | No textile #2 | No textile #3 | | |
| | | No textile | Textile backing | Sandwiched textile | | | | Textile backing | Sandwiched textile |
| Thickness | mm | 1.4 | 2 | 2.5 | 0.4 | 0.85 | 1 | 0.61 | 0.90 |
| Tensile strength | MPa | 6.5 | 6.3 | 9.8 | 3.65 | 1.75 | 3.16 | 4.93 | 3.31 |
| Tensile force | N | 54.6 | 75.6 | 147 | 8.83 | 8.86 | 18.96 | 18.07 | 17.86 |
| Elongation at break | % | 17.8 | 20.5 | 18.3 | 17.45 | 13.79 | 20.53 | 9.01 | 11.67 |
| Tear resistance | N/mm | 6.4 | 17.5 | 17.2 | 0.64 | — | — | 48.57 | 31.90 |
| Density | g/cm$^3$ | 1.1 | — | — | 1.39 | 1.26 | 1.51 | 1.11 | 1.42 |
| Flexural rigidity | g · cm | 10.59 | — | — | 1.45 | 3.98 | 8.37 | 3.88 | 7.42 |
| Degree of swelling | % | 49.33 | — | — | 49.12 | 51.29 | 47.17 | — | — |
| Mass loss after soaking | % | 53.37 | — | — | 49.67 | 49.04 | 47.83 | — | — |

Example 12

Effect of Carbon-Nitrogen Ratio on Properties of Fungal Leather Analog Materials Four growth media for surface fermentation of fungal biomats (as described in, e.g., the '050, '626, and '421 applications) were prepared, each medium having an identical fructose content. The molar carbon-to-nitrogen ratio ("CN ratio") of each medium was adjusted by increasing or decreasing the combined content of ammonium sulfate and urea (holding the ratio of these two components to each other constant) until the media had CN ratios of 5, 8.875, 10, and 20, respectively. Each medium was inoculated with 5% v/v of an MK7 inoculum via shake flask inoculation.

250 mL of each inoculated medium was poured into each of four glass trays, resulting in 16 total inoculated trays. The TABLE 3-continued

| Parameter | CN ratio | | | |
|---|---|---|---|---|
| | 5 | 8.875 | 10 | 20 |
| Elongation at break (%) | 12.2409 | 12.5634 | 14.4092 | 12.9312 |
| Tear resistance (N/mm) | 1.13463 | 1.7848 | 1.21465 | 0.79766 |
| Degree of swelling (%) | 15.2407 | 22.5345 | 22.1204 | 16.9055 |
| Mass loss (%) | 55.6727 | 48.5781 | 50.6389 | 59.0071 |
| Flexural rigidity (g · cm) | 1.20936 | 5.03108 | 1.70845 | 0.44633 |

Various qualitative distinctions between the samples were also observed, both before and after tanning process. Biomats grown on media having a CN ratio of 5 were more "slippery" and noticeably thinner in places, especially in portions of the biomat grown near the center of the tray; once inactivated, these fungal samples were extremely flexible. Biomats grown on media having CN ratios of 8.875 and 10 were very stiff after inactivation, likely due to the thickness of the biomat. Biomats grown on media having a CN ratio of 20 were more flexible than those grown on media having CN ratios of 8.875 and 10, both before and after the inactivation step.

After the tanning process, it was observed that samples derived from media having a CN ratio of 5 had uneven thickness and were inflexible in those areas where the material was thickest; areas that were under greater pressure during the heat-pressing step were shinier and had a smoother texture, possibly due to the compression of the heat press aligning and compacting filaments of the filamentous fungus. Samples derived from media having a CN ratio of 8.875 were thickest and shrunk the most during the drying step, had uneven surface textures, and felt stiffer than other samples. Samples derived from media having a CN ratio of 10 were intermediate in thickness and were more flexible than the samples derived from media having a CN ratio of 8.875, but also displayed an uneven surface; like the samples derived from media having a CN ratio of 5, areas exposed to the greatest compression during the heat-pressing step were noticeably shinier. Samples derived from media having a CN ratio of 20 were intermediate in thickness between the CN ratio 5 and CN ratio 10 samples, and were relatively flexible and had slightly more uniform surfaces; once again, those areas that were most compressed during heat-pressing were shiniest.

Example 13

Thermal Doping of Fungal Leather Analogs

Each of five experimental samples was prepared as follows: 75 grams of glycerol, 27 grams of chitosan, 4.3 grams of citric acid, 880 milliliters of water, and 13.5 milliliters of concentrated hydrochloric acid were placed in a beaker and stirred until the chitosan dissolved. Separately, 80 grams of wet filamentous fungal biomass, produced by a surface fermentation method as described herein and in the '050, '626, and '421 applications, and 80 milliliters of water were placed in a kitchen blender and blended until homogeneous. 7.2 grams of a thermal dopant was then added to the blender (except in the case of the control sample), and the mixture was again blended until homogeneous. 160 grams of the chitosan solution were then added to the blender, and this mixture was again homogenized; 300 grams of the resulting mixture was poured into a small nonstick tray and dried at 90° F. for 23 hours. The dried sample was heat-pressed at 100° C. for 10 minutes to produce a flat sheet of moderate flexibility approximately 2 millimeters thick.

Thermal properties of each of the samples were measured. The results of these measurements are given in Table 4; control samples of undoped hide leather, undoped blended fungal leather analog, and undoped leather made from intact biomats (CN ratios of 8.875, 10, and 20, denoted "CN8," "CN10," and "CN20," respectively) were also tested for comparison.

TABLE 4

| Sample ID | Dopant | Thermal conductivity (W/m · K) | Thermal diffusivity (mm$^2$/s) | Volumetric specific heat (MLJ/m$^3$ · K) |
|---|---|---|---|---|
| LC | None (hide leather control) | 0.100 | 0.091 | 1.096 |
| ALU | Aluminum oxide | 0.243 | 0.132 | 1.867 |
| CNT | None (fungal leather control) | 0.181 | 0.122 | 1.487 |
| EVA | Ethylene vinyl acetate | 0.215 | 0.081 | 2.655 |
| Lig | Lignin | 0.199 | 0.139 | 1.443 |
| YTT | Yttrium oxide | 0.155 | 0.058 | 2.669 |
| Bent | Bentonite | 0.200 | 0.054 | 3.704 |
| CN8 | None | 0.234 | 0.138 | 1.691 |
| CN10 | None | 0.314 | 0.132 | 2.373 |
| CN20 | None | 0.302 | 0.216 | 1.399 |

Example 14

Effect of Polyvinyl Acetate on Material Performance

A large mixture of biomass, water, glycerol, and adipic acid was mixed in a blender and separated into five equal portions. Five separate 6% polymer solutions containing polyvinyl alcohol (PVA) and chitosan in an 80:20 mass ratio were made, each solution containing a different type of Kuraray PVA. Each polymer solution was combined with a portion of the biomass mixtures, thereby making five separate leather precursor mixtures. Each of these leather precursor mixtures was individually mixed using a handheld immersion blender and poured into a small Pyrex tray, then dried at room temperature with a fan blowing over the trays. When each sample reached a moisture content of no more than 20%, it was heat-pressed at 100° C. for ten minutes, two separate times. The samples were then allowed to dry overnight at room temperature and subsequently tested for tensile and tear strength and qualitatively examined for texture and water resistance. Each leather sample had a loading ratio of 75:25 and a plasticizer content of 22.5 wt %. Results of this testing are provided in Table 5.

TABLE 5

| PVA Type/ Name | Molecule Description | Degree of Hydrolysis | Viscosity (mPa.s) | Sample | Tensile Strength (N/mm$^2$) | Average (N/mm$^2$) | Tear Strength (N/mm) | Average (N/mm) | Texture Notes | Water Resistance Notes |
|---|---|---|---|---|---|---|---|---|---|---|
| Exceval HR-3010 | Copolymer of PVA and PE. 80:20 | 99.3 | 13.8 | a b c | 3.579 2.837 3.414 | 3.277 | 5.877 6.210 | 6.044 | Smooth surface. Cracks on both sides when bent 180 degrees. Low to Medium flexibility. | Droplets bead up on both sides. Minimal swelling. Minimal discoloration. |
| Exceval RS-2117 | Copolymer of PVA and PE. 80:20 | 98.1 | 27.8 | a b c | 3.574 3.548 3.394 | 3.505 | 5.788 7.870 7.987 | 7.215 | Smooth surface. Cracks on both sides when bent 180 degrees. Lower flexibility. | Droplets bead up on both sides. Minimal swelling. Minimal discoloration. |

TABLE 5-continued

| PVA Type/ Name | Molecule Description | Degree of Hydrolysis | Viscosity (mPa.s) | Sample | Tensile Strength (N/mm$^2$) | Average (N/mm$^2$) | Tear Strength (N/mm) | Average (N/mm) | Texture Notes | Water Resistance Notes |
|---|---|---|---|---|---|---|---|---|---|---|
| Exceval AQ-4104 | Copolymer of PVA and PE. 80:20 | 98.6 | 4.3 | a b c | 3.145 3.073 3.849 | 3.356 | 5.315 6.016 5.009 | 5.447 | Smooth surface. Cracks on both sides when bent 180 degrees. Lowest flexibility. | Droplets spread over surface on both sides. Relatively fast absorption. Minimal discoloration. |
| Poval 28-98 S2 | Pure PVA | 98.8 | 27.3 | a b c | 4.590 4.330 5.449 | 4.790 | 7.726 7.558 6.171 | 7.152 | Smooth surface. Cracks on the non-skin side when bent 180 degrees. Medium flexibility. | Droplets bead up on both sides. Slightly faster absorption. Minimal swelling. Minimal discoloration. |
| Elvanol 71-30 | Pure PVA | 99.6 | 29.1 | a b c | 4.905 3.529 3.073 | 3.836 | 5.566 6.428 | 5.997 | Smooth surface. Cracks on both sides when bent 180 degrees. Low to Medium flexibility. | Droplets bead up on both sides. Minimal swelling. Minimal discoloration. |

The viscosity of the PVA, which correlates directly with molecular weight, had a significant effect on tensile and tear strength, with low-viscosity PVAs resulting in poor tensile and tear properties. For higher-viscosity PVA types, the degree of hydrolysis appeared to be the determining factor for tensile and tear properties; samples with a low degree of hydrolysis displayed better tensile and tear properties. Without wishing to be bound by any particular theory, the present inventors hypothesize that a higher concentration of acetate groups acts as a plasticizer, allowing for free movement of internal molecules and reduced cracking and brittleness on a microscopic level, thereby increasing the overall strength and flexibility of samples.

The present disclosure, in various aspects, embodiments, and configurations, includes components, methods, processes, systems and/or apparatus substantially as depicted and described herein, including various aspects, embodiments, configurations, sub-combinations, and subsets thereof. Those of skill in the art will understand how to make and use the various aspects, aspects, embodiments, and configurations, after understanding the present disclosure. The present disclosure, in various aspects, embodiments, and configurations, includes providing devices and processes in the absence of items not depicted and/or described herein or in various aspects, embodiments, and configurations hereof, including in the absence of such items as may have been used in previous devices or processes, e.g., for improving performance, achieving ease and\or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more, aspects, embodiments, and configurations for the purpose of streamlining the disclosure. The features of the aspects, embodiments, and configurations of the disclosure may be combined in alternate aspects, embodiments, and configurations other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed aspects, embodiments, and configurations. Thus, the following claims are hereby incorporated into this Detailed Description, with each claim standing on its own as a separate preferred embodiment of the disclosure.

Moreover, though the description of the disclosure has included description of one or more aspects, embodiments, or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

The invention claimed is:

1. A textile composition, comprising:
an inactivated fungal biomass; and
a polymer,
wherein the polymer is infiltrated into the inactivated fungal biomass to a fungal biomass:polymer loading ratio of between about 25:75 and about 75:25, and
wherein the textile composition has a tensile strength a at least about 2 MPa.

2. The textile composition of claim 1, further comprising at least one component selected from the group consisting of a plasticizer, a crosslinker, and a dye, wherein the polymer and the at least one component are distributed in the inactivated fungal biomass.

3. The textile composition of claim 1, having a thickness of at least about 1 mm.

4. The textile composition of claim 1, having a tear force of at least about 30 N.

5. The textile composition of claim 1, having a tear strength of at least about 10 N/mm.

6. The textile composition of claim 1, having a flexural rigidity of no more than about 5 gram-centimeters.

7. The textile composition of claim 1, wherein the tensile strength of the textile composition is between about 2 MPa and about 8 MPa.

8. The textile composition of claim 1, having a water spotting grey scale rating of at least about 3.

9. The textile composition of claim 1, having a light color fastness blue wool rating of at least about 4.

10. The textile composition of claim 1, having a rub color fastness grey scale rating, when dry, of at least about 3.

11. The textile composition of claim 1, having a rub color fastness grey scale rating, when wet, of at least about 2.

12. The textile composition of claim 1, having a strain at break of between about 75% and about 275%.

13. The textile composition of claim 1, having a degree of swelling of between about 200% and about 450%.

14. The textile composition of claim 1, having a mass loss upon soaking of between about 20% and about 60%.

15. A textile composition, comprising:
an inactivated fungal biomass;
a polymer; and
at least one backing layer of a non-fungal textile material,
wherein the polymer is infiltrated into the inactivated fungal biomass to a fungal biomass:polymer loading ratio of between about 25:75 and about 75:25.

16. The textile composition of claim 15, wherein the non-fungal textile material is selected from the group consisting of an acrylic textile, an alpaca textile, an angora textile, a cashmere textile, a coir textile, a cotton textile, an eisengarn textile, a hemp textile, a jute textile, a Kevlar textile, a linen textile, a microfiber textile, a mohair textile, a nylon textile, an olefin textile, a pashmina textile, a polyester textile, a piña textile, a ramie textile, a rayon textile, a sea silk textile, a silk textile, a sisal textile, a spandex textile, a spider silk textile, a wool textile, and combinations and mixtures thereof.

17. A textile composition, comprising:
an inactivated fungal biomass;
a polymer; and
a thermal dopant,
wherein the polymer is infiltrated into the inactivated fungal biomass to a fungal biomass:polymer loading ratio of between about 25:75 and about 75:25.

18. The textile composition of claim 17, wherein the thermal dopant is selected from the group consisting of a ceramic material, a metallic material, a polymeric material, and combinations and mixtures thereof.

19. The textile composition of claim 17, wherein the thermal dopant is selected from the group consisting of activated charcoal, aluminum oxide, bentonite, diatomaceous earth, ethylene vinyl acetate, lignin, nanosilica, polycaprolactone, polylactic acid, silicone, and yttrium oxide.

20. The textile composition of claim 17, wherein a thermal characteristic of the textile composition is altered relative to the same thermal characteristic of the textile composition in the absence of the thermal dopant, wherein the thermal characteristic is selected from the group consisting of thermal effusivity, thermal conductivity, heat capacity, and combinations thereof.

21. The textile composition of claim 15, further comprising at least one component selected from the group consisting of a plasticizer, a crosslinker, and a dye, wherein the polymer and the at least one component are distributed in the inactivated fungal biomass.

22. The textile composition of claim 15, having a tear force of at least about 30 N.

23. The textile composition of claim 15, having a tear strength of at least about 10 N/mm.

24. The textile composition of claim 15, having a flexural rigidity of no more than about 5 gram-centimeters.

25. The textile composition of claim 15, wherein the tensile strength of the textile composition is between about 2 MPa and about 8 MPa.

26. The textile composition of claim 15, having a water spotting grey scale rating of at least about 3.

27. The textile composition of claim 15, having a rub color fastness grey scale rating, when dry, of at least about 3.

28. The textile composition of claim 15, having a strain at break of between about 75% and about 275%.

29. The textile composition of claim 15, having a degree of swelling of between about 200% and about 450%.

30. The textile composition of claim 15, having a mass loss upon soaking of between about 20% and about 60%.

* * * * *